US008609627B2

(12) United States Patent
Cho et al.

(10) Patent No.: US 8,609,627 B2
(45) Date of Patent: Dec. 17, 2013

(54) PURINE NUCLEOSIDE MONOPHOSPHATE PRODRUGS FOR TREATMENT OF CANCER AND VIRAL INFECTIONS

(75) Inventors: Jong Hyun Cho, Snellville, GA (US); Steven J. Coats, McDonough, GA (US); Raymond F. Schinazi, Atlanta, GA (US); Hongwang Zhang, Tucker, GA (US); Longhu Zhou, Atlanta, GA (US)

(73) Assignees: RFS Pharma, LLC, Tucker, GA (US); Emory University, Atlanta, GA (US)

( * ) Notice: Subject to any disclaimer, the term of this patent is extended or adjusted under 35 U.S.C. 154(b) by 86 days.

(21) Appl. No.: 13/144,718

(22) PCT Filed: Feb. 9, 2010

(86) PCT No.: PCT/US2010/023563
§ 371 (c)(1),
(2), (4) Date: Oct. 5, 2011

(87) PCT Pub. No.: WO2010/091386
PCT Pub. Date: Aug. 12, 2010

(65) Prior Publication Data
US 2012/0040924 A1 Feb. 16, 2012

Related U.S. Application Data

(60) Provisional application No. 61/150,628, filed on Feb. 6, 2009.

(51) Int. Cl.
*A01N 43/04* (2006.01)
*A61K 31/70* (2006.01)
(52) U.S. Cl.
USPC ............... 514/48; 514/43; 514/45; 514/46; 514/47; 536/27.1; 536/27.13; 536/27.2

(58) Field of Classification Search
None
See application file for complete search history.

(56) References Cited

U.S. PATENT DOCUMENTS

| 5,444,063 | A | 8/1995 | Schinazi |
| 6,784,166 | B2 | 8/2004 | Devos et al. |
| 2006/0079478 | A1 | 4/2006 | Boojamra et al. |
| 2007/0042988 | A1 | 2/2007 | Klumpp et al. |
| 2010/0016251 | A1 | 1/2010 | Sofia et al. |
| 2010/0279969 | A1 | 11/2010 | Schinazi et al. |

FOREIGN PATENT DOCUMENTS

| CA | 2047390 A1 | 1/1992 |
| CN | 1059528 A | 3/1992 |

(Continued)

OTHER PUBLICATIONS

Banker, G., et al. (Ed.), "Modern Pharmaceutics, 3rd Edition", Jan. 1996, p. 596 vol. 72, Publisher: Marcel Dekker, Inc.

(Continued)

*Primary Examiner* — Patrick Lewis
(74) *Attorney, Agent, or Firm* — Hultquist, PLLC; David Bradin

(57) ABSTRACT

The present invention is directed to compounds, compositions and methods for treating or preventing cancer and viral infections, in particular, HIV, HCV, Norovirus, Saporivirus, HSV-1, HSV-2, Dengue virus, Yellow fever, and HBV in human patients or other animal hosts. The compounds are certain 6-substituted purine monophosphates, and pharmaceutically acceptable, salts, prodrugs, and other derivatives thereof. In particular, the compounds show potent antiviral activity against HIV-1, HIV-2, HCV, Norovirus, Saporivirus, HSV-1, HSV-2, Dengue virus, Yellow fever, and HBV.

18 Claims, 13 Drawing Sheets

(56) References Cited

FOREIGN PATENT DOCUMENTS

| | | |
|---|---|---|
| EP | 0398231 A2 | 11/1990 |
| WO | 0112644 A1 | 2/2001 |
| WO | 0190121 A2 | 11/2001 |
| WO | 0232920 A2 | 4/2002 |
| WO | 2005000864 A1 | 1/2005 |
| WO | 2005021568 A2 | 3/2005 |
| WO | 2006121820 A1 | 11/2006 |
| WO | 2006130217 A2 | 12/2006 |
| WO | 2007027248 A2 | 3/2007 |
| WO | 2007030227 A2 | 3/2007 |
| WO | 2008005542 A2 | 1/2008 |
| WO | 2008100447 A2 | 8/2008 |
| WO | 2008121634 A2 | 10/2008 |
| WO | 2009116044 A2 | 9/2009 |
| WO | 2010068708 A2 | 6/2010 |
| WO | 2010091386 A2 | 8/2010 |

OTHER PUBLICATIONS

Karamov, E., et al., "Inhibition of human immunodeficiency virus production in cell culture by 5'-phosphites of 3'-azido-2',3'-dideoxynucleosides", "Molekulyarnaya Biologiya", 1990, pp. 1695-1701 (Abstract), vol. 24, No. 6.

Silverman, R., at al, "The Organic Chemistry of Drug Design and Drug Action", 1992, pp. 19-23.

Wolff, M. (Ed.), "vol. I: Principles and Practice", "Burger's Medicinal Chemistry and Drug Discovery, Fifth Edition", Dec. 19, 1994, pp. 975-977, Publisher: John Wiley & Sons.

Karlsson, A., et al., "The metabolism of 3'-azido-2',3'-dideoxyguanosine in CEM cells", "Biochemical and Biophysical Research Communications", 1990, pp. 273-279 (Abstract Only), vol. 166, No. 1.

Lennerstrand, J., et al., "Biochemical Studies on the Mechanism of Human Immunodeficiency Virus Type 1 Reverse Transcriptase Resistance to 1-(beta-D-Dioxolane)Thymine Triphosphate", "Antimicrobial Agents and Chemotherapy ", Jun. 2007, pp. 2078-2084, vol. 51, No. 6.

Seio, K., et al., "Synthesis and Properties of New Nucleotide Analogues Possessing Squaramide Moieties as New Phosphate Isosters", "Eur. J. Org. Chem.", Oct. 19, 2005, pp. 5163-5170.

Shirasaka, T., et al , "Lipophilic halogenated congeners of 2',3'-dideoxypurine nucleosides active against human immunodeficiency virus in vitro", "Proc. Natl. Acad. Sci.", Dec. 1990, pp. 9426-9430, vol. 87.

Sluis-Cremer, N., et al. , "The 3'-Azido Group Is Not the Primary Determinant of 3'-Azido-3'-deoxythymidine (AZT) Responsible for the Excision Phenotype of AZT-resistant HIV-1", "The Journal of Biological Chemistry", Jun. 20, 2005, pp. 29047-29052, vol. 280, No. 32.

Unpublished U.S. Appl. No. 13/132,920, filed Jun. 4, 2011.

Vivet-Boudou, V., et al. , "Nucleoside and nucleotide inhibitors of HIV-1 replication", "Cellular and Molecular Life Sciences", Jan. 2, 2006, pp. 163-186, vol. 63, No. 2.

Zielinski, W., et al., "Oligoaminonucleoside Phosphoramidates. Oligomerization of Dimers of 3'-Amino-3'-Deoxy-Nucleotides (GC and CG) in Aqueous Solution", "Nucleic Acids Research", 1987, pp. 1699-1715, vol. 15, No. 4.

Zielinski, W., et al., "The Template Properties of Tetranucleoside Triphosphoramidates Having Cytosine-Guanosine Residues", "J. Mol. Evol.", 1989, pp. 281-283, vol. 29.

Balzarini, J., et al., "Conversion of 2',3'-dideoxyadenosine (ddA) and 2',3'-didehydro-2',3'-dideoxyadenosine (d4A) to their corresponding aryloxyphosphoramidate derivatives markedly potentiates thieir activity against human immunodeficiency virus and hepatitis B virus", "FEBS Letters", 1997, pp. 324-328, vol. 410.

Mewshaw, J., et al., "Dioxolane Guanosine, the Active Form of the Prodrug Diaminopurine Dioxolane, Is a Potent Inhibitor of Drug-Resistant HIV-1 Isolates From Patients for Whom Standard Nucleoside Therapy Fails", "Journal of Acquired Immuno Deficiency Syndromes", 2002, pp. 11-20, vol. 29.

Bednarski, K., et al., "Synthesis of Racemic 2-Phosphonomethyl-1,3-Dioxolane Nucleoside Analogues as Potential Antiviral Agents", "Bioorganic & Medicinal Chemistry Letters", 1995, pp. 1741-1744, vol. 5, No. 15.

Elliott, R. et al., "Phosphonate Analogs of Carbocyclic Nucleotides", "J. Med. Chem.", Feb. 15, 1994, pp. 739-744, vol. 37.

Margolin, A., et al., "AMP Deaminase as a Novel Practical Catalyst in the Synthesis of 6-Oxopurine Ribosides and Their Analogs", "J. Org. Chem.", 1994, pp. 7214-7218, vol. 59.

| VIRUS (xxLAI) | MUTATIONS IN RT |
|---|---|
| HIV-1$_{K65R}$ | K65R |
| HIV-1$_{K70E}$ | K70E |
| HIV-1$_{L74V}$ | L74V |
| HIV-1$_{M184V}$ | M184V |
| HIV-1$_{AZT2}$ | D67N, K70R, T215F, K219Q |
| HIV-1$_{AZT3}$ | M41L, L210W, T215Y |
| HIV-1$_{AZT7}$ | M41L, D67N, K70R, T215F, K219Q |
| HIV-1$_{AZT9}$ | M41L, D67N, K70R, L210W, T215Y, K219Q |
| HIV-1$_{Q151M}$ | M41L, A62V, V75L, F77L, F116Y, Q151M |
| HIV-1$_{69INSERTION}$ | M41L, SS INSERT BETWEEN 69 AND 70, L210W, T215Y |

FIG.12

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence

```
<220> FEATURE:
<223> OTHER INFORMATION: A [gamma-32P]-ATP 5'-end labeled 20 nucleotide
      DNA primer

<400> SEQUENCE: 1
tcgggcgcca ctgctagaga                                               20

<210> SEQ ID NO 2
<211> LENGTH: 57
<212> TYPE: DNA
<213> ORGANISM: Artificial Sequence
<220> FEATURE:
<223> OTHER INFORMATION: DNA template for HIV1-RT
<220> FEATURE:
<221> NAME/KEY: misc_feature
<222> LOCATION: (28)..(28)
<223> OTHER INFORMATION: n is t or c

<400> SEQUENCE: 2
ctcagaccct tttagtcaga atggaaantc tctagcagtg gcgcccgaac agggaca     57

<210> SEQ ID NO 3
<211> LENGTH: 17
<212> TYPE: DNA
<213> ORGANISM: Artificial Sequence
<220> FEATURE:
<223> OTHER INFORMATION: sense primer for COXII

<400> SEQUENCE: 3
tgcccgccat catccta                                                  17

<210> SEQ ID NO 4
<211> LENGTH: 21
<212> TYPE: DNA
<213> ORGANISM: Artificial Sequence
<220> FEATURE:
<223> OTHER INFORMATION: probe for COXII

<400> SEQUENCE: 4
tcctcatcgc cctcccatcc c                                             21

<210> SEQ ID NO 5
<211> LENGTH: 23
<212> TYPE: DNA
<213> ORGANISM: Artificial Sequence
<220> FEATURE:
<223> OTHER INFORMATION: antisense primer for COXII

<400> SEQUENCE: 5
cgtctgttat gtaaaggatg cgt                                           23

<210> SEQ ID NO 6
<211> LENGTH: 17
<212> TYPE: DNA
<213> ORGANISM: Artificial Sequence
<220> FEATURE:
<223> OTHER INFORMATION: Sense primer for Exon 3 of the beta-actin gene

<400> SEQUENCE: 6
gcgcggctac agcttca                                                  17

<210> SEQ ID NO 7
<211> LENGTH: 18
<212> TYPE: DNA
<213> ORGANISM: Artificial Sequence
<220> FEATURE:
<223> OTHER INFORMATION: Probe for Exon 3 of the beta-actin gene
```

-continued

```
<400> SEQUENCE: 7
caccacggcc gagcggga                                                    18

<210> SEQ ID NO 8
<211> LENGTH: 22
<212> TYPE: DNA
<213> ORGANISM: Artificial Sequence
<220> FEATURE:
<223> OTHER INFORMATION: Antisense primer for Exon 3 of the beta-actin
      gene

<400> SEQUENCE: 8
tctccttaat gtcacgcacg at                                               22
```

PURINE NUCLEOSIDE MONOPHOSPHATE PRODRUGS FOR TREATMENT OF CANCER AND VIRAL INFECTIONS

CROSS-REFERENCE TO RELATED APPLICATIONS

This application is a U.S. national phase application under the provisions of 35 U.S.C. §371 of International Patent Application No. PCT/US 10/23563 filed Feb. 9, 2010, which in turn claims priority of U.S. patent application Ser. No. 61/150,628 filed Feb. 6, 2009. The disclosures of such international patent application and U.S. priority patent application are hereby incorporated herein by reference in their respective entireties, for all purposes.

FIELD OF THE INVENTION

The present invention is directed to compounds, methods and compositions for treating or preventing viral infections using nucleotide analogs. More specifically, the invention describes 6-substituted-2-amino purine nucleoside monophosphate and monophosphonate prodrugs and modified prodrug analogs, pharmaceutically acceptable salts, or other derivatives thereof, and the use thereof in the treatment of cancer or viral infection(s), and in particular 1) human immunodeficiency virus (HIV-1and HIV-2); 2) Flaviviridae family of viruses including hepatitis C (HCV), West Nile virus, Dengue virus, and Yellow fever; 3) Caliciviridae infection including Norovirus and Saporovirus; and 4) hepatitis B virus (HBV) infection. This invention teaches how to modify the metabolic pathway of specific 6-substituted-2-amino purine nucleosides and deliver nucleotide triphosphates to reverse transcriptases and polymerases at heretofore unobtainable therapeutically-relevant concentrations.

BACKGROUND OF THE INVENTION

Nucleoside analogs as a class have a well-established regulatory history, with more than 10 currently approved by the US Food and Drug Administration (US FDA) for treating human immunodeficiency virus (HIV), hepatitis B virus (HBV), or hepatitis C virus (HCV). The challenge in developing antiviral therapies is to inhibit viral replication without injuring the host cell. In HIV, a key target for drug development is reverse transcriptase (HIV-RT), a unique viral polymerase. This enzyme is active early in the viral replication cycle and converts the virus' genetic information from RNA into DNA, a process necessary for continued viral replication. Nucleoside reverse transcriptase inhibitors (NRTI) mimic natural nucleosides. In the triphosphate form, each NRTI competes with one of the four naturally occurring 2'-deoxynucleoside 5'-triphosphate (dNTP), namely, dCTP, dTTP, dATP, or dGTP for binding and DNA chain elongation near the active site of HIV-1 RT.

Reverse transcription is an essential event in the HIV-1 replication cycle and a major target for the development of antiretroviral drugs (see Parniak M A, Sluis-Cremer N. Inhibitors of HIV-1 reverse transcriptase. *Adv. Pharmacol.* 2000, 49, 67-109; Painter G R, Almond M R, Mao S, Liotta D C. Biochemical and mechanistic basis for the activity of nucleoside analogue inhibitors of HIV reverse transcriptase. *Curr. Top. Med. Chem.* 2004, 4, 1035-44; Sharma P L, Nurpeisov V, Hernandez-Santiago B, Beltran T, Schinazi R F. Nucleoside inhibitors of human immunodeficiency virus type 1 reverse transcriptase. *Curr. Top. Med. Chem.* 2004, 4 895-919). Two distinct groups of compounds have been identified that inhibit HIV-1 RT. These are the nucleoside or nucleotide RT inhibitors (NRTI) and the non-nucleoside RT inhibitors (NNRTI).

NRTI are analogs of deoxyribonucleosides that lack a 3'-OH group on the ribose sugar. They were the first drugs used to treat HIV-1 infection and they remain integral components of nearly all antiretroviral regimens.

In 1985, it was reported that the synthetic nucleoside 3'-azido-3'-deoxythymidine (zidovudine, AZT), one representative NRTI, inhibited the replication of HIV. Since then, several other NRTI, including but not limited to 2',3'-dideoxyinosine (didanosine, ddI), 2',3'-dideoxycytidine (zalcitabine, ddC), 2',3'-dideoxy-2',3'-didehydrothymidine (stavudine, d4T), (-)-2',3'-dideoxy-3'-thiacytidine (lamivudine, 3TC), (-)-2',3'-dideoxy-5-fluoro-3'-thiacytidine (emtricitabine, FTC), (1S,4R)-4-[2-amino-6-(cyclopropyl-amino)-9H-purin-9-yl]-2-cyclopentene-1-methanol succinate (abacavir, ABC), (R)-9-(2-phosphonylmethoxypropyl)adenine (PMPA, tenofovir disoproxil fumarate) (TDF), and (-)-carbocyclic 2',3'-didehydro-2',3'-dideoxyguanosine (carbovir) and its prodrug abacavir, have proven effective against HIV. After phosphorylation to the 5'-triphosphate by cellular kinases, these NRTI are incorporated into a growing strand of viral DNA causing chain termination, because they lack a 3'-hydroxyl group.

In general, to exhibit antiviral activity, NRTI must be metabolically converted by host-cell kinases to their corresponding triphosphate forms (NRTI-TP). The NRTI-TP inhibit HIV-1 RT DNA synthesis by acting as chain-terminators of DNA synthesis (see Goody R S, Muller B, Restle T. Factors contributing to the inhibition of HIV reverse transcriptase by chain terminating nucleotides in vitro and in vivo. *FEBS Lett.* 1991, 291, 1-5). Although combination therapies that contain one or more NRTI have profoundly reduced morbidity and mortality associated with AIDS, the approved NRTI can have significant limitations. These include acute and chronic toxicity, pharmacokinetic interactions with other antiretrovirals, and the selection of drug-resistant variants of HIV-1 that exhibit cross-resistance to other NRTI.

HIV-1 drug resistance within an individual arises from the genetic variability of the virus population and selection of resistant variants with therapy (see Chen R, Quinones-Mateu M E, Mansky L M. Drug resistance, virus fitness and HIV-1 mutagenesis. *Curr. Pharm. Des.* 2004, 10, 4065-70). HIV-1 genetic variability is due to the inability of HIV-1 RT to proofread nucleotide sequences during replication. This variability is increased by the high rate of HIV-1 replication, the accumulation of proviral variants during the course of HIV-1 infection, and genetic recombination when viruses of different sequence infect the same cell. As a result, innumerable genetically distinct variants (termed quasi-species) evolve within an individual in the years following initial infection. The development of drug resistance depends on the extent to which virus replication continues during drug therapy, the ease of acquisition of a particular mutation (or set of mutations), and the effect of drug resistance mutations on drug susceptibility and viral fitness. In general, NRTI therapy selects for viruses that have mutations in RT. Depending on the NRTI resistance mutation(s) selected, the mutant viruses typically exhibit decreased susceptibility to some or, in certain instances, all NRTI. From a clinical perspective, the development of drug resistant HIV-1 limits future treatment options by effectively decreasing the number of available drugs that retain potency against the resistant virus. This often requires more complicated drug regimens that involve intense dosing schedules and a greater risk of severe side effects due to drug toxicity. These factors often contribute to incomplete adherence to the drug regimen. Thus, the development of novel NRTI with excellent activity and safety profiles and limited or no cross-resistance with currently-available drugs is critical for effective therapy of HIV-1 infection.

The development of nucleoside analogs active against drug-resistant HIV-1 requires detailed understanding of the molecular mechanisms involved in resistance to this class of compounds. Accordingly, a brief overview of the mutations and molecular mechanisms of HIV-1 resistance to NRTI is provided. Two kinetically distinct molecular mechanisms of HIV-1 resistance to NRTI have been proposed (see Sluis-Cremer N, Arion D, Parniak M A. Molecular mechanisms of HIV-1 resistance to nucleoside reverse transcriptase inhibitors (NRTIs). *Cell Mol. Life Sci.* 2000; 57, 1408-22). One mechanism involves selective decreases in NRTI-TP versus normal dNTP incorporation during viral DNA synthesis. This resistance mechanism has been termed discrimination. The second mechanism involves selective removal of the chain-terminating NRTI-monophosphate (NRTI-MP) from the prematurely terminated DNA chain (see Arion D, Kaushik N, McCormick S, Borkow G, Parniak M A. Phenotypic mechanism of HIV-1 resistance to 3'-azido-3'-deoxythymidine (AZT): increased polymerization processivity and enhanced sensitivity to pyrophosphate of the mutant viral reverse transcriptase. *Biochemistry.* 1998, 37, 15908-17; Meyer P R, Matsuura S E, Mian A M, So A G, Scott W A. A mechanism of AZT resistance: an increase in nucleotide-dependent primer unblocking by mutant HIV-1 reverse transcriptase. *Mol. Cell.* 1999, 4, 35-43). This mechanism has been termed excision.

The discrimination mechanism involves the acquisition of one or more resistance mutations in RT that improve the enzyme's ability to discriminate between the natural dNTP substrate and the NRTI-TP. In this regard, resistance is typically associated with a decreased catalytic efficiency of NRTI-TP incorporation. NRTI-TP (and dNTP) catalytic efficiency is driven by two kinetic parameters, (i) the affinity of the nucleotide for the RT polymerase active site ($K_d$) and (ii) the maximum rate of nucleotide incorporation (kpol), both of which can be determined using pre-steady-state kinetic analyses (see Kati W M, Johnson K A, Jerva L F, Anderson K S. Mechanism and fidelity of HIV reverse transcriptase. *J. Biol. Chem.* 1992, 26: 25988-97).

For the excision mechanism of NRTI resistance, the mutant HIV-1 RT does not discriminate between the natural dNTP substrate and the NRTI-TP at the nucleotide incorporation step (see Kerr S G, Anderson K S. Pre-steady-state kinetic characterization of wild type and 3'-azido-3'-deoxythymidine (AZT) resistant human immunodeficiency virus type 1 reverse transcriptase: implication of RNA directed DNA polymerization in the mechanism of AZT resistance. *Biochemistry.* 1997, 36, 14064-70). Instead, RT containing "excision" mutations shows an increased capacity to unblock NRTI-MP terminated primers in the presence of physiological concentrations of ATP (typically within the range of 0.8-4 mM) or pyrophosphate (PPi) (see Arion D, Kaushik N, McCormick S, Borkow G, Parniak M A. Phenotypic mechanism of HIV-1 resistance to 3'-azido-3'-deoxythymidine (AZT): increased polymerization processivity and enhanced sensitivity to pyrophosphate of the mutant viral reverse transcriptase. *Biochemistry.* 1998, 37, 15908-17; Meyer P R, Matsuura S E, Mian A M, So A G, Scott W A. A mechanism of AZT resistance: an increase in nucleotide-dependent primer unblocking by mutant HIV-1 reverse transcriptase. *Mol. Cell.* 1999, 4, 35-43). NRTI resistance mutations associated with the excision mechanism include thymidine analog mutations (TAMS) and T69S insertion mutations.

Another virus that causes a serious human health problem is the hepatitis B virus (HBV). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a 2- to 6-month incubation period, during which the host is typically unaware of the infection, HBV infection can lead to acute hepatitis and liver damage, resulting in abdominal pain, jaundice and elevated blood levels of certain enzymes. HBV can cause fulminant hepatitis, a rapidly progressive, often fatal form of the disease in which large sections of the liver are destroyed.

Patients typically recover from the acute phase of HBV infection. In some patients, however, the virus continues replication for an extended or indefinite period, causing a chronic infection. Chronic infections can lead to chronic persistent hepatitis. Patients infected with chronic persistent HBV are most common in developing countries. By mid-1991, there were approximately 225 million chronic carriers of HBV in Asia alone and worldwide almost 300 million carriers. Chronic persistent hepatitis can cause fatigue, cirrhosis of the liver, and hepatocellular carcinoma, a primary liver cancer.

In industrialized countries, the high-risk group for HBV infection includes those in contact with HBV carriers or their blood samples. The epidemiology of HBV is very similar to that of HIV/AIDS, which is a reason why HBV infection is common among patients infected with HIV or suffering from AIDS. However, HBV is more contagious than HIV.

3TC (lamivudine), interferon alpha-2b, peginterferon alpha-2a, hepsera (adefovir dipivoxil), baraclude (entecavir), and Tyzeka (Telbivudine) are currently FDA-approved drugs for treating HBV infection. However, some of the drugs have severe side effects, and viral resistance develops rapidly in patients treated with these drugs.

Norovirus is one of four viral genera found in the non-enveloped positive strand RNA family Caliciviridae. The other three species in Caliciviridae are Lagovirus, Vesivirus, and Sapovirus. Sapovirus is the only member of the genus other than Norovirus which utilizes humans as hosts. The Norovirus genome is approximately 7.56 kb with three open reading frames (ORFs). The first ORF codes for nonstructural proteins including a helicase, a protease, and a RNA directed RNA polymerase (RDRP) all of which are required for replication of the virus. The remaining two ORFs code for Capsid proteins (Jiang, X. (1993) Virology 195(1):51-61). The numerous strains of Norovirus have been classified into 5 genogroups of which I, IV, and V infect humans (Zheng, D. P., et al. (2006) Virology 346(2):312-323) and are estimated by the CDC to cause approximately 23 million gastroenteritis cases, corresponding to 40% of foodborne illness each year in the US (Mead P. S. (1999) Emerg. Infect. Dis. 5(5):607-625).

Common symptoms are vomiting, diarrhea, and intestinal cramps. Vomiting is the most common symptom in children, while diarrhea is more common in infected adults. Dehydration is a significant concern. The loss of life due to this virus is about 300 patients per year in the United States, and these deaths are usually among patients with a weak immune system (Centers for Disease Control and Prevention. "Norwalk-like viruses:" public health consequences and outbreak management. MMWR 2001; 50 (No. RR-9):3). The incubation period from exposure to full infection is typically 24 to 48 hrs with approximately 30% of infected individuals showing no symptoms. Symptoms generally persist for 24 to 60 hrs (Adler, J. L. and Zickl, R., J. (1969) Infect. Dis. 119:668-

673). Viral shedding may last for up to 2 weeks following the infection, however, it is not clear whether this virus is infectious.

Norovirus is transmitted primarily by the fecal-oral route through contaminated food or water, person to person contact, aerosols of vomit or stool samples. Viral titers in stool samples can reach $10^6$ to $10^7$ particles per mL, and particles are stable to temperatures of 0° C. (32° F.) to 60° C. (140° F.) (Duizer, E. et al., (2004) Appl. Environ. Microbiol. 70(8); 4538-4543). The virus is highly infectious, and various sources suggest infection may require inoculation of as few as 10 to 100 viral particles (Centers for Disease Control and Prevention. "Norwalk-like viruses:" public health consequences and outbreak management. MMR 2001; 50(No. RR-9):3-6). This leads to epidemics in schools, nursing homes, cruise ships, hospitals, or other locations where people congregate.

Norovirus is named for Norwalk-like viruses, a name derived from an outbreak at a school in Norwalk, Ohio in 1968. The viral particle responsible for the Norwalk illness was identified in 1972 by immune electron microscopy following passage of rectal swab filtrates through three sets of human volunteers (Kapikian, A. Z. et al. (1972) J. Virol. 10:1075-1081). In following years, the virus was called small round structured virus due to its electron microscopic image, calicivirus since it a member of the Caliciviridae family, and/or probably most commonly Norwalk-like virus after the originally isolated strain. Common names for the virus include winter vomiting virus, stomach flu, food poisoning, and viral gastroenteritis. While the outcome of infection is generally non-life threatening, the cost of loss of use of facilities and loss of productivity is great, and, consequently, a therapy for treatment of Norovirus infection in humans would be very desirable.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473). Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads, and at least initially seems as though it would be difficult to screen a meaningful number of compounds with this system. Eventually the infectivity assay may be useful for screening entry inhibitors. Other groups, such as Ligocyte Pharmaceuticals, Inc. (http://www.ligocyte.com/) have focused on trying to develop a vaccine against Noroviruses, however, these efforts have not yet been successful and may prove difficult as has often been the case in viral systems where low replicase fidelity is an evolutionary benefit.

Hepatitis C virus (HCV) has infected more than 180 million people worldwide. It is estimated that three to four million persons are newly infected each year, 70% of whom will develop chronic hepatitis. HCV is responsible for 50-76% of all liver cancer cases, and two thirds of all liver transplants in the developed world. Standard therapy [pegylated interferon alfa plus ribavirin (a nucleoside analog)] is only effective in 50-60% of patients and is associated with significant side-effects. Therefore, there is an urgent need for new HCV drugs.

Hepatitis C virus genome comprises a positive-strand RNA enclosed in a nucleocapsid and lipid envelope and consists of 9.6 kb ribonucleotides, which encodes a large polypeptide of about 3000 amino acids (Dymock et al. Antiviral Chemistry & Chemotherapy 2000, 11, 79). Following maturation, this polypeptide is cut into at least 10 proteins. One of these proteins, NS5B, possesses polymerase activity and is involved in the synthesis of double-stranded RNA from the single-stranded viral RNA genome that serves as the template. The discovery of novel antiviral strategies to selectively inhibit HCV replication has long been hindered by the lack of convenient cell culture models for the propagation of HCV. This hurdle has been overcome first with the establishment of the HCV replicon system in 1999 (Bartenschlager, R., *Nat. Rev. Drug Discov.* 2002, 1, 911-916 and Bartenschlager, R., *J. Hepatol.* 2005, 43, 210-216) and, in 2005, with the development of robust HCV cell culture models (Wakita, T., et al., *Nat. Med.* 2005, 11, 791-6; Zhong, J., et al., *Proc. Natl. Acad. Sci. U.S.A.* 2005, 102, 9294-9; Lindenbach, B. D., et al., *Science* 2005, 309, 623-6).

HCV replication may be prevented through the manipulation of NS5B's polymerase activity via competitive inhibition of NS5B protein. Alternatively, a chain-terminator nucleoside analog also may be incorporated into the extending RNA strand. Recently, several patent applications (including WO 99/43691, WO 01/32153, WO 01160315, WO 01179246, WO 01/90121, WO 01/92282, WO 02/48165, WO 02/18404, WO 02/094289, WO 02/057287, WO 02/100415(A2), US 06/040890, WO 02/057425, EP 1674104(A1), EP 1706405 (A1), US 06/199783, WO 02/32920, US 04/6784166, WO 05/000864, WO 05/021568) have described nucleoside analogs as anti-HCV agents.

Proliferative disorders are one of the major life-threatening diseases and have been intensively investigated for decades. Cancer now is the second leading cause of death in the United States, and over 500,000 people die annually from this proliferative disorder. A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncongenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three means of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia.

Chemotherapy involves the disruption of cell replication or cell metabolism. It is used most often in the treatment of leukemia, as well as breast, lung, and testicular cancer. There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

Several synthetic nucleosides, such as 5-fluorouracil, have been identified that exhibit anticancer activity. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema.

Despite the availability of a vaccine (*Crit. Rev. Clin. Lab. Sci.* 2004, 41, 391-427). Yellow fever virus (YFV) continues to be a serious human health concern, causing approximately 30,000 deaths each year. YFV is one of the most lethal viral infections of humans (*Expert Rev. Vaccines* 2005, 4, 553-574). Of infected individuals approximately 15% will develop severe disease, with a fatality rate of 20 to 50% among those individuals. No approved therapies specific for treatment of YFV are available. Treatment is symptomatic-rest, fluids, and ibuprofen, naproxen, acetaminophen, or paracetamol may relieve symptoms of fever and aching. Aspirin should be avoided. Although the virus is endemic to Africa and South America, there is potential for outbreaks of YFV outside these areas and such imported cases have been reported (*J. Travel Med.* 2005, 12(Suppl. 1), S3-S11).

West Nile Virus (WNV) is from the family Flaviviridae and predominantly a mosquito-borne disease. It was first discovered in the West Nile District of Uganda in 1937. According to the reports from the Centers for Disease Control and Prevention, WNV has been found in Africa, the Middle East, Europe, Oceania, west and central Asia, and North America. Its first emergence in North America began in the New York City metropolitan area in 1999. It is a seasonal epidemic in North America that normally erupts in the summer and continues into the fall, presenting a threat to environmental health. Its natural cycle is bird-mosquito-bird and mammal. Mosquitoes, in particular the species *Culex pipiens*, become infected when they feed on infected birds. Infected mosquitoes then spread WNV to other birds and mammals including humans when they bite. In humans and horses, fatal Encephalitis is the most serious manifestation of WNV infection. WNV can also cause mortality in some infected birds. There is no specific treatment for WNV infection. In cases with milder symptoms, people experience symptoms such as fever and aches that pass on their own, although even healthy people have become sick for several weeks. In more severe cases, people usually need to go to the hospital where they can receive supportive treatment.

Dengue infection is also from the family Flaviviridae and is the most important arthropod-borne infection in Singapore (*Epidemiol News Bull* 2006, 32, 62-6). Globally, there are an estimated 50 to 100 million cases of dengue fever (DF) and several hundred thousand cases of dengue hemorrhagic fever (DHF) per year with and average fatality fate of 5%. Many patients recover from dengue infection with minimal or no residual illness. Dengue infections are usually asymptomatic, but can present with classic dengue fever, dengue haemorrhagic fever or dengue shock syndrome. Even for outpatients, the need for maintaining adequate hydration is highly important. Dengue infections can be effectively managed by intravenous fluid replacement therapy, and if diagnosed early, fatality rates can be kept below 1%. To manage the pain and fever, patients suspected of having a dengue infection should be given acetaminophen preparations. Aspirin and non-steroidal anti-inflammatory medications may aggravate the bleeding tendency associated with some dengue infection. However, some manifestations of dengue infection previously described include liver failure (*Dig Dis Sci* 2005, 50, 1146-7), encephalopathy (*J Trop Med Public Health* 1987, 18, 398-406), and Guillain-Barré syndrome (*Intern Med* 2006, 45, 563-4).

It has been discovered that, upon incubation in cell culture, or administration in vivo, that a wide variety of 6-substituted-3'-azido-2',3'-dideoxy purine nucleosides are converted to the corresponding 6-hydroxy-3'-azido-2',3'-dideoxy purine nucleosides. We have also found this to be true for a variety of other 6-substituted purine nucleosides. These compounds act as prodrugs for G or I analogs, much as is the case for the prodrug Abacavir and its in vivo conversion to the corresponding G analog Carbovir ((-)-carbocyclic 2',3'-didehydro-2',3'-dideoxyguanosine). This conversion seriously limits the variety of 6-substituted purine nucleosides triphosphates which can be formed in vivo as potential antiviral agents.

In light of the fact that acquired immune deficiency syndrome, AIDS-related complex, HCV, Norovirus, Saporovirus, HSV-1, HSV-2, Dengue virus, Yellow fever, cancer, and HBV have reached alarming levels worldwide, and have significant and in some cases tragic effects on the effected patient, there remains a strong need to provide new effective pharmaceutical agents to treat these diseases, with agents that have low toxicity to the host.

It would be advantageous to provide new antiviral or chemotherapy agents, compositions including these agents, and methods of treatment using these agents, particularly to treat drug resistant cancers or mutant viruses. The present invention provides such agents, compositions and methods.

SUMMARY OF THE INVENTION

The present invention provides compounds, methods and compositions for treating or preventing cancer or an HIV-1, HIV-2, HCV, Norovirus, Saporovirus, HSV-1, HSV-2, Dengue virus, Yellow fever, or HBV infection in a host. The methods involve administering a therapeutically or prophylactically-effective amount of at least one compound as described herein to treat or prevent an infection by, or an amount sufficient to reduce the biological activity of, cancer or an HIV-1, HIV-2, HCV, Norovirus, Saporovirus, HSV-1, HSV-2 Dengue virus, Yellow fever, or HBV infection. The pharmaceutical compositions include one or more of the compounds described herein, in combination with a pharmaceutically acceptable carrier or excipient, for treating a host with cancer or infected with HIV-1, HIV-2, HCV, Norovirus, Saporovirus, HSV-1, HSV-2, Dengue virus, Yellow fever, or HBV. The formulations can further include at least one further therapeutic agent. In addition, the present invention includes processes for preparing such compounds.

As with Hepatitis C replicons, Norovirus replicons require viral helicase, protease, and polymerase to be functional in order for replication of the replicon to occur. The replicons can be used in high throughput assays, which evaluate whether a compound to be screened for activity inhibits the ability of Norovirus helicase, protease, and/or polymerase to function, as evidenced by an inhibition of replication of the replicon.

The compounds are monophosphate or monophosphonate forms of various 6-substituted-2-amino purine nucleosides, or analogs of the monophosphate forms, which also become triphosphorylated when administered in vivo. We have discovered, quite surprisingly, that preparation of the monophosphate prodrug forms of these nucleosides protects the 6-position substituent from conversion to the G analog. By preparing the monophosphate prodrugs, we have developed a method for delivering nucleotide triphosphates to the polymerase or reverse transcriptase, which before this invention was not possible, or at least not possible at therapeutically-relevant concentrations. This invention allows for a new and novel series of nucleotide triphosphates to be prepared in vivo and enlisted as antiviral agents or anticancer agents.

The compounds described herein include monophosphate, phosphonate, and other analogs of β-D and β-L-6-substituted-2-amino purine nucleosides. In one embodiment, the active compound is of formula (I):

(I)

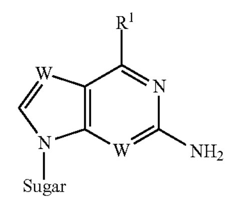

or a pharmaceutically acceptable salt or prodrug thereof, wherein:

i) $R^1$ is an atom or group removed in vivo to form OH when administered as the parent nucleoside, for example, halogen (F, Cl, Br, I), OR', $N(R')_2$, SR', OCOR', NHCOR', N(COR')COR', SCOR', OCOOR', and NHCOOR'.

each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above, for example, hydroxyalkyl, aminoalkyl, and alkoxyalkyl.

ii) W is, independently, N, CH, CF, CCN, CC≡CH, or $CC(O)N(R')_2$;

iii) Sugar is ribose or modified ribose of the general formula (II):

(II)

wherein:

Y is O or S;

Z is selected from the group consisting of $CL_2$, $CL_2CL_2$, $CL_2OCL_2$, $CL_2SCL_2$, $CL_2O$, $OCL_2$ and $CL_2NHCL_2$, wherein L independently is selected from the group consisting of H, F, alkyl, alkenyl, and alkynyl, wherein alkyl, alkenyl, and alkynyl may each optionally contain one or more heteroatoms;

A is O, S, $CH_2$, CHF, $CF_2$, C═$CH_2$, C═CHF, or C═$CF_2$;

$R^{4'}$, $R^5$, $R^{5'}$, $R^6$, $R^{6'}$, and $R^{7'}$ are independently selected from the group consisting of H, F, Cl, Br, I, OH, SH, $NH_2$, NHOH, $NHNH_2$, $N_3$, C(O)OH, CN, $C(O)NH_2$, $C(S)NH_2$, C(O)OR, R, OR, SR, SSR, NHR, and $NR_2$;

wherein for formula (I) where sugar is formula (II), when A is O, and $R^{4'}$, $R^5$, $R^{5'}$, $R^6$, $R^{7'}$ are H, $R^{6'}$ cannot be $N_3$;

wherein for formula (I) where sugar is formula (II), when A is O or S $R^{7'}$ cannot be OH, SH, $NH_2$, NHOH, $NHNH_2$, OR, SR, SSR, NHR, and $NR_2$;

R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl.

$R^2$ and $R^3$, when administered in vivo, are ideally capable of providing the nucleoside monophosphate monophosphonate, thiomonophosphonate, or thiomonophosphate. Representative $R^2$ and $R^3$ are independently selected from:

(a) $OR^8$ where $R^8$ is H, $C_{1-20}$ alkyl, $C_{3-6}$ cycloalkyl, $C_{1-6}$ haloalkyl, aryl, or heteroaryl which includes, but is not limited to, phenyl or naphthyl optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{9a}$, halogen, $C_{1-6}$ haloalkyl, —$N(R^{9a})_2$, $C_{1-6}$ acylamino, —$NHSO_2C_{1-6}$ alkyl, —$SO_2N(R^{9a})_2$, —$SO_2C_{1-6}$ alkyl, $COR^{9b}$, nitro and cyano;

$R^{9a}$ is independently H or $C_{1-6}$ alkyl;

$R^{9b}$ is —$OR^{9a}$ or —$N(R^{9a})_2$;

(b)

where $R^{10a}$ and $R^{10b}$ are:

(i) independently selected from the group consisting of H, $C_{1-10}$ alkyl, —$(CH_2)_rNR^{9a}{}_2$, $C_{1-6}$ hydroxyalkyl, —$CH_2SH$, —$(CH_2)_2S(O)_pMe$, —$(CH_2)_3NHC(═NH)NH_2$, (1H-indol-3-yl)methyl, (1H-imidazol-4-yl)methyl, —$(CH_2)_mCOR^{9b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;

(ii) $R^{10a}$ is H and $R^{10b}$ and $R^{12}$ together are $(CH_2)_{2-4}$ to form a ring that includes the adjoining N and C atoms;

(iii) $R^{10a}$ and $R^{10b}$ together are $(CH_2)_n$ to form a ring;

(iv) $R^{10a}$ and $R^{10b}$ both are $C_{1-6}$ alkyl; or (v) $R^{10a}$ is H and $R^{10b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2-$ $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;
r is 1 to 6;
n is 4 or 5;
m is 0 to 3;

$R^{11}$ is H, $C_{1-10}$ alkyl, or $C_{1-10}$ alkyl substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

$R^{12}$ is H, $C_{1-3}$ alkyl, or $R^{10a}$, or $R^{10b}$ and $R^{12}$ together are $(CH_2)_{2-4}$ so as to form a ring that includes the adjoining N and C atoms;

(c) an O attached lipid (including a phospholipid), an N or O attached peptide, an O attached cholesterol, or an O attached phytosterol;

(d) $R^2$ and $R^3$ may come together to form a ring

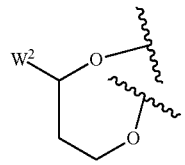

where $W^2$ is selected from a group consisting of phenyl or monocyclic heteroaryl, optionally substituted with one to three substituents independently selected from the group consisting of $C_{1-6}$ alkyl, $CF_3$, $C_{2-6}$ alkenyl, $C_{1-6}$ alkoxy, $OR^{9c}$, $CO_2R^{9a}$, $COR^{9a}$, halogen, $C_{1-6}$ haloalkyl, $-N(R^{9a})_2$, $C_{1-6}$ acylamino, $CO_2N(R^{9a})_2$, $SR^{9a}$, $-NHSO_2C_{1-6}$ alkyl, $-SO_2N(R^{9a})_2$, $-SO_2C_{1-6}$ alkyl, $COR^{9b}$, and cyano, and wherein said monocyclic heteroaryl and substituted monocyclic heteroaryl has 1-2 heteroatoms that are independently selected from the group consisting of N, O, and S with the provisos that:

a) when there are two heteroatoms and one is O, then the other can not be O or S, and
b) when there are two heteroatoms and one is S, then the other can not be O or S;

$R^{9a}$ is independently H or $C_{1-6}$ alkyl;
$R^{9b}$ is $-OR^{9a}$ or $-N(R^{9a})_2$;
$R^{9c}$ is H or $C_{1-6}$ acyl;

(e) 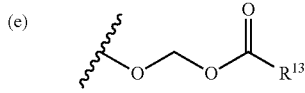

where $R^{13}$ is selected from a group consisting of H, $C_{1-10}$ alkyl, $C_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

f) $R^2$ and $R^3$ may come together to form a ring

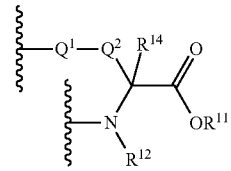

where $R^{14}$ is: (i) independently selected from the group consisting of H, $C_{1-10}$ alkyl, $-(CH_2)_rNR_2^{9a}$, $C_{1-6}$ hydroxyalkyl, $-CH_2SH$, $-(CH_2)_2S(O)_pMe$, $-(CH_2)_3NHC(=NH)NH_2$, (1H-indol-3-yl)methyl, (1H-imidazol-4-yl)methyl; $-(CH_2)_mCOR^{9b}$, aryl and aryl-$C_{1-3}$ alkyl or heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen, nitro, and cyano; (ii) $R^{14}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;
r is 1 to 6;
m is 0 to 3
$Q^1$ is $NR^{9a}$, O, or S
$Q^2$ is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, fluoro, and chloro;
$R^{11}$ is H, $C_{1-10}$ alkyl, $C_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;
$R^{12}$ is H, or $C_{1-3}$ alkyl, or $R^{14b}$ and $R^{12}$ together are $(CH_2)_{2-4}$ so as to form a ring that includes the adjoining N and C atoms;

iv) alternatively Sugar is a modified ribose of the general formula (III):

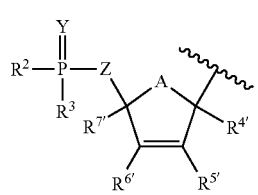

(III)

wherein:
A, $R^2$, $R^3$, Y, Z, $R^{4'}$, $R^{5'}$, $R^{6'}$, and $R^{7'}$ are as defined above;
wherein for formula (I) where sugar is formula (III), when A is O or S $R^{7'}$ cannot be OH, SH, $NH_2$, NHOH, $NHNH_2$, OR, SR, SSR, NHR, and $NR_2$ R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl.

v) alternatively Sugar is a dioxolane or a oxathiolane of the general formulas (IV), (V), (VI), and (VII):

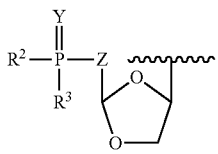
(IV)

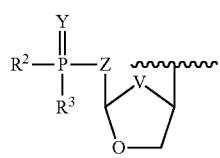
(V)

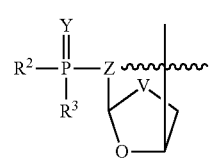
(VI)

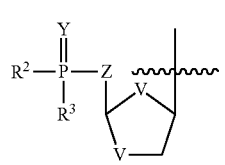
(VII)

wherein:

V is S or Se $R^2$, $R^3$, Y, and Z are as defined above vi) alternatively Sugar is a phosphonylmethoxyalkyl of the general formula (VIII):

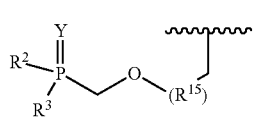
(VIII)

wherein:

$R^2$, $R^3$, and Y are as defined above;

$R^{15}$ is selected from the group consisting of alkyl (including but not limited to $C_1$-$C_6$), alkenyl (including but not limited to $C_2$-$C_6$), and alkynyl (including but not limited to $C_2$-$C_6$), cycloalkyl (including but not limited to $C_3$-$C_8$), aryl (including but not limited to $C_6$-$C_{10}$), heteroaryl (including but not limited to $C_6$-$C_{10}$), arylalkyl, and alkylaryl;

vii) alternatively Sugar is of the general formulas (IX) or (X):

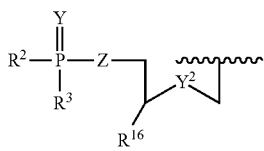
(IX)

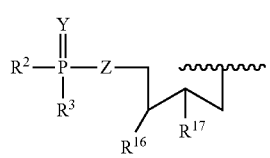
(X)

wherein:

$R^2$, $R^3$, and Y are as defined above;

$Y^2$ is O, S, Se NR;

R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl;

$R^{16}$ and $R^{17}$ are defined as H, $CH_3$, $CH_2OR^{18}$;

$R^{18}$ is H or lower acyl ($C_1$-$C_6$)

viii) alternatively Sugar is a modified ribose of the general formulas (XI):

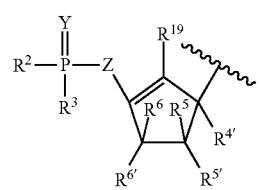
(XI)

wherein:

$R^2$, $R^3$, and Y are as defined above;

$R^{4'}$, $R^5$, $R^{5'}$, $R^6$, and $R^{6'}$ are as defined above;

$R^{19}$ is H, F, Cl, Br, I, $N_3$, C(O)OH, CN, C(O)$NH_2$, C(S)$NH_2$, C(O)OR, R

R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl.

In one embodiment of the invention, the active compound is of formula (I) where $R^{6'}$ selected from the group consisting of H, F, Cl, Br, I, OH, SH, $NH_2$, NHOH, $NHNH_2$, C(O)OH, CN, C(O)$NH_2$, C(S)$NH_2$, C(O)OR, R, OR, SR, SSR, NHR, and $NR_2$;

In another embodiment of the invention, the active compound is of formulas (XII), (XIII), or (XIV):

(XII)
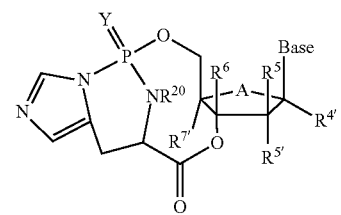

(XIII)
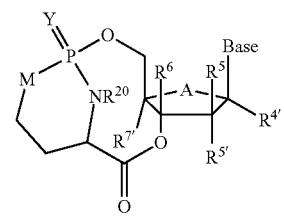

(XIV)
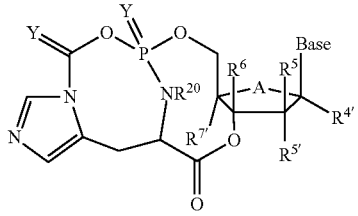

or a pharmaceutically acceptable salt or prodrug thereof, wherein:

$R^{4'}$, $R^5$, $R^{5'}$, $R^6$, Y, A, and $R^{7'}$ are as defined above;
$R^{20}$ is lower alkyl ($C_1$-$C_6$ alkyl);
M is O, S, or NR;
  R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl;
Base is chosen from:

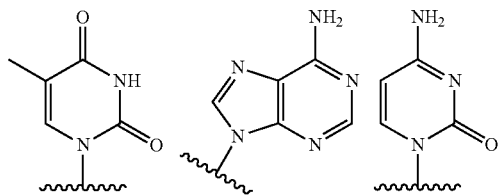

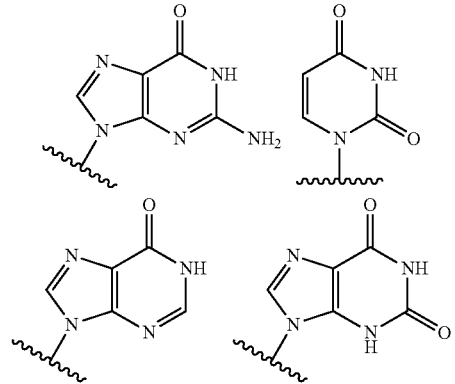

-continued

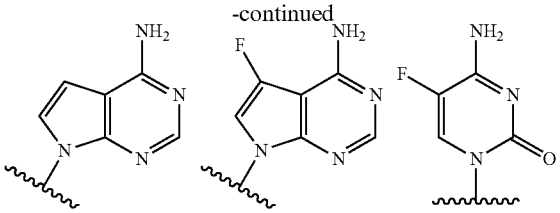

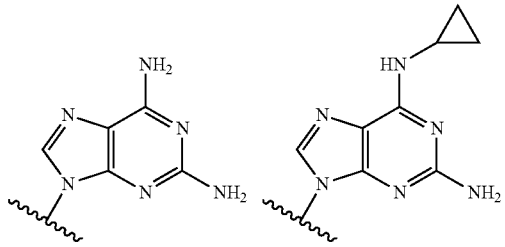

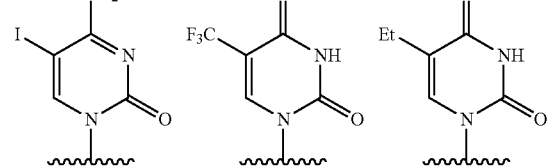

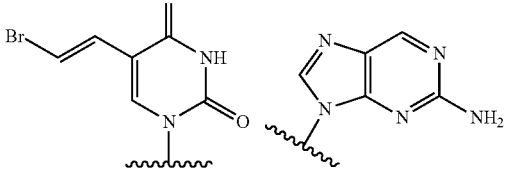

In another embodiment of the invention, the active compound is of formulas (XV) or (XVI):

(XV)
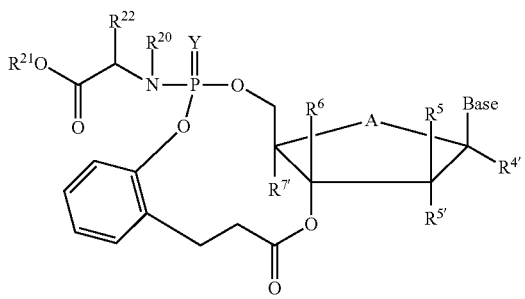

(XVI)
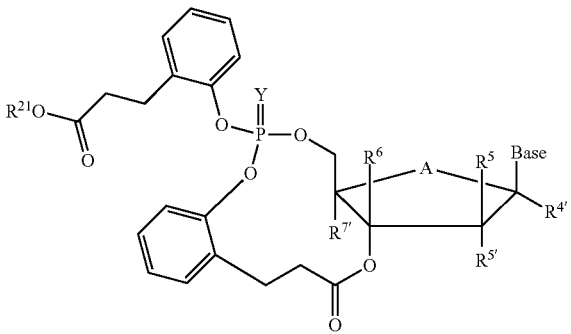

or a pharmaceutically acceptable salt or prodrug thereof, wherein:

$R^{4'}$, $R^5$, $R^{5'}$, $R^6$, Y, A, $R^{7'}$, $R^{20}$ and Base are as defined above;

$R^{21}$ is H, $C_{1-10}$ alkyl, $C_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

$R^{22}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

In another embodiment of the invention, the active compound is of formulas (XVII) or (XVIII):

(XVII)

(XVIII)

wherein:

$R^{4'}$, $R^5$, $R^{5'}$, $R^6$, Y, M, $R^{7'}$, $R^{20}$, $R^{21}$, $R^{22}$, and Base are as defined above;

The compounds described herein can be in the form of the β-L- or β-D-configuration, or a mixture thereof, including a racemic mixture thereof.

The compounds can be prepared, for example, by preparing the 5'-OH analogs, then converting these to the monophosphates, phosphonate, or other analogs.

In addition, the compounds described herein are inhibitors of HIV-1, HIV-2, HCV, Norovirus, Saporovirus, HSV-1, HSV-2, Dengue virus, Yellow fever, cancer, and/or HBV. Therefore, these compounds can also be used to treat patients that are co-infected with both HIV-1, HIV-2, HCV, Norovirus, Saporovirus, HSV-1, HSV-2, Dengue virus, Yellow fever, cancer, and/or HBV.

BRIEF DESCRIPTION OF THE FIGURES

FIG. 12: is a graphic representation of the genotypes of xxLAI viruses.

DETAILED DESCRIPTION

Figure 1:
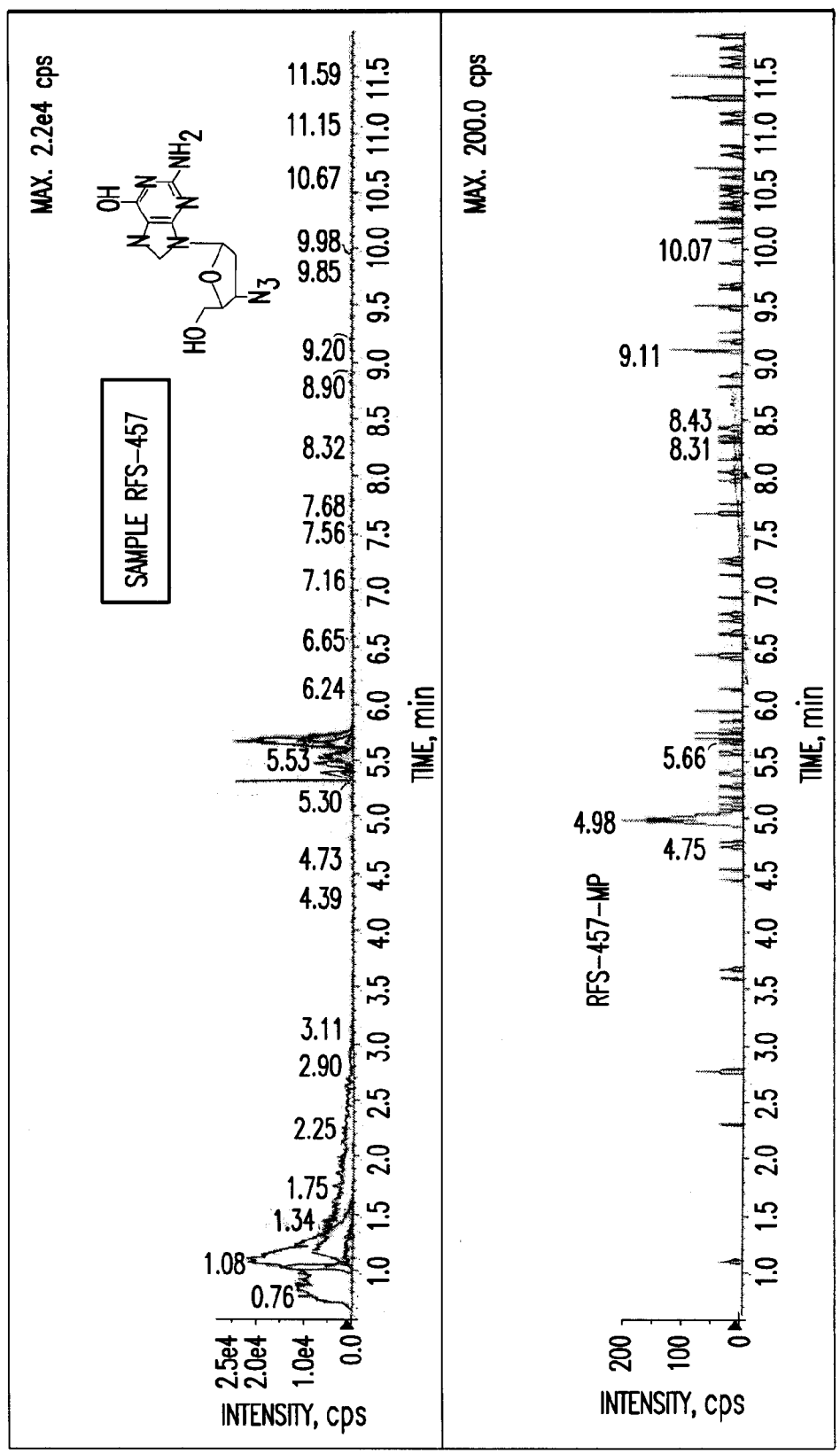
FIG. 1: LC/MS analysis of nucleotides formed after 4 hr incubation in human peripheral blood mononuclear (PBM) cells of 50 μM RS-457.
Figure 1:
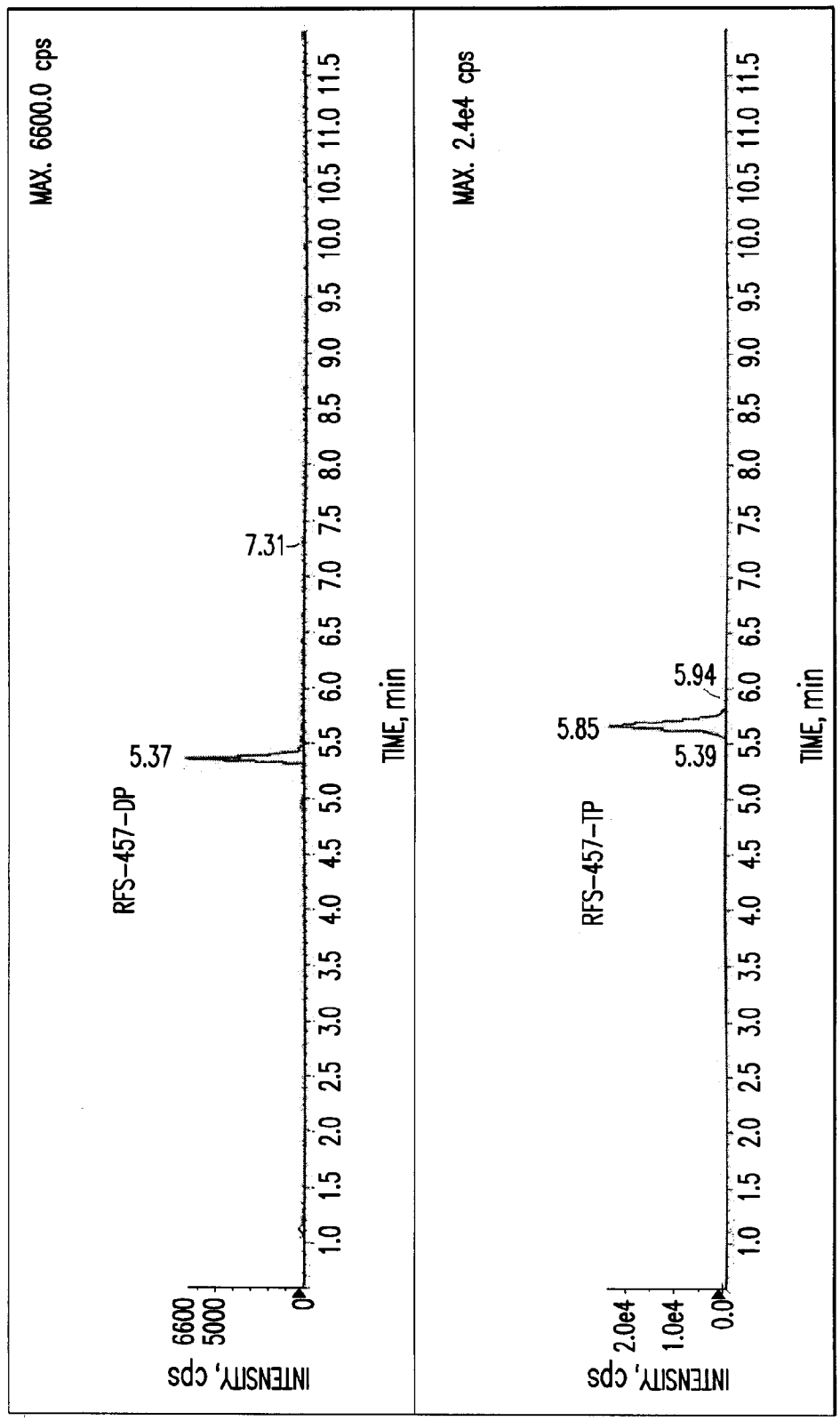

The 6-substituted-2-amino purine nucleotides monophosphate prodrugs described herein show inhibitory activity against HIV, HCV, Norovirus, Saporovirus, HSV-1, HSV-2, Dengue virus, Yellow fever, cancer, and HBV. Therefore, the compounds can be used to treat or prevent a viral infection in a host, or reduce the biological activity of the virus. The host can be a mammal, and in particular, a human, infected with HIV-1, HIV-2, HCV, Norovirus, Saporovirus, HSV-1, HSV-2, Dengue virus, Yellow fever, cancer, and/or HBV. The methods involve administering an effective amount of one or more of the 6-substituted-2-amino purine nucleotides monophosphate prodrugs described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The terms "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a nucleotide composition that comprises at least approximately 95%, and, preferably, approximately 97%, 98%, 99% or 100% of a single enantiomer of that nucleotide.

As used herein, the term "substantially free of" or "substantially in the absence of" refers to a nucleotide composition that includes at least 85 to 90% by weight, preferably 95% to 98% by weight, and, even more preferably, 99% to 100% by weight, of the designated enantiomer of that nucleotide. In a preferred embodiment, the compounds described herein are substantially free of enantiomers.

Similarly, the term "isolated" refers to a nucleotide composition that includes at least 85 to 90% by weight, preferably 95% to 98% by weight, and, even more preferably, 99% to 100% by weight, of the nucleotide, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$ In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and "cycloheteroalkyl" refer to a nonaromatic cyclic group, for example, including between 3 and 10 atoms in the ring, wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "peptide" refers to a various natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester, phosphate ester, salt of an ester or a related group) of a nucleotide compound which, upon administration to a patient, provides the nucleotide monophosphate compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

Prodrugs also include amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterized by side-chain branching adjacent to the α-carbon atom, which showed improved bioavailability after oral administration compared with the alanine and glycine esters). A process for preparing such amino acid esters is disclosed in U.S. Pat. No. 4,957,924 (Beauchamp), the text of which is incorporated by reference. As an alternative to the use of valine itself, a functional equivalent of the amino acid can be used (e.g., an acid halide such as the acid chloride, or an acid anhydride). In such a case, to avoid undesirable side-reactions, it may be advantageous to use an amino-protected derivative.

II. Active Compound

In one embodiment of the invention, the active compound is of formula (I):

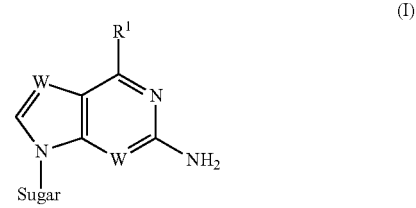

(I)

or a pharmaceutically acceptable salt or prodrug thereof, wherein:

iii) $R^1$ is an atom or group removed in vivo to form OH when administered as the parent nucleoside, for example, halogen (F, Cl, Br, I), OR', N(R')$_2$, SR', OCOR', NHCOR', N(COR')COR', SCOR', OCOOR', and NHCOOR'.

each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above, for example, hydroxyalkyl, aminoalkyl, and alkoxyalkyl.

iv) W is, independently, N, CH, CF, CCN, CC≡CH, or CC(O)N(R')$_2$;
ix) Sugar is ribose or modified ribose of the general formula (II):

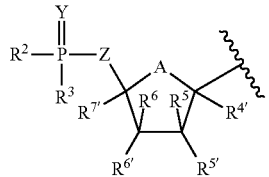

(II)

wherein:
Y is O or S;
Z is selected from the group consisting of CL$_2$, CL$_2$CL$_2$, CL$_2$OCL$_2$, CL$_2$SCL$_2$, CL$_2$O, OCL$_2$ and CL$_2$NHCL$_2$, wherein L independently is selected from the group consisting of H, F, alkyl, alkenyl, and alkynyl, wherein alkyl, alkenyl, and alkynyl may each optionally contain one or more heteroatoms;
A is O, S, CH$_2$, CHF, CF$_2$, C=CH$_2$, C=CHF, or C=CF$_2$;
R$^{4'}$, R$^5$, R$^{5'}$, R$^6$, R$^{6'}$, and R$^{7'}$ are independently selected from the group consisting of H, F, Cl, Br, I, OH, SH, NH$_2$, NHOH, NHNH$_2$, N$_3$, C(O)OH, CN, C(O)NH$_2$, C(S)NH$_2$, C(O)OR, R, OR, SR, SSR, NHR, and NR$_2$;
wherein for formula (I) where sugar is formula (II), when A is O, and R$^{4'}$, R$^5$, R$^{5'}$, R$^6$, R$^{7'}$ are H, R$^{6'}$ cannot be N$_3$;
wherein for formula (I) where sugar is formula (II), when A is O or S R$^{7'}$ cannot be OH, SH, NH$_2$, NHOH, NHNH$_2$, OR, SR, SSR, NHR, and NR$_2$;
R is independently a lower alkyl (C$_1$-C$_6$ alkyl), lower alkenyl, lower alkynyl, lower cycloalkyl (C$_3$-C$_6$ cycloalkyl) aryl, alkylaryl, or arylalkyl, wherein the groups can be substituted with one or more substituents as defined above, for example, hydroxyalkyl, aminoalkyl, and alkoxyalkyl.
R$^2$ and R$^3$, when administered in vivo, are ideally capable of providing the nucleoside monophosphate monophosphonate, thiomonophosphonate, or thiomonophosphate. Representative R$^2$ and R$^3$ are independently selected from:
(a) OR$^8$ where R$^8$ is H, C$_{1-20}$ alkyl, C$_{3-6}$ cycloalkyl, C$_{1-6}$ haloalkyl, aryl, or heteroaryl which includes, but is not limited to, phenyl or naphthyl optionally substituted with one to three substituents independently selected from the group consisting of C$_{1-6}$ alkyl, C$_{2-6}$ alkenyl, C$_{2-6}$ alkynyl, C$_{1-6}$ alkoxy, (CH$_2$)$_{1-6}$CO$_2$R$^{9a}$, halogen, C$_{1-6}$ haloalkyl, —N(R$^{9a}$)$_2$, C$_{1-6}$ acylamino, —NHSO$_2$C$_{1-6}$ alkyl, —SO$_2$N(R$^{9a}$)$_2$, —SO$_2$C$_{1-6}$ alkyl, COR$^{9b}$, nitro and cyano;
R$^{9a}$ is independently H or C$_{1-6}$ alkyl;
R$^{9b}$ is —OR$^{9a}$ or —N(R$^{9a}$)$_2$;

(b) 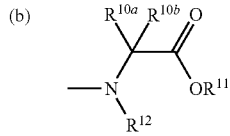

where R$^{10a}$ and R$^{10b}$ are:
(i) independently selected from the group consisting of H, C$_{1-10}$ alkyl, —(CH$_2$)$_r$NR$^{9a}$$_2$, C$_{1-6}$ hydroxyalkyl, —CH$_2$SH, —(CH$_2$)$_2$S(O)$_p$Me, —(CH$_2$)$_3$NHC(=NH)NH$_2$, (1H-indol-3-yl)methyl, (1H-imidazol-4-yl)methyl, —(CH$_2$)$_m$COR$^{9b}$, aryl and aryl-C$_{1-3}$ alkyl, said aryl groups optionally substituted with a group selected from the group consisting of hydroxyl, C$_{1-10}$ alkyl, C$_{1-6}$ alkoxy, halogen, nitro, and cyano;
(ii) R$^{10a}$ is H and R$^{10b}$ and R$^{12}$ together are (CH$_2$)$_{2-4}$ to form a ring that includes the adjoining N and C atoms;
(iii) R$^{10a}$ and R$^{10b}$ together are (CH$_2$)$_n$ to form a ring;
(iv) R$^{10a}$ and R$^{10b}$ both are C$_{1-6}$ alkyl; or
(v) R$^{10a}$ is H and R$^{10b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$—CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl;
p is 0 to 2;
r is 1 to 6;
n is 4 or 5;
m is 0 to 3;
R$^{11}$ is H, C$_{1-10}$ alkyl, or C$_{1-10}$ alkyl substituted with a lower alkyl, alkoxy, di(lower alkyl)-amino, fluoro, C$_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are C$_{1-5}$ alkyl, or C$_{1-5}$ alkyl substituted with a lower alkyl, alkoxy, di(lower alkyl)-amino, fluoro, C$_{3-10}$ cycloalkyl, or cycloalkyl;
R$^{12}$ is H, C$_{1-3}$ alkyl, or R$^{10a}$, or R$^{10b}$ and R$^{12}$ together are (CH$_2$)$_{2-4}$ so as to form a ring that includes the adjoining N and C atoms;
(c) an O attached lipid (including a phospholipid), an N or O attached peptide, an O attached cholesterol, or an O attached phytosterol;
(d) R$^2$ and R$^3$ may come together to form a ring

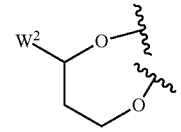

where W$^2$ is selected from a group consisting of phenyl or monocyclic heteroaryl, optionally substituted with one to three substituents independently selected from the group consisting of C$_{1-6}$ alkyl, CF$_3$, C$_{2-6}$ alkenyl, C$_{1-6}$ alkoxy, OR$^{9c}$, CO$_2$R$^{9a}$, COR$^{9a}$, halogen, C$_{1-6}$ haloalkyl, —N(R$^{9a}$)$_2$, C$_{1-6}$ acylamino, CO$_2$N(R$^{9a}$)$_2$, SR$^{9a}$, —NHSO$_2$C$_{1-6}$ alkyl, —SO$_2$N(R$^{9a}$)$_2$, —SO$_2$C$_{1-6}$ alkyl, COR$^{9b}$, and cyano, and wherein said monocyclic heteroaryl and substituted monocyclic heteroaryl has 1-2 heteroatoms that are independently selected from the group consisting of N, O, and S with the provisos that:
a) when there are two heteroatoms and one is O, then the other can not be O or S, and
b) when there are two heteroatoms and one is S, then the other can not be O or S;
R$^{9a}$ is independently H or C$_{1-6}$ alkyl;
R$^{9b}$ is —OR$^{9a}$ or —N(R$^{9a}$)$_2$;
R$^{9c}$ is H or C$_{1-6}$ acyl;

(e) 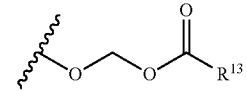

where R$^{13}$ is selected from a group consisting of H, C$_{1-10}$ alkyl, C$_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

f) $R^2$ and $R^3$ may come together to form a ring

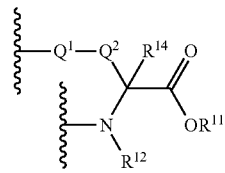

where $R^{14}$ is: (i) independently selected from the group consisting of H, $C_{1-10}$ alkyl, —$(CH_2)_rNR_2^{9a}$, $C_{1-6}$ hydroxyalkyl, —$CH_2SH$, —$(CH_2)_2S(O)_pMe$, —$(CH_2)_3NHC(=NH)NH_2$, (1H-indol-3-yl)methyl, (1H-imidazol-4-yl)methyl, —$(CH_2)_mCOR^{9b}$, aryl and aryl-$C_{1-3}$ alkyl or heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen, nitro, and cyano; (ii) $R^{14}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;
r is 1 to 6;
m is 0 to 3
$Q^1$ is $NR^{9a}$, O, or S
$Q^2$ is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, fluoro, and chloro;
$R^{11}$ is H, $C_{1-10}$ alkyl, $C_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;
$R^{12}$ is H, or $C_{1-3}$ alkyl, or $R^{14b}$ and $R^{12}$ together are $(CH_2)_{2-4}$ so as to form a ring that includes the adjoining N and C atoms;

x) alternatively Sugar is a modified ribose of the general formula (III):

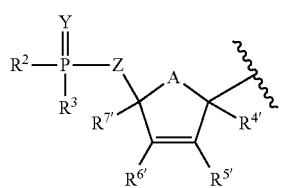

wherein:

$A, R^2, R^3, Y, Z, R^{4'}, R^{5'}, R^{6'}$, and $R^{7'}$ are as defined above;

wherein for formula (I) where sugar is formula (III), when A is O or S $R^{7'}$ cannot be OH, SH, $NH_2$, NHOH, $NHNH_2$, OR, SR, SSR, NHR, and $NR_2$ R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl.

xi) alternatively Sugar is a dioxolane or a oxathiolane of the general formulas (IV), (V), (VI), and (VII):

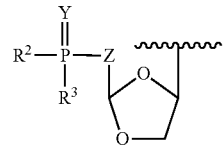

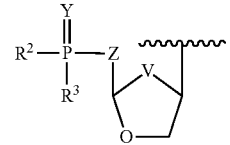

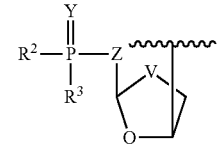

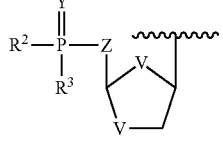

wherein:

V is S or Se $R^2, R^3, Y$, and Z are as defined above xii) alternatively Sugar is a phosphonylmethoxyalkyl of the general formula (VIII):

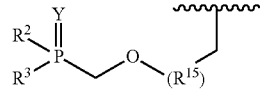

wherein:

$R^2, R^3$, and Y are as defined above;

$R^{15}$ is selected from the group consisting of alkyl (including but not limited to $C_1$-$C_6$), alkenyl (including but not limited to $C_2$-$C_6$), and alkynyl (including but not limited to $C_2$-$C_6$), cycloalkyl (including but not limited to $C_3$-$C_8$), aryl (including but not limited to $C_6$-$C_{10}$), heteroaryl (including but not limited to $C_6$-$C_{10}$), arylalkyl, and alkylaryl;

xiii) alternatively Sugar is of the general formulas (IX) or (X):

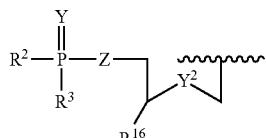
(IX)

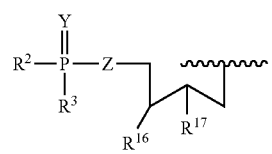
(X)

wherein:
$R^2$, $R^3$, and Y are as defined above;
$Y^2$ is O, S, Se NR;
R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl;
$R^{16}$ and $R^{17}$ are defined as H, $CH_3$, $CH_2OR^{18}$;
$R^{18}$ is H or lower acyl ($C_1$-$C_6$)

xiv) alternatively Sugar is a modified ribose of the general formulas (XI):

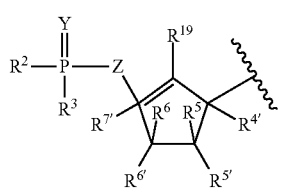
(XI)

wherein:
$R^2$, $R^3$, and Y are as defined above;
$R^{4'}$, $R^5$, $R^{5'}$, $R^6$, and $R^{6'}$ are as defined above;
$R^{19}$ is H, F, Cl, Br, I, $N_3$, C(O)OH, CN, C(O)$NH_2$, C(S)$NH_2$, C(O)OR, R
R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl.

In one embodiment of the invention, the active compound is of formula (I) where $R^{6'}$ selected from the group consisting of H, F, Cl, Br, I, OH, SH, $NH_2$, NHOH, $NHNH_2$, C(O)OH, CN, C(O)$NH_2$, C(S)$NH_2$, C(O)OR, R, OR, SR, SSR, NHR, and $NR_2$;

In another embodiment of the invention, the active compound is of formulas (XII), (XIII), or (XIV):

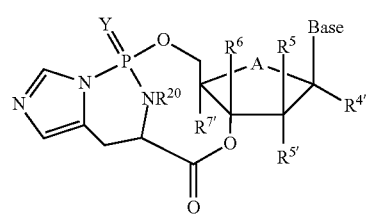
(XII)

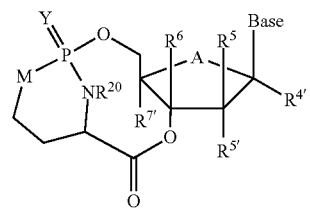
(XIII)

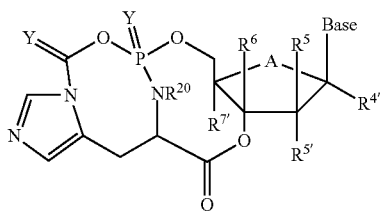
(XIV)

or a pharmaceutically acceptable salt or prodrug thereof, wherein:
$R^{4'}$, $R^5$, $R^{5'}$, $R^6$, Y, A, and $R^{7'}$ are as defined above;
$R^{20}$ is lower alkyl ($C_1$-$C_6$ alkyl);
M is O, S, or NR;
R is independently a lower alkyl ($C_1$-$C_6$ alkyl), lower alkenyl, lower alkynyl, lower cycloalkyl ($C_3$-$C_6$ cycloalkyl) aryl, alkylaryl, or arylalkyl, wherein the groups can be substituted with one or more substituents as defined above, for example, hydroxyalkyl, aminoalkyl, and alkoxyalkyl;

Base is chosen from:

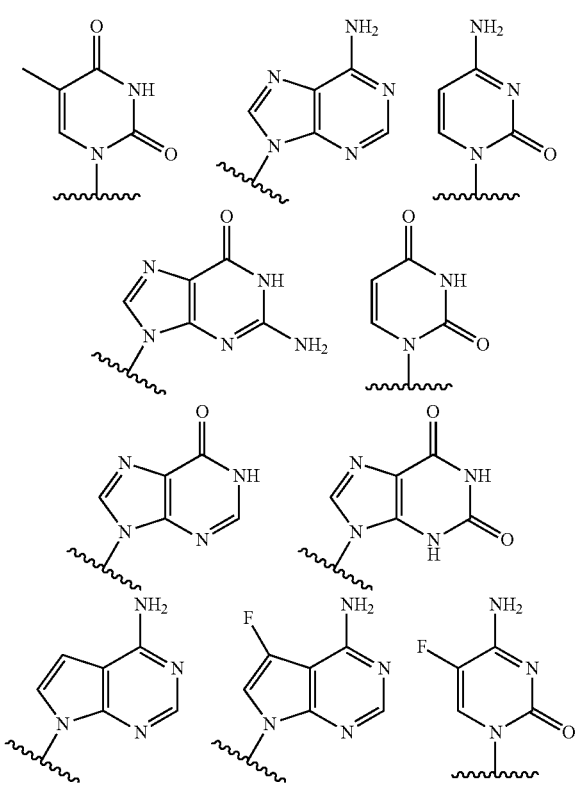

-continued

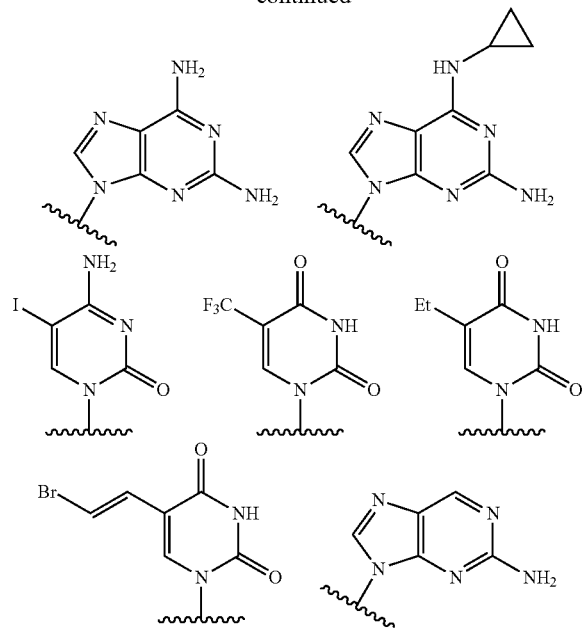

In another embodiment of the invention, the active compound is of formulas (XV) or (XVI):

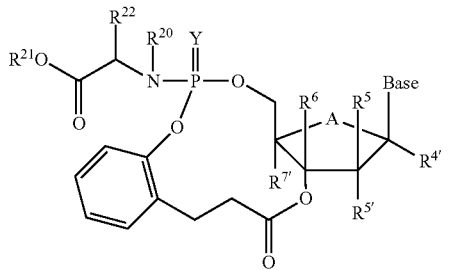
(XV)

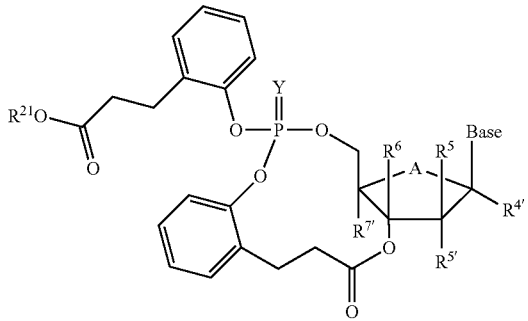
(XVI)

or a pharmaceutically acceptable salt or prodrug thereof, wherein:
$R^{4'}, R^5, R^{5'}, R^6, Y, A, R^{7'}, R^{20}$ and Base are as defined above;
$R^{21}$ is H, $C_{1-10}$ alkyl, $C_{1-10}$ alkyl optionally substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

$R^{22}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2OH$, $CH(OH)CH_3$, $CH_2((4'-OH)-Ph)$, $CH_2SH$, or lower cycloalkyl;

In another embodiment of the invention, the active compound is of formulas (XVII) or (XVIII):

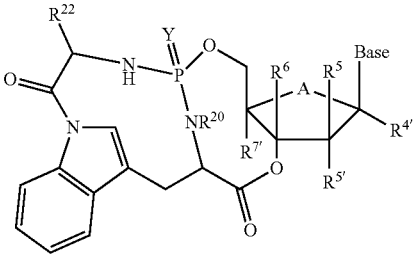
(XVII)

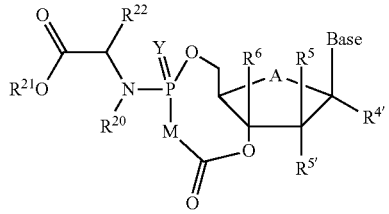
(XVIII)

or a pharmaceutically acceptable salt or prodrug thereof, wherein:
$R^{4'}, R^5, R^{5'}, R^6, Y, M, R^{7'}, R^{20}, R^{21}, R^{22}$, and Base are as defined above;

The compounds described herein can be in the form of the β-L- or β-D-configuration, or a mixture thereof, including a racemic mixture thereof.

III. Stereoisomerism And Polymorphism

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective nucleoside, then derivatize the nucleoside to form the compounds described herein, or purify the nucleotides themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

The nucleotide prodrugs described herein can be administered to additionally increase the activity, bioavailability, stability or otherwise alter the properties of the nucleotide monophosphate.

A number of nucleotide prodrug ligands are known. In general, alkylation, acylation or other lipophilic modification of the monophosphate or other anolog of the nucleoside will increase the stability of the nucleotide.

Examples of substituent groups that can replace one or more hydrogens on the monophosphate moiety are alkyl, aryl, steroids, carbohydrates, including but not limited to sugars, 1,2-diacylglycerol and alcohols. Many are described in R. Jones & N. Bischofberger, *Antiviral Research,* 1995, 27, 1-17 and S. J. Hecker & M. D. Erion, *J. Med. Chem.,* 2008, 51, 2328-2345. Any of these can be used in combination with the disclosed nucleotides to achieve a desired effect.

The active nucleotide can also be provided as a 5'-phosphoether lipid as disclosed in the following references, which are incorporated by reference: Kucera, L. S., N. Iyer, E. Leake, A. Raben, Modest E. K., D. L. W., and C. Piantadosi, "Novel membrane-interactive ether lipid analogs that inhibit infectious HIV-1 production and induce defective virus formation," *AIDS Res. Hum. Retroviruses,* 1990, 6, 491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest, "Synthesis and evaluation of novel ether lipid nucleoside conjugates for anti-HIV activity," *J. Med. Chem.,* 1991, 34, 1408-14; Hostetler, K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine," *Antimicrob. Agents Chemother.,* 1992, 36, 2025-29; Hostetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.*, 1990, 265, 61127.

Nonlimiting examples of US patents that disclose suitable lipophilic substituents that can be covalently incorporated into the nucleoside, preferably at $R^2$ and/or $R^3$ position of the nucleotides described herein, or lipophilic preparations, include U.S. Pat. Nos. 5,149,794 (Yatvin et al.); 5,194,654 (Hostetler et al.), 5,223,263 (Hostetler et al.); 5,256,641 (Yatvin et al.); 5,411,947 (Hostetler et al.); 5,463,092 (Hostetler et al.); 5,543,389 (Yatvin et al.); 5,543,390 (Yatvin et al.); 5,543,391 (Yatvin et al.); and 5,554,728 (Basava et al.), all of which are incorporated by reference. Foreign patent applications that disclose lipophilic substituents that can be attached to nucleosites of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. Methods of Treatment

Hosts, including but not limited to humans, infected with HIV-1, HIV-2, HBV, HCV, Norovirus, Saporovirus, HSV-1, HSV-2, Dengue virus, yellow fever, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The compounds can also be used to treat cancer. Patients that can be treated with the compounds described herein, and the pharmaceutically acceptable salts and prodrugs of these compounds, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a method of and to a pharmaceutical composition for inhibiting abnormal cellular proliferation in a patient which comprises an amount of a compound described herein, or a pharmaceutically acceptable salt or prodrug thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula I and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The compounds described herein can also be used with signal transduction inhibitors, such as agents that can inhibit EGFR (epidermal growth factor receptor) responses, such as EGFR antibodies, EGF antibodies; and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 (Pfizer Inc., N.Y.), AG-13736 (Agouron Pharmaceuticals, Inc. a Pfizer Company), SU-5416 and SU-6668 (Sugen Inc. of South San Francisco, Calif., USA), and SH-268 (Schering) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP-358,774 (OSI-774) (Tarceva) (OSI Pharmaceuticals, Inc.), GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117, 341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds described herein in accordance with the present invention.

The compounds can also be used with other agents useful in treating abnormal cellular proliferation or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

Other anti-angiogenesis agents, including, but not limited to, other COX-II inhibitors, other MMP inhibitors, other anti-VEGF antibodies or inhibitors of other effectors of vascularization can also be used.

The compounds and pharmaceutical compositions described herein can be used to treat or prevent an infection by one or more Noroviruses, as well as other viruses in the Caliciviridae taxonomic family.

In therapeutic use for treating Norovirus infection, the compounds and/or compositions can be administered to patients diagnosed with Norovirus infection at dosage levels suitable to achieve therapeutic benefit. By "therapeutic benefit," and grammatical equivalents, is meant the administration of the compound leads to a beneficial effect in the patient over time. For example, therapeutic benefit can be achieved when the Norovirus titer or viral load in a patient is either reduced or stops increasing.

Therapeutic benefit also can be achieved if the administration of a compound slows or halts altogether the onset of adverse symptoms that typically accompany Norovirus infections, regardless of the Norovirus titer or viral load in the patient. The compounds and/or compositions described herein may also be administered prophylactically in patients who are at risk of developing Norovirus infection, or who have been exposed to Norovirus, to prevent the development of Norovirus infection. For example, the compounds and/or compositions thereof may be administered to patients likely to have been exposed to Norovirus.

Outbreaks of norovirus disease often occur in closed or semi-closed communities, such as long-term care facilities, hospitals, prisons, and cruise ships where once the virus has been introduced, the infection spreads very rapidly by either person-to-person transmission or through contaminated food. Many norovirus outbreaks have been traced to food that was handled by one infected person. Accordingly, it may be advantageous to provide prophylactic doses of the compounds described herein to individuals in these facilities who are likely to come into contact with Norovirus or other Caliciviridae.

VI. Combination or Alternation Therapy

In one embodiment, the compounds of the invention can be employed together with at least one other antiviral agent, chosen from entry inhibitors, reverse transcriptase inhibitors, protease inhibitors, and immune-based therapeutic agents.

For example, when used to treat or prevent HIV or HBV infection, the active compound or its prodrug or pharmaceutically acceptable salt can be administered in combination or alternation with another antiviral agent, such as anti-HIV, anti-HBV, or anti-HCV agent, including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

| Hepatitis B Therapies | | |
|---|---|---|
| Drug Name | Drug Class | Company |
| Intron A (interferon alfa-2b) | interferon | Schering-Plough |
| Pegasys (Peginterferon alfa-2a) | interferon | Roche |
| Epivir-HBV (lamivudine; 3TC) | nucleoside analogue | GlaxoSmithKline |
| Hepsera (Adefovir Dipivoxil)" | nucleotide analogue | Gilead Sciences |
| Emtriva ® (emtricitabine; FTC) | nucleoside analogue | Gilead Sciences http://www.hivandhepatitis.com/advertisement/triangle.html |

Hepatitis B Therapies

| Drug Name | Drug Class | Company |
|---|---|---|
| Entecavir | nucleoside analogue | Bristol-Myers Squibb |
| Clevudine (CLV, L-FMAU) | nucleoside analogue | Pharmasset |
| ACH 126, 443 (L-Fd4C) | nucleoside analogue | Achillion Pharmaceuticals |
| AM 365 | nucleoside analogue | Amrad |
| Amdoxovir (AMDX, DAPD) | nucleoside analogue | RFS Pharma LLC |
| LdT (telbivudine) | nucleoside analogue | Idenix |
| CS-1220 | nucleoside analogue | Emory University |
| Theradigm | Immune stimulant | Epimmune |
| Zadaxin (thymosin) | Immune stimulant | SciClone |
| EHT 899 | viral protein | Enzo Biochem |
| Dexelvuecitabine/Reverset/D-D4FC | nucleoside analogue | Pharmasset |
| APD | nucleoside analogue | RFS Pharma |
| HBV DNA vaccine | Immune stimulant | PowderJect (UK) |
| MCC 478 | nucleoside analogue | Eli Lilly |
| valLdC (valtorcitabine) | nucleoside analogue | Idenix |
| ICN 2001 | nucleoside analogue | ICN |
| Racivir | nucleoside analogue | Pharmasset |
| Robustaflavone | nucleoside analogue | Advanced Life Sciences |
| LM-019c | | Emory University |
| Penciclovir | nucleoside analogue | |
| Famciclovir | | |
| DXG | nucleoside analogue | |
| ara-AMP prodrugs | | |
| HBV/MF59 | | |
| HDP-P-acyclovir | nucleoside analogue | |
| Hammerhead ribozymes | | |
| Glycosidase Inhibitors | | |
| Pegylated Interferon | | |
| Human Monoclonal Antibodies | | |

HIV Therapies: Protease Inhibitors (PIs)

| Brand Name | Generic Name | Abbreviation | Experimental Code | Pharmaceutical Company |
|---|---|---|---|---|
| Invirase ® | saquinavir (Hard Gel Cap) | SQV (HGC) | Ro-31-8959 | Hoffmann-La Roche |
| Fortovase ® | saquinavir (Soft Gel Cap) | SQV (SGC) | | Hoffmann-La Roche |
| Norvir ® | ritonavir | RTV | ABT-538 | Abbott Laboratories |
| Crixivan ® | indinavir | IDV | MK-639 | Merck & Co. |
| Viracept ® | nelfinavir | NFV | AG-1343 | Pfizer |
| Agenerase ® | amprenavir | APV | 141W94 or VX-478 | GlaxoSmithKline |
| Kaletra ® | lopinavir + ritonavir | LPV | ABT-378/r | Abbott Laboratories |
| Lexiva ® | fosamprenavir | | GW-433908 or VX-175 | GlaxoSmithKline |
| Aptivus ® | tripanavir | TPV | PNU-140690 | Boehringer Ingelheim |
| Reyataz ® | atazanavir | | BMS-232632 | Bristol-Myers Squibb |
| | brecanavir | | GW640385 | GlaxoSmithKline |
| Prezista ™ | darunavir | | TMC114 | Tibotec |

HIV Therapies: Nucleoside/Nucleotide Reverse Transcriptase Inhibitors (NRTIs)

| Brand Name | Generic Name | Abbreviation | Experimental Code | Pharmaceutical Company |
|---|---|---|---|---|
| Retrovir ® | zidovudine | AZT or ZDV | | GlaxoSmithKline |
| Epivir ® | lamivudine | 3TC | | GlaxoSmithKline |
| Combivir ® | zidovudine + lamivudine | AZT + 3TC | | GlaxoSmithKline |
| Trizivir ® | abacavir + zidovudine + lamivudine | ABC + AZT + 3TC | | GlaxoSmithKline |
| Ziagen ® | abacavir | ABC | 1592U89 | GlaxoSmithKline |
| Epzicom ™ | abacavir + lamivudine | ABC + 3TC | | GlaxoSmithKline |
| Hivid ® | zalcitabine | ddC | | Hoffmann-La Roche |
| Videx ® | didanosine: buffered versions | ddI | BMY-40900 | Bristol-Myers Squibb |
| Entecavir | baraclude | | | Bristol-Myers Squibb |

HIV Therapies: Nucleoside/Nucleotide Reverse Transcriptase Inhibitors (NRTIs)

| Brand Name | Generic Name | Abbreviation | Experimental Code | Pharmaceutical Company |
|---|---|---|---|---|
| Videx ® EC | didanosine: delayed-release capsules | ddI | | Bristol-Myers Squibb |
| Zerit ® | stavudine | d4T | BMY-27857 | Bristol-Myers Squibb |
| Viread ™ | tenofovir disoproxil fumarate (DF) | TDF or Bis(POC) PMPA | | Gilead Sciences |
| Emtriva ® | emtricitabine | FTC | | Gilead Sciences |
| Truvada ® | Viread + Emtriva | TDF + FTC | | Gilead Sciences |
| Atripla ™ | | TDF + FTC + Sustiva ® | | Gilead/BMS/Merck |
| | amdoxovir | DAPD, AMDX | | RFS Pharma LLC |
| apricitabine | AVX754 | | SPD 754 | Avexa Ltd |
| | Alovudine | FLT | MIV-310 | Boehringer |
| | Elvucitabine | L-FD4C | ACH-126443, SN1461, SN1212 | Achillion |
| | KP-1461 | | | Koronis |
| | Racivir | RCV | | Pharmasset |
| Dexelvuecitabine | Reverset | D-D4FC | DPC 817 | Pharmasset |
| | | | GS9148 and prodrugs thereof | Gilead Sciences |

HIV Therapies: Non-Nucleoside Reverse Transcriptase Inhibitors (NNRTIs)

| Brand Name | Generic Name | Abbreviation | Experimental Code | Pharmaceutical Company |
|---|---|---|---|---|
| Viramune ® | nevirapine | NVP | BI-RG-587 | Boehringer Ingelheim |
| Rescriptor ® | delavirdine | DLV | U-90152S/T | Pfizer |
| Sustiva ® | efavirenz | EFV | DMP-266 | Bristol-Myers Squibb |
| | (+)-calanolide A | | | Sarawak Medichem |
| | capravirine | CPV | AG-1549 or S-1153 | Pfizer |
| | | | DPC-083 | Bristol-Myers Squibb |
| | | | TMC-125 | Tibotec-Virco Group |
| | | | TMC-278 | Tibotec-Virco Group |
| | | | IDX12899 | Idenix |
| | | | IDX12989 | idenix |

HIV Therapies: Other Classes of Drugs

| Brand Name | Generic Name | Abbreviation | Experimental Code | Pharmaceutical Company |
|---|---|---|---|---|
| Viread ™ | tenofovir disoproxil fumarate (DF) | TDF or Bis(POC) PMPA | | Gilead Sciences |

Cellular Inhibitors

| Brand Name | Generic Name | Abbreviation | Experimental Code | Pharmaceutical Company |
|---|---|---|---|---|
| Droxia ® | hydroxyurea | HU | | Bristol-Myers Squibb |

Entry Inhibitors (including Fusion Inhibitors)

| Brand Name | Generic Name | Abbreviation | Experimental Code | Pharmaceutical Company |
|---|---|---|---|---|
| Fuzeon ™ | enfuvirtide | | T-20 | Trimeris |
| | | | T-1249 | Trimeris |
| | | | AMD-3100 | AnorMED, Inc. |
| | CD4-IgG2 | | PRO-542 | Progenics Pharmaceuticals |
| | | | BMS-488043 | Bristol-Myers Squibb |
| | aplaviroc | | GSK-873,140 | GlaxoSmithKline |
| | Peptide T | | | Advanced Immuni T, Inc. |
| | | | TNX-355 | Tanox, Inc. |
| | maraviroc | | UK-427,857 | Pfizer |
| | CXCR4 Inhibitor | | | |
| AMD070 | | | AMD11070 | AnorMED, Inc. |
| | CCR5 antagonist | | | |
| vicriroc | | SCH-D | SCH-417690 | Schering-Plough |

| HIV Therapies: Immune-Based Therapies ||||| 
|---|---|---|---|---|
| Brand Name | Generic Name | Abbreviation | Experimental Code | Pharmaceutical Company |
| Proleukin ® | aldesleukin, or Interleukin-2 | IL-2 | | Chiron Corporation |
| Remune ® | HIV-1 Immunogen, or Salk vaccine | | AG1661 | The Immune Response Corporation |
| | | | HE2000 | HollisEden Pharmaceuticals |

| Table of anti-Hepatitis C Compounds in Current Clinical Development |||
|---|---|---|
| Drug Name | Drug Category | Pharmaceutical Company |
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/ LY 570310 | Protease Inhibitor | Vertex/Eli Lilly |
| ISIS 14803 | Antisense | Isis Pharmaceutical/ Elan |
| IDN-6556 | Caspase inhibitor | Idun Pharmaceuticals, Inc. http://www.idun.com |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wye |
| CH-6 | Serine Protease | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monclonal Antibody | XTL |
| IC41 | Therapeutic Vaccine | Intercell |
| Medusa Interferon | Longer acting interferon | Flamel Technologies |
| E-1 | Therapeutic Vaccine | Innogenetics |
| Multiferon | Long Acting Interferon | Viragen |
| BILN 2061 | Serine Protease | Boehringer - Ingelheim |
| Interferon beta-1a (REBIF) | Interferon | Ares-Serono |

VII. Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor. In one embodiment, the compounds described herein can be employed together with at least one other antiviral agent chosen from reverse transcriptase inhibitors, protease inhibitors, fusion inhibitors, entry inhibitors and polymerase inhibitors.

In addition, compounds according to the present invention can be administered in combination or alternation with one or more anti-retrovirus, anti-HBV, interferon, anti-cancer or antibacterial agents, including but not limited to other compounds of the present invention. Certain compounds described herein may be effective for enhancing the biological activity of certain agents according to the present invention by reducing the metabolism, catabolism or inactivation of other compounds, and as such, are co-administered for this intended effect.

VIII. Combination Therapy for Treating Noroviral Infections

In addition to the antiviral compounds described herein, other compounds can also be present. For example, type I interferon (IFN) is known to inhibit Norovirus replication. Certain vitamins, particularly vitamin C, are believed to be effective at treating certain viral infections. One study has shown that Vitamin A supplementation reduced the prevalence of Norovirus GII infections, increased the length of both Norovirus GI and GII shedding, and decreased the prevalence of NoV-associated diarrhea (1: J Infect Dis. 2007 Oct. 1; 196(7):978-85. Epub 2007 Aug. 22). Lysine is known as an antiviral agent. It is also known that virus-like particles (VLPs) derived from genogroup II (GII) Norovirus were bound to cell surface heparan sulfate proteoglycan and other negatively charged glycosaminoglycans. To treat the symptoms of infection, one can also administer an anti-emetic, an anti-diarrheal agent, and/or an analgesic.

IX. Pharmaceutical Compositions

Hosts, including but not limited to humans, infected with a human immunodeficiency virus, a hepatitis B virus, Flaviviridae family of viruses or Caliciviridae virus or a gene fragment thereof, or cancer can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.1 and about 100 mg/kg, more generally, between about 1 and 50 mg/kg, and, preferably, between about 1 and about 20 mg/kg, of body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 3000 mg, preferably 70 to 1400 mg of active ingredient per unit dosage form. An oral dosage of 50-1000 mg is usually convenient.

Ideally the active ingredient should be administered to achieve peak plasma concentrations of the active compound from about 0.2 to 70 preferably about 1.0 to 15 µM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

| | |
|---|---|
| aq | aqueous |
| CDI | carbonyldiimidazole |
| DMF | N,N-dimethylformamide |
| DMSO | dimethylsulfoxide |
| EDC | 1-ethyl-3-(3-dimethyllaminopropyl)carbodiimide hydrochloride |
| EtOAc | ethyl acetate |
| h | hour/hours |
| HOBt | N-hydroxybenzotriazole |
| M | molar |
| min | minute |
| rt or RT | room temperature |
| TBAT | tetrabutylammonium triphenyldifluorosilicate |
| TBTU | O-(Benzotriazol-1-yl)-N,N,N',N'-tetramethyluronium tetrafluoroborate |
| THF | tetrahydrofuran |

X. General Schemes for Preparing Active Compounds

Methods for the facile preparation of 6-substituted-2-amino purine nucleoside monophosphate and phosphonates prodrugs are also provided. The 6-substituted-2-amino purine nucleotide monophosphates and phosphonates prodrugs disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

Generally, the nucleotides of formula I-XVIII are prepared by first preparing the corresponding nucleoside, then capping the 5'-hydroxy group as a monophosphate or other analog as described herein that can be readily converted in vivo to an active triphosphate form of the compound.

The various reaction schemes are summarized below.

Scheme 1 is a non-limiting example of the synthesis of active compounds of the present invention, and in particular, a synthetic approach to monophosphate prodrugs XII, XIII, XIV.

Scheme 2 is a non-limiting example of the synthesis of active compounds of the present invention, and in particular, an alternate synthetic approach to monophosphate prodrugs XII, XIII, XIV.

Scheme 3 is a non-limiting example of the synthesis of active compounds of the present invention, and in particular, a synthetic approach to monophosphate prodrug XV.

Scheme 4 is a non-limiting example of the synthesis of active compounds of the present invention, and in particular, a synthetic approach to monophosphate prodrug XVI.

Scheme 5 is a non-limiting example of the synthesis of active compounds of the present invention, and in particular, a synthetic approach to monophosphate prodrug XVII.

Scheme 6 is a non-limiting example of the synthesis of active compounds of the present invention, and in particular, an alternate synthetic approach to monophosphate prodrug XVII.

Scheme 7 is a non-limiting example of the synthesis of active compounds of the present invention, and in particular, a synthetic approach to monophosphate prodrug XVIII.

Scheme 8 is a non-limiting example of the synthesis of active compounds of the present invention, and in particular, an alternate synthetic approach to monophosphate prodrug XVIII.

Scheme 9 is a non-limiting example of the synthesis of active compounds of the present invention, and in particular, a synthetic approach to nucleosides 1.

Scheme 10 is a non-limiting example of the synthesis of active compounds of the present invention, and in particular, an alternate synthetic approach to nucleosides 1.

In one embodiment, nucleosides of formulas XII, XIII or XIV are prepared by protection of compound 1 by a group such as TIPS to provide 2 bearing a free alpha-hydroxyl group at the 3'-position of the sugar (Scheme 1). Preparation of compound 1 is accomplished by one of ordinary skill in the art, by methods outlined in: (a) Rajagopalan, P.; Boudinot, F. D; Chu, C. K.; Tennant, B. C.; Baldwin, B. H.; Antiviral Nucleosides Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, Ga., USA, pp: 319-37 d) Handbook of Nucleoside Synthesis: Vorbruggen H. & Ruh-Pohlenz C. John Wiley & sons 2001), and by general Schemes 9-10. Coupling of 2 with acids 3 or 4 can be accomplished by agents such as EDC, EDC/HOBt, TBTU, or CDI to give esters 5 or 6. After removal of protecting groups the resulting amino alcohols can be converted to the monophosphate prodrugs XII or XIII by exposure to phosphorous oxychloride or phosphorothioyl trichloride (POCl$_3$ or PSCl$_3$) or alternatively after water workup of the phosphorous oxychloride or phosphorothioyl trichloride reaction, a coupling agent such as DCC can be utilized in the formation of XII or XIII. Compound 7 can be obtained after water workup of the phosphorous oxychloride or phosphorothioyl trichloride reaction and subsequent exposure to phosgene or a phosgene equivalent such as CDI or triphosgene gives monophosphate prodrug XIV.

Scheme 1
A synthetic approach to monophosphate prodrugs XII, XIII, XIV. (Base is a natural or unnatural nucleoside base; $R^{4'}$, $R^5$, $R^{5'}$, $R^6$, Y, M, $R^{20}$, and $R^{7'}$ are as defined in active compound section)

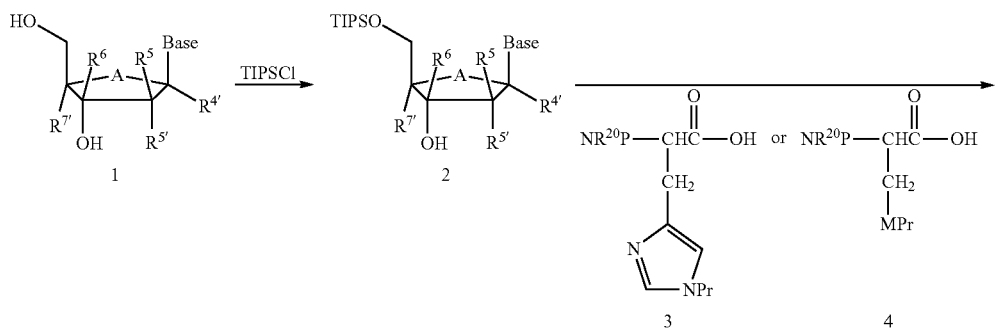

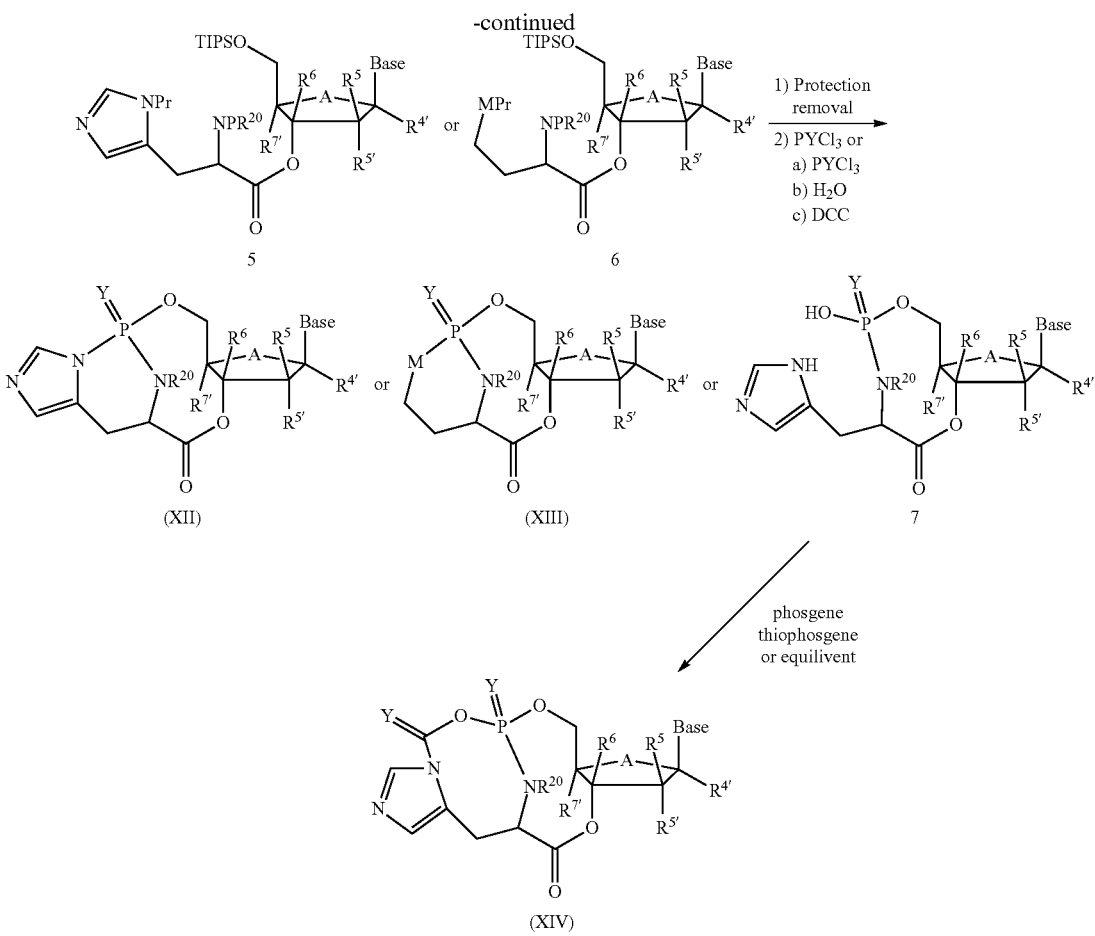

Alternatively monophosphate prodrugs XII, XIII, XIV can be synthesized as outlined in Scheme 2, namely nucleoside 1 can be converted to the monophosphate, 8 directly by the action of phosphorous oxychloride or phosphorothioyl trichloride in trimethyl phosphate. Coupling to the amino esters 9 or 10 can be accomplished with standard coupling agents such as DCC to give phosphoramidates 7 and 11. Deprotection and subsequent coupling of 7 or 11 with agents such as EDC, EDC/HOB$_t$, TBTU, or CDI provides monophosphate prodrugs XII and XIII. Monophosphate prodrug XIV can be obtained from 7 as described in Scheme 1.

Scheme 2
An alternate synthetic approach to monophosphate prodrugs XII, XIII, XIV. (Base is a natural or unnatural nucleoside base; $R^{4'}$, $R^5$, $R^{5'}$, $R^6$, Y, M, $R^{20}$, and $R^{7'}$ are as defined in active compound section)

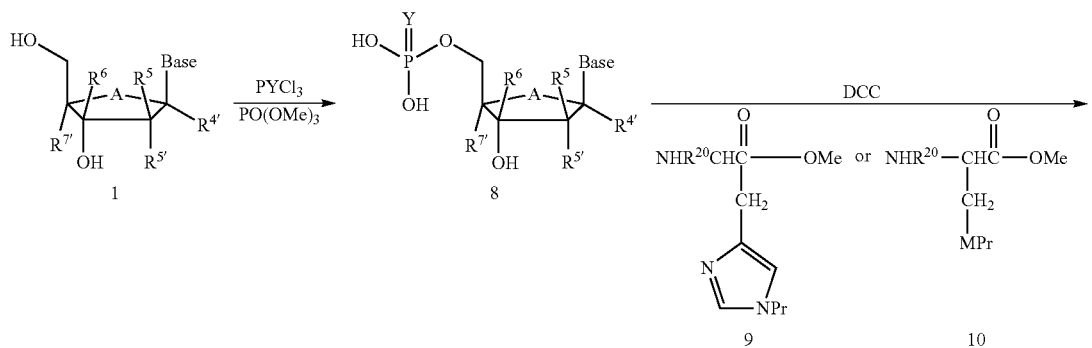

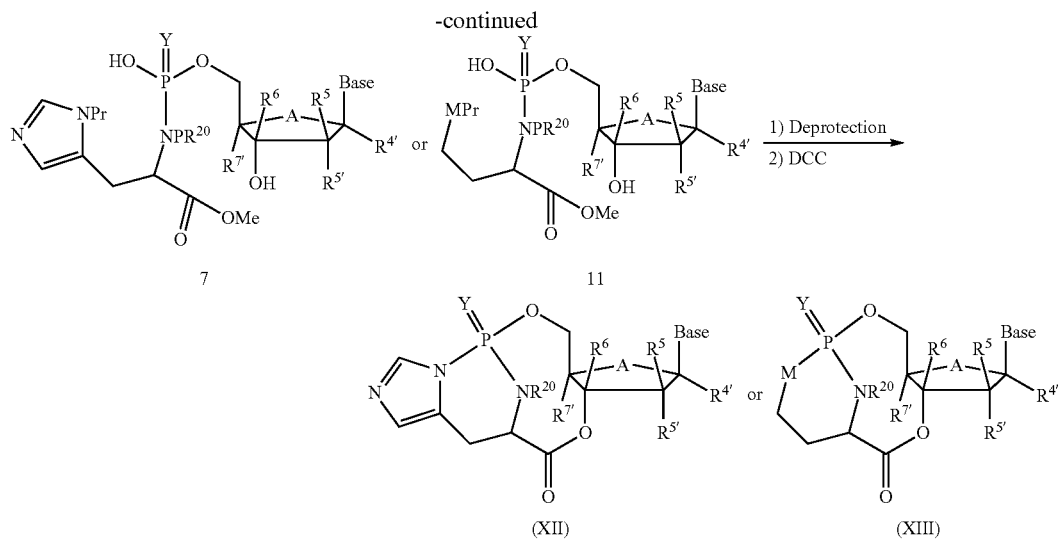

R⁴, R⁵, R⁵', R⁶, R⁷', and
Base may contain suitable protection;
Pr = protection

Monophosphate prodrug XV can be prepared as outlined in Scheme 3 starting from phenol 12 (Scheme 3). Exposure of 12 to phosphorous oxychloride or phosphorothioyl trichloride provides 13, which is subsequently allowed to react with an amino ester 14 to give phosphoramidate 15. Nucleoside 1 can next be converted to monophosphate analog 16 by reaction of the 5'-hydroxyl group with the chlorophosphorylamino propanoate, 15. Deprotection and subsequent coupling of 16 with agents such as EDC, EDC/HOBt, TBTU, or CDI provides monophosphate prodrugs XV.

Scheme 3
A synthetic approach to monophosphate prodrug XV. (Base is a natural or unnatural nucleoside base; R⁴', R⁵, R⁵', R⁶, Y, R²⁰ R²¹ R²², and R⁷' are as defined in active compound section)

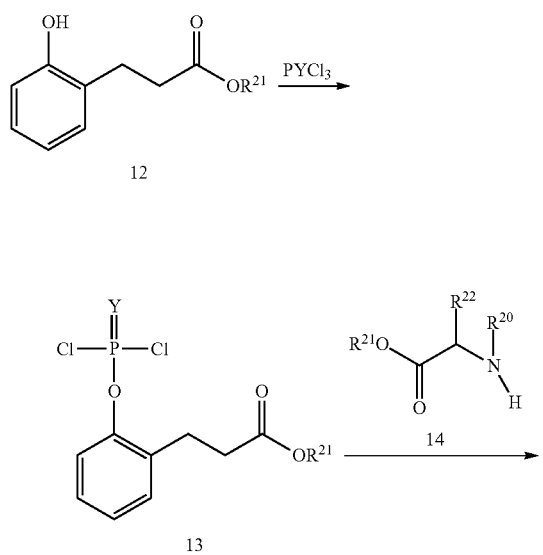

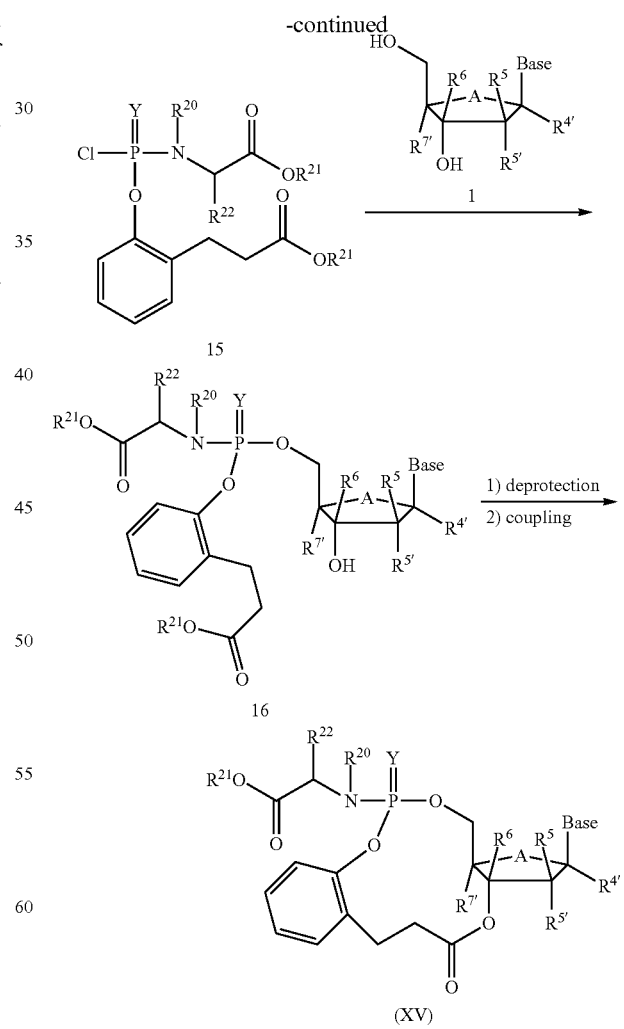

R⁴', R⁵, R⁵', R⁶, R⁷', and
Base may contain suitable protection

Monophosphate prodrug XVI can be prepared by reaction of phenol 12 with phosphorous oxychloride or phosphorothioyl trichloride to provide diphenyl phosphorochloridate, 17 (Scheme 4). Nucleoside 1 can next be converted to an intermediate monophosphate analog by reaction of the 5'-hydroxyl group with the diphenyl phosphorochloridate, 17. Deprotection and subsequent ester formation with the 3'-hydroxyl group with agents such as EDC, EDC/HOBt, TBTU, or CDI followed by reesterification with $R^{21}OH$ provides monophosphate prodrugs XVI.

reaction of the 5'-hydroxyl group with the cyclic phosphorodiamidic chloride, 22. Deprotection and subsequent coupling of 22 with agents such as EDC, EDC/HOBt, TBTU, or CDI provides monophosphate prodrugs XVII.

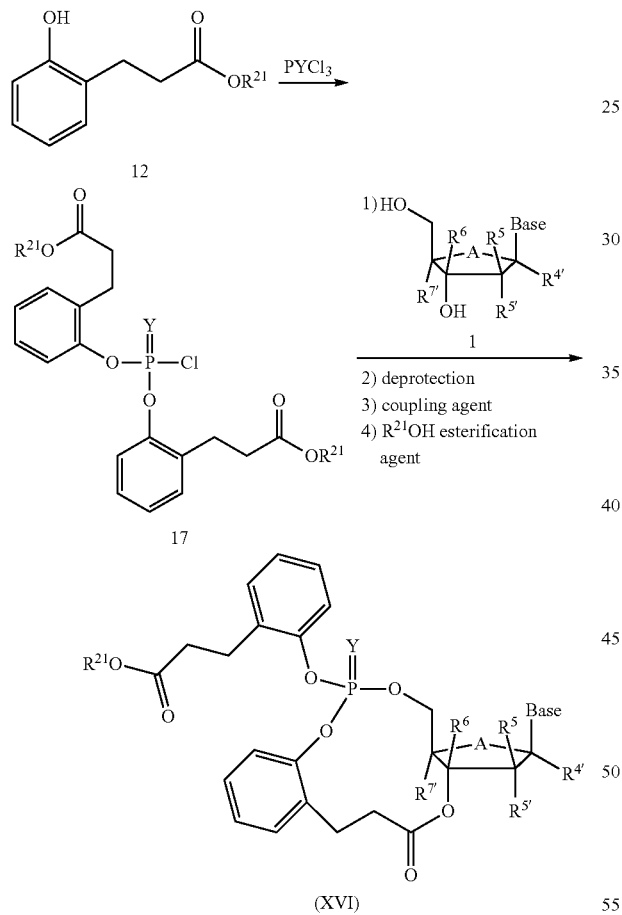

Scheme 4
A synthetic approach to monophosphate prodrug XVI.
(Base is a natural or unnatural nucleoside base; $R^{4'}, R^5, R^{5'}, R^6, Y, R^{21}$, and $R^{7'}$ are as defined in active compound section)

$R^{4'}, R^5, R^{5'}, R^6, R^{7'}$, and Base may contain suitable protection

Monophosphate prodrug XVII can be prepared by initial reaction of protected tryptophan 18 with protected amino acid 19 with coupling agents such as EDC, EDC/HOBt, TBTU, or CDI to give dipeptide 20 (Scheme 5). Removal of the amine protections gives then diamine 21 which can then be reacted with phosphorous oxychloride or phosphorothioyl trichloride to give the cyclic phosphorodiamidic chloride, 22. Nucleoside 1 can next be converted to a monophosphate analog by

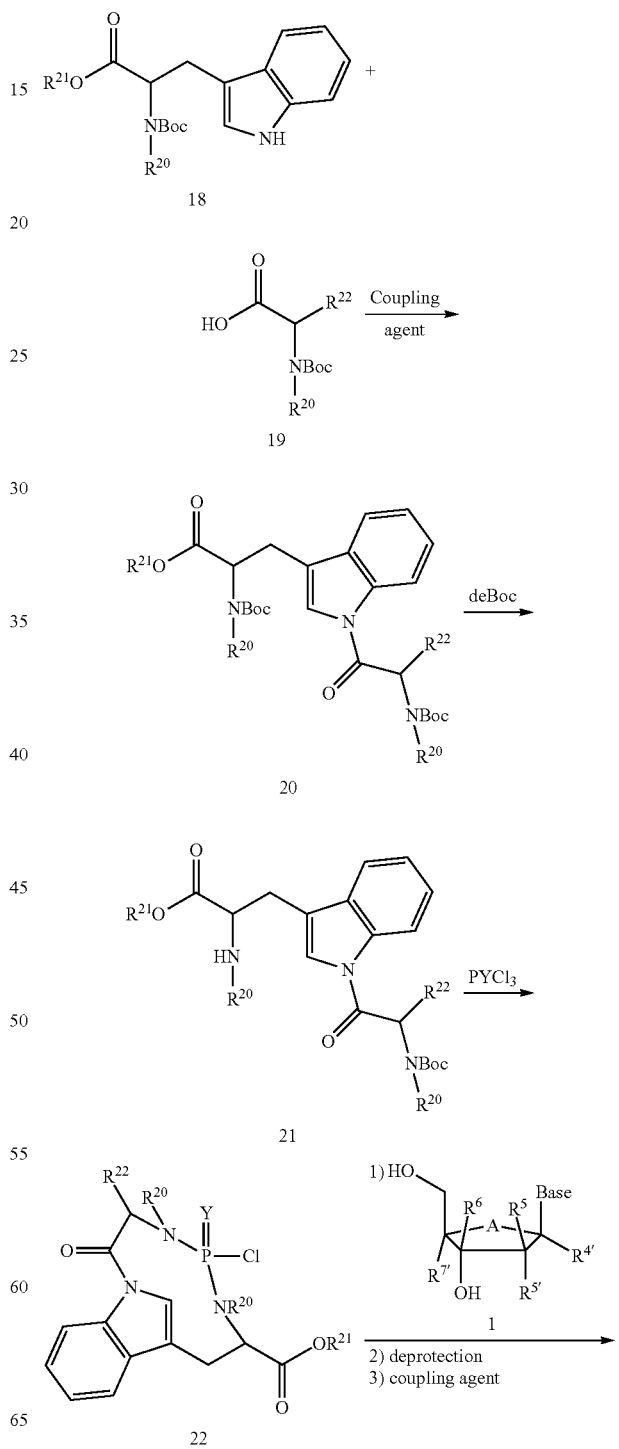

Scheme 5
A synthetic approach to monophosphate prodrug XVII.
(Base is a natural or unnatural nucleoside base; $R^{4'}, R^5, R^{5'}, R^6, Y, R^{20} R^{21} R^{22}$, and $R^{7'}$ are as defined in active compound section)

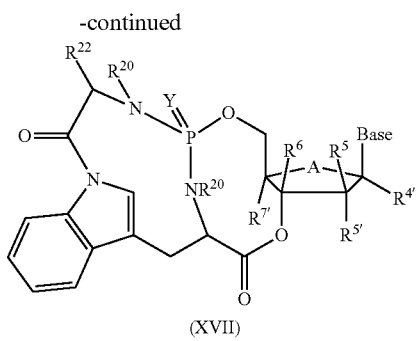

(XVII)

$R^{4'}, R^5, R^{5'}, R^6, R^{7'}$, and
Base may contain suitable protection

Alternatively, monophosphate prodrug XVII can be prepared from monophosphate analog 8 followed by coupling with dipeptide 20 (Scheme 6).

Scheme 6
An alternate synthetic approach to monophosphate prodrug XVII.
(Base is a natural or unnatural nucleoside base; $R^{4'}, R^5, R^{5'}, R^6$, Y, $R^{20} R^{21} R^{22}$, and $R^{7'}$ are as defined in active compound section)

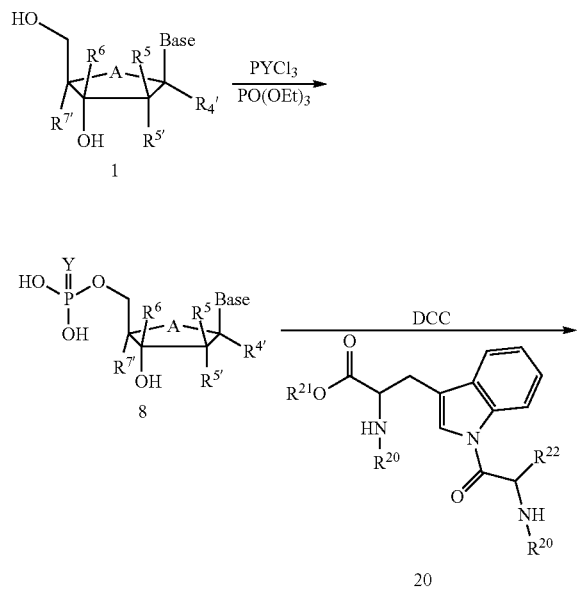

(XVII)

$R^{4'}, R^5, R^{5'}, R^6, R^{7'}$, and
Base may contain suitable protection

Monophosphate prodrug XVIII can be prepared by initial reaction of phosphoramidic dichloride 23 with nucleoside 1 (Scheme 7). Subsequent reaction of the produced intermediate with water, hydrogen sulfide, or an amine provides monophosphate analog 24 (Scheme 7). Exposure of the bis nucleophile 24 to phosgene or a phosgene equivalent such as CDI provides monophosphate prodrugs XVIII.

Scheme 7
A synthetic approach to monophosphate prodrug XVIII.
(Base is a natural or unnatural nucleoside base; $R^{4'}, R^5, R^{5'}, R^6$, Y, M, $R^{20}$ $R^{21} R^{22}$, and $R^{7'}$ are as defined in active compound section)

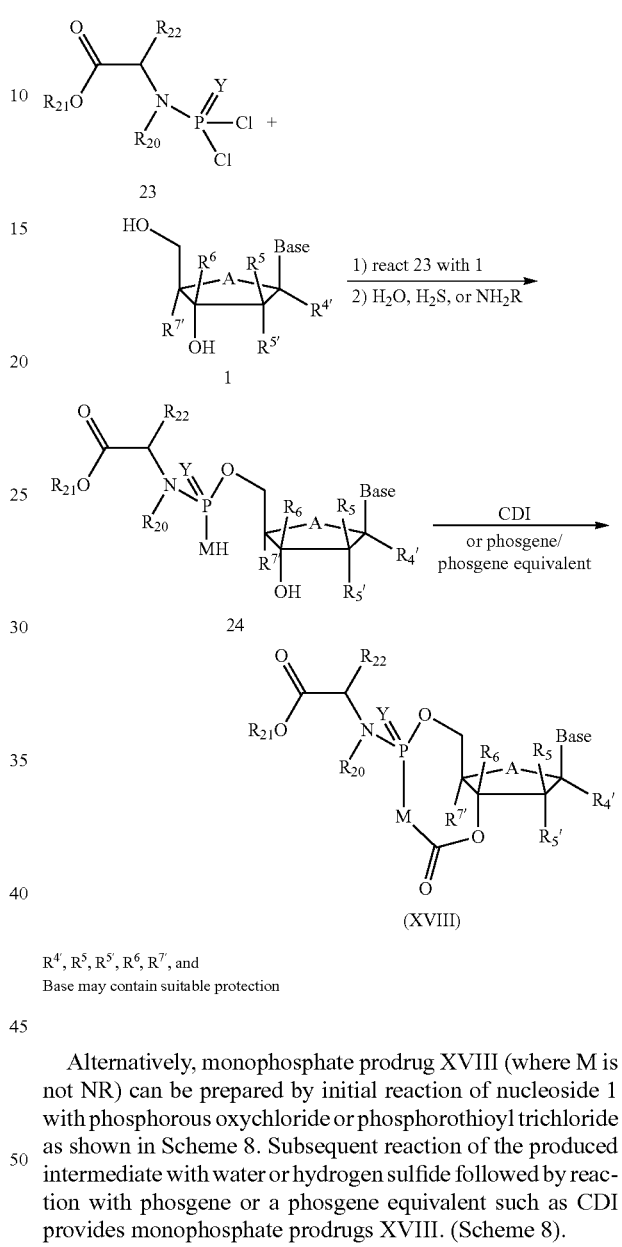

(XVIII)

$R^{4'}, R^5, R^{5'}, R^6, R^{7'}$, and
Base may contain suitable protection

Alternatively, monophosphate prodrug XVIII (where M is not NR) can be prepared by initial reaction of nucleoside 1 with phosphorous oxychloride or phosphorothioyl trichloride as shown in Scheme 8. Subsequent reaction of the produced intermediate with water or hydrogen sulfide followed by reaction with phosgene or a phosgene equivalent such as CDI provides monophosphate prodrugs XVIII. (Scheme 8).

Scheme 8
An alternate synthetic approach to monophosphate prodrug XVIII.
(Base is a natural or unnatural nucleoside base; $R^{4'}, R^5, R^{5'}, R^6$, Y, $R^{20} R^{21} R^{22}$, and $R^{7'}$ are as defined in active compound section)

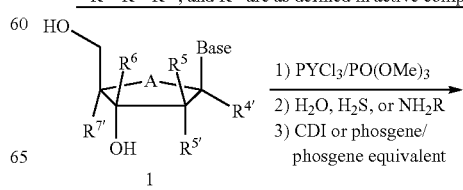

-continued

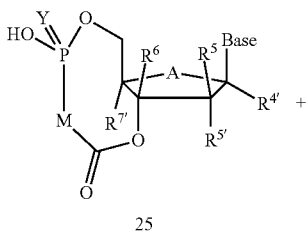

25

(XVIII)

14

$R^{4'}$, $R^5$, $R^{5'}$, $R^6$, $R^7$, and
Base may contain suitable protection Nucleoside 1 can be prepared by coupling sugar 26 with a protected or silylated purine base in the presence of Lewis acid such as TMSOTf. Deprotection of the 3'- and 5'-hydroxyls gives nucleoside 1.

Scheme 9
A synthetic approach to nucleosides 1. (Base is a natural or unnatural nucleoside base; $R^{4'}$, $R^5$, $R^{5'}$, $R^6$, Y, $R^{20}$ $R^{21}$ $R^{22}$, and $R^7$ are as defined in active compound section)

26 protected or silylated Purine Base  1) TMSOTf  2) deprotection

1

$R^{4'}$, $R^5$, $R^{5'}$, $R^6$, $R^7$, and
Base may contain suitable protection;
Pr = protection;
LG = OCOalkyl, OCOaryl, OCOalkylaryl Alternatively, nucleoside 1 can be prepared from 1'-halo or 1'-hydroxy compound 27. For the case of 1'-halo a protected or free purine base in the presence of a base such as triethyl amine or sodium hydride, followed by deprotection, gives nucleosides 1. For the case of 1'-hydroxy, a protected or free purine base, in the presence of a Mitsunobu coupling agent such as diisopropyl azodicarboxylate, followed by deprotection, gives nucleosides 1.

Scheme 10
An alternate synthetic approach to nucleosides 1. (Base is a natural or unnatural nucleoside base; $R^{4'}$, $R^5$, $R^{5'}$, $R^6$, Y, $R^{20}$ $R^{21}$ $R^{22}$, and $R^7$ are as defined in active compound section)

27 protected or silylated Purine Base  1) Base or Mitsunobu  2) deprotection

1

$R^{4'}$, $R^5$, $R^{5'}$, $R^6$, $R^7$, and
Base may contain suitable protection;
Pr = protection;
X = halogen or OH The present invention is further illustrated in the following examples. Schemes 11-14 and Examples 1-6 show preparative methods for synthesizing 6-substituted purine nucleotide prodrugs, and Examples 7-35 show methods for the biological evaluation of the 6-substitute purine nucleoside, nucleotide, and nucleotide analogs. It will be understood by one of ordinary skill in the art that these examples are in no way limiting and that variations of detail can be made without departing from the spirit and scope of the present invention.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel or via reverse-phase high performance liquid chromatography.

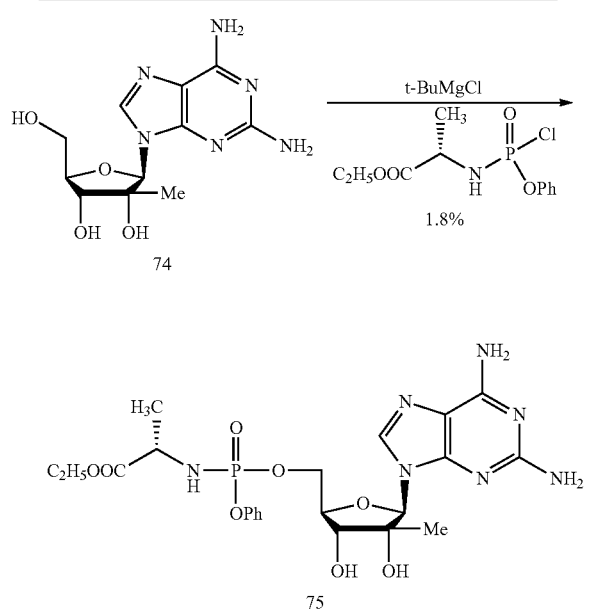

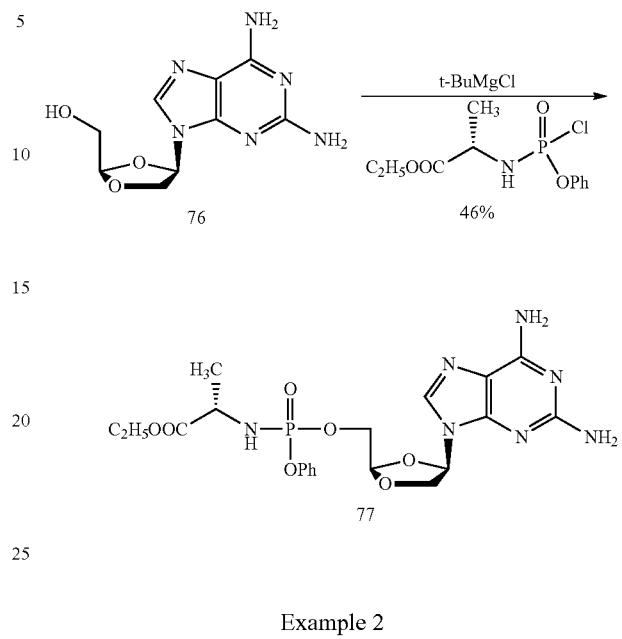

Example 1

(2S)-ethyl 2-(((((2R,3R,4R,5R)-5-(2,6-diamino-9H-purin-9-yl)-3,4-dihydroxy-4-methyltetrahydrofuran-2-yl)methoxy)(phenoxy)phosphorylamino)propanoate (75)

To a solution of (74) (30 mg, 0.1 mmol) in THF (1 mL) and DMF (1 mL) at 0° C. was added (2R)-ethyl 2-(chloro(phenoxy)phosphorylamino)propanoate[1] (0.4 mL, 0.4 mmol), then added t-BuMgCl (0.4 mL, 0.4 mmol) in portions. After stirring overnight at rt, the reaction mixture was neutralized with ammonium chloride$_{(aq)}$, conc, then purified by flash column chromatography with dichloromethane:methanol=7:1-7:2 to give 75 (1 mg, 1.8%).

LC/MS calcd. for $C_{22}H_{30}N_7O_8P$ 551.1, observed: 552.1 (M+1).

References 1. (a) Perrone, P.; Daverio, F.; Valente, R.; Rajyaguru, S.; Martin J. A.; Lévêque, V.; Pogam, S. L.; Najera, I.; Klumpp, K.; Smith, D.; B. and McGuigan, C. First Example of Phosphoramidate Approach Applied to a 4'-Substituted Purine Nucleoside (4'-Azidoadenosine): Conversion of an Inactive Nucleoside to a Submicromolar Compound versus Hepatitis C Virus. *J. Med. Chem.* 2007, 50, 5463-5470. (b) Uchiyama, M.; Aso, Y.; Noyori, R.; Hayakawa, Y. O-Selective phosphorylation of nucleosides without N-protection. *J. Org. Chem.* 1993, 58, 373-379.

Example 2

(2R)-ethyl-2-((((4R)-4-(2,6-diamino-9H-purin-9-yl)-1,3-dioxolan-2-yl)methoxy)(phenoxy)phosphorylamino)propanoate (77)

To a solution of compound 76 (30 mg, 0.12 mmol) in THF (5 mL) was added 1 M solution of t-BuMgCl (0.36 mL, 0.36 mmol) and stirred for 30 min. To the reaction mixture was added (2R)-ethyl 2-(chloro(phenoxy)phosphorylamino)propanoate (0.36 mL, 0.36 mmol) in THF at rt and was stirred overnight, neutralized with ammonium chloride$_{(aq)}$, conc, the crude mixture was purified by flash column chromatography with ethyl acetate:methanol=5:1 to give 77 (28 mg, 46%).

$^1$H-NMR (CD$_3$OD, 300 MHz) δ: 7.80-7.79 (s, 1H), 7.26-7.09 (m, 5H), 6.27 (m, 1H), 6.12 (brs, 2H), 5.25 (m, 3H), 4.47 (m, 2H), 4.22 (m, 2H), 4.03 (m, 2H), 3.83 (m, 1H), 1.33-1.15 (m, 6H).

LC/MS calcd. for $C_{20}H_{27}N_7O_7P$ 508.2, observed: 508.3 (M+1).

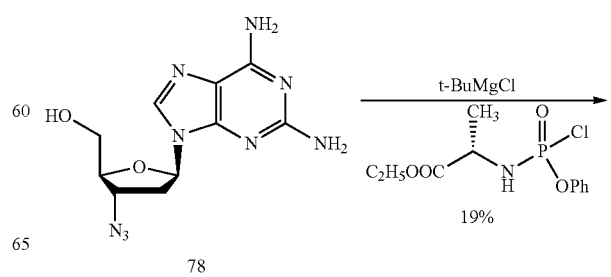

59

-continued

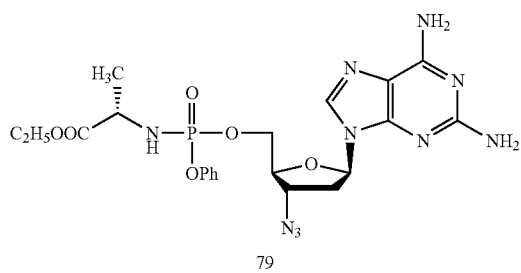

79

Example 3

(2R)-ethyl 2-(((((2S,3S,5R)-3-azido-5-(2,6-diamino-9H-purin-9-yl)tetrahydrofuran-2-yl)methoxy)-(phenoxy)phosphorylamino)propanoate (79)

t-BuMgCl (0.22 mL, 0.22 mmol) was added to a suspension of compound 78 (34 mg, 0.11 mmol) in THF (5 mL). The reaction mixture was stirred for 30 min, then cooled to 0° C., (2R)-ethyl 2-(chloro(phenoxy)phosphorylamino)propanoate (0.22 mL, 0.22 mmol) in THF was added. The reaction mixture was stirred overnight at rt, neutralized with ammonium chloride$_{(aq)}$, conc, the crude mixture was purified by flash column chromatography with ethyl acetate:methanol=5:1 to give 79 (12 mg, 19%).

$^1$H-NMR (CD$_3$OD, 300 MHz) δ: 7.85, 7.89 (2s, 1H), 7.12 (m, 5H), 6.17 (m, 1H), 4.60 (m, 1H), 4.37 (m, 1H), 4.22 (m, 2H), 4.03 (m, 3H), 3.83 (m, 1H), 2.85 (m, 1H), 2.46 (m, 1H), 1.22 (m, 3H), 1.15 (m, 3H).

LC/MS calcd. for C$_{21}$H$_{28}$N$_{10}$O$_6$P 547.2, observed: 547.3 (M+1).

Scheme 14.
Synthesis of 3'-Azido-2',3'-dideoxyguanosine analog (83).

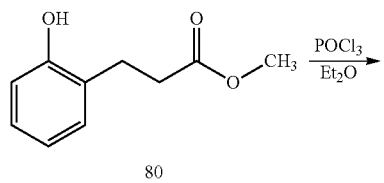

80

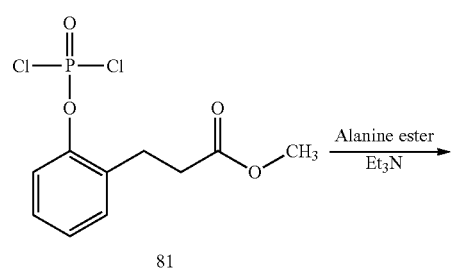

81

60

-continued

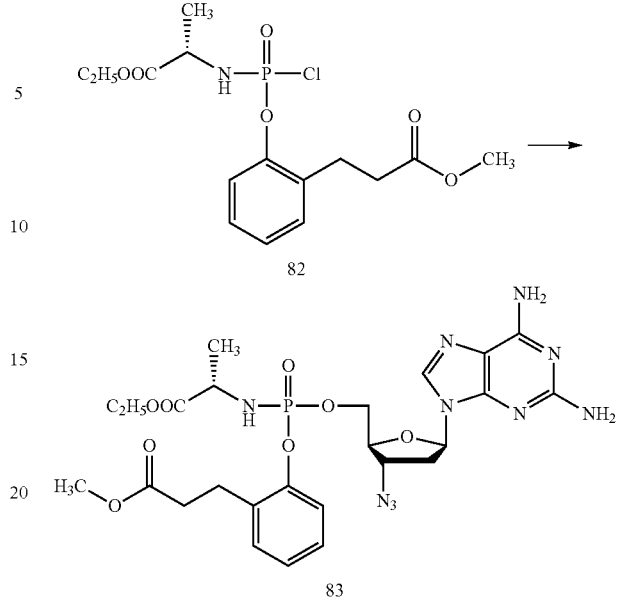

Example 4

Methyl 3-(2-(dichlorophosphoryloxy)phenyl)propanoate (81)$^2$

Dry triethylamine (0.38 mL, 2.8 mmol) and methyl 3-(2-hydroxyphenyl)propanoate, 80 (0.5 g, 2.77 mmol) in dry ether (9.2 mL) were added dropwise to a solution of dry ether (5 mL) containing phosphorus oxychloride (0.25 mL, 2.8 mmol) at −78° C. under nitrogen. Following the addition, the reaction mixture was slowly allowed to warm to rt, and stirred for 1 h. The solvent was removed under reduced pressure to give crude product as an oil containing a significant amount of solid.

References

2. Lemmens, R. WO2003/070944, Method Of Separation Using Aromatic Thioether Ligands.

Example 5

(2R)-ethyl 2-(chloro(2-(3-methoxy-3-oxopropyl)phenoxy)phosphorylamino)propanoate (82)

Methyl 3-(2-(dichlorophosphoryloxy)phenyl)propanoate, 81 (2.77 mmol) and L-alanine methyl ester hydrochloride (0.42 g, 2.77 mmol) were suspended in anhydrous dichloromethane (10 mL). Anhydrous triethylamine (0.37 mL, 2.77 mmol) and dichloromethane (5 mL) were added dropwise at −78° C. under nitrogen. Following the addition, the reaction mixture was slowly warmed to it and stirred overnight. The solvent was removed under reduced pressure; the solid was washed with anhydrous ether (20 mL×2), and filtered. The filtrate was concentrated to a residue to give crude product as an oil. Dilution with THF (2.77 mL) gave a 1 M solution, which was used in the following step without any further purification.

Example 6

(2R)-ethyl 2-((((2S,3S,5R)-3-azido-5-(2,6-diamino-9H-purin-9-yl)tetrahydrofuran-2-yl)methoxy)-(2-(3-methoxy-3-oxopropyl)phenoxy)phosphorylamino)propanoate (83)

This compound was prepared in the manner described for compound 79 in Example 3.

Example 7

Conversion of 6-Substituted-2-Amino Purine Nucleosides to 6-Hydroxy-2-Amino Purine Nucleosides The various nucleosides prepared as described above, with functionality at the 6'-position other than a hydroxy group, are readily converted, in vivo, to the 6'-hydroxy form when the 5'-OH group is not converted to the monophosphate prodrug.

Shown below are multiple examples of the LC/MS qualitative analysis of nucleotides formed after 4 hr incubation of 50 μM 6-substituted-2-amino purine nucleosides in PBM cells. Incubation of 3'-azido G (RS-527) at 50 μM in Peripheral Blood Mononuclear (PBM) cells and subsequent analysis by liquid chromatography with mass spectrometer detection resulted in strong signals for RS-527-diphosphate (DP) and RS-527-triphosphate (TP) while the signal for RS-527-monophosphate (MP) was near the level of detection (FIG. 1).

Figure 2:
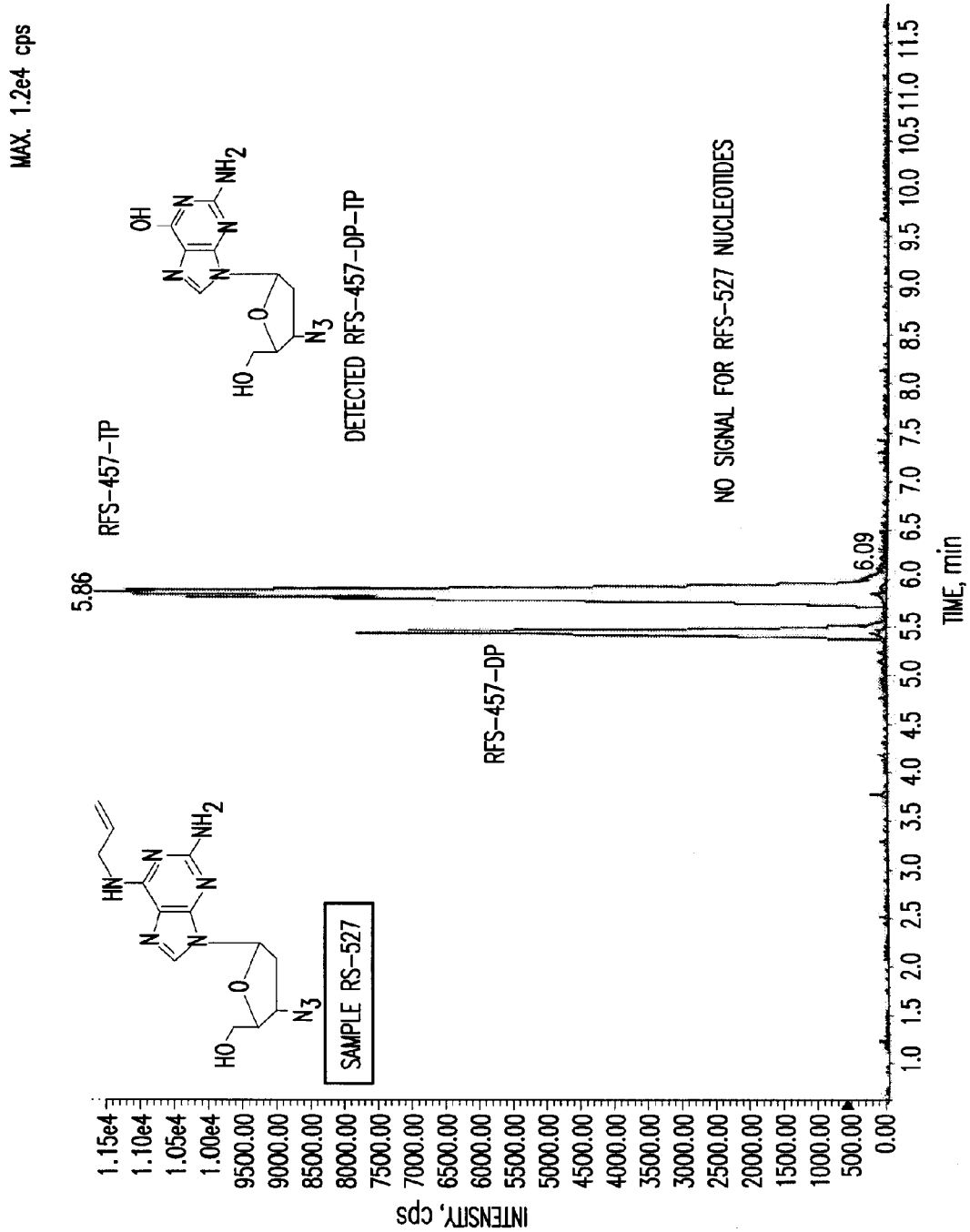
FIG. 2: LC/MS analysis of nucleotides formed after 4 hr incubation in PBM cells of 50 μM RS-527.

Incubation of RFS-427, which contains a 6-N-allyl group, in PBM cells resulted the detection of RFS-457-DP and RFS-457-TP. No RFS-427, RFS-427-MP, RFS-427-DP, or RFS-427-TP were detected (FIG. 2).

Figure 3:
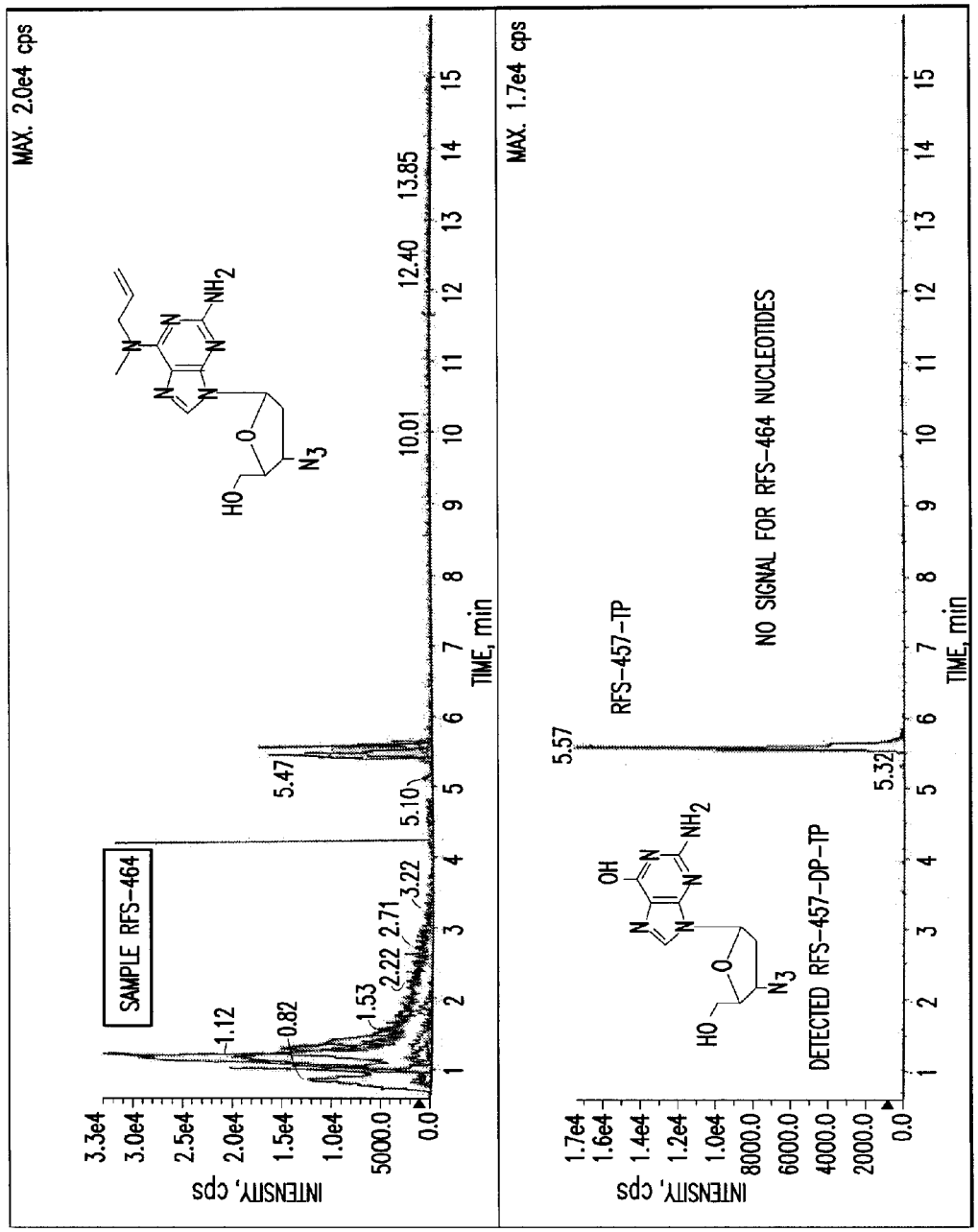
FIG. 3: LC/MS analysis of nucleotides formed after 4 hr incubation in PBM cells of 50 μM RS-464.

Incubation of RFS-464, which contains a 6-N-allyl, 6-N-Me group, in PBM cells resulted the detection of RFS-457-TP. No RFS-464, RFS-464-MP, RFS-464-DP, or RFS-464-TP were detected (FIG. 3).

Figure 4:
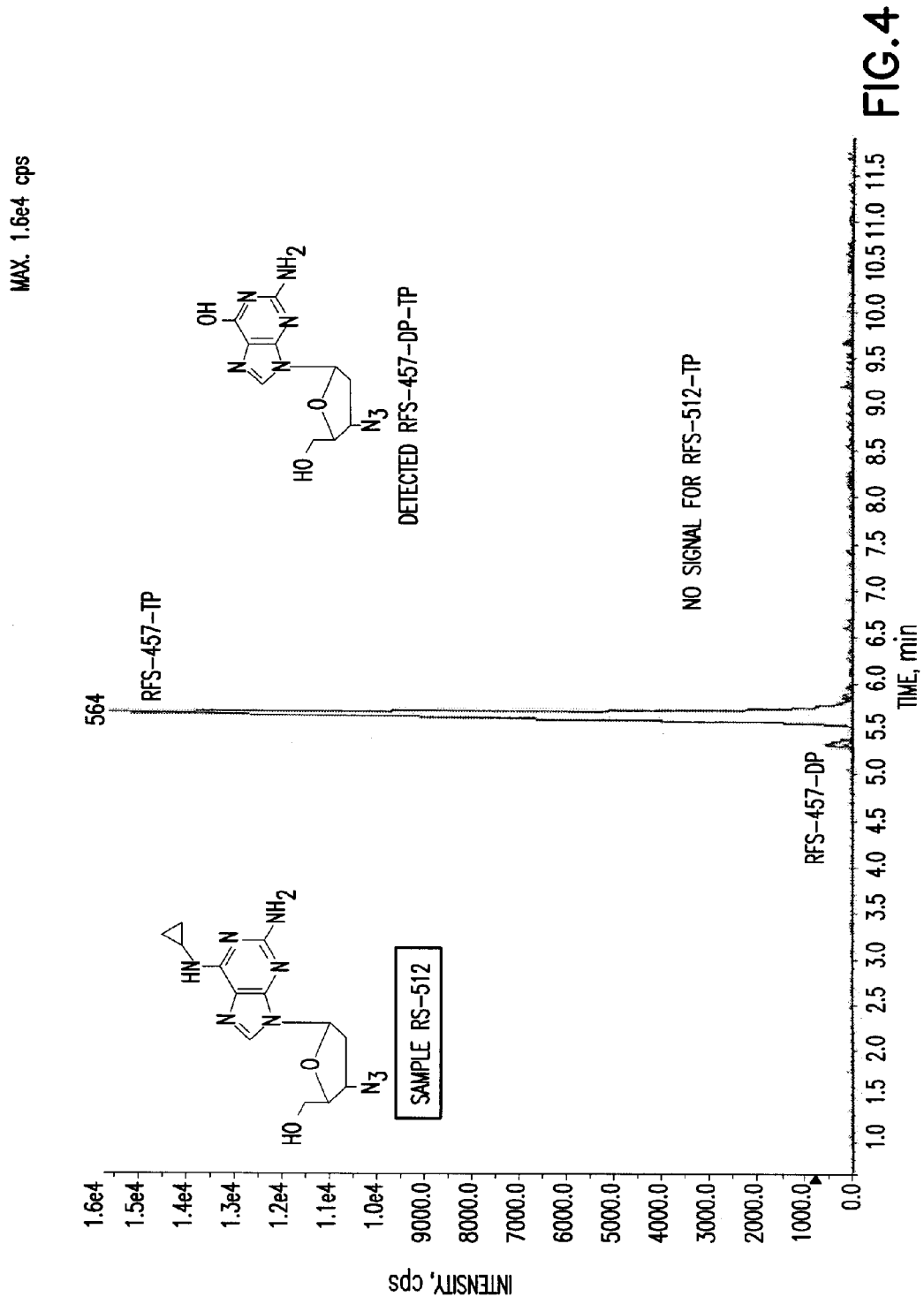
FIG. 4: LC/MS analysis of nucleotides formed after 4 hr incubation in PBM cells of 50 μM RS-512.

Incubation of RFS-512, which contains a 6-N-cyclopropyl group, in PBM cells resulted the detection of RFS-457-DP and RFS-457-TP. No RFS-512, RFS-512-MP, RFS-512-DP, or RFS-512-TP were detected (FIG. 4).

Figure 5:
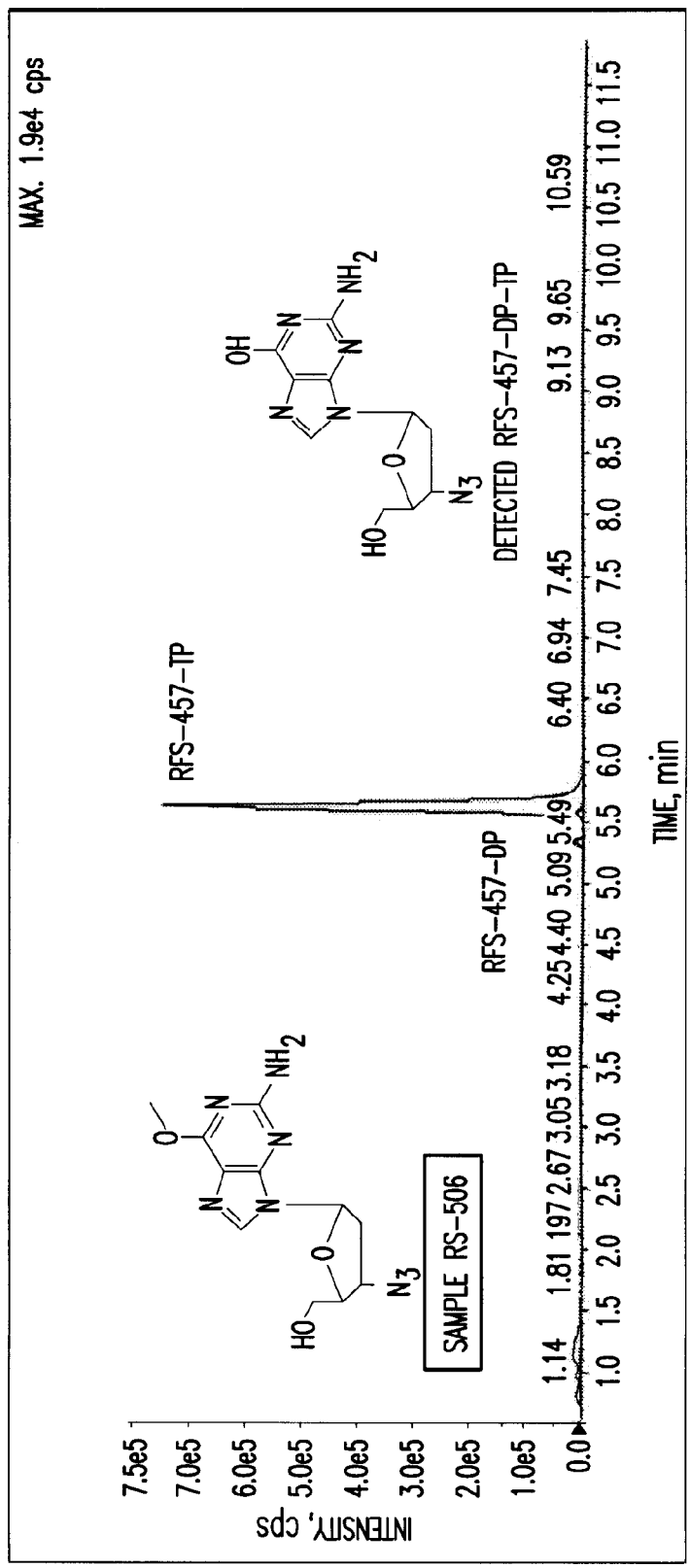
FIG. 5: LC/MS analysis of nucleotides formed after 4 hr incubation in PBM cells of 50 μM RS-506.
Figure 5:
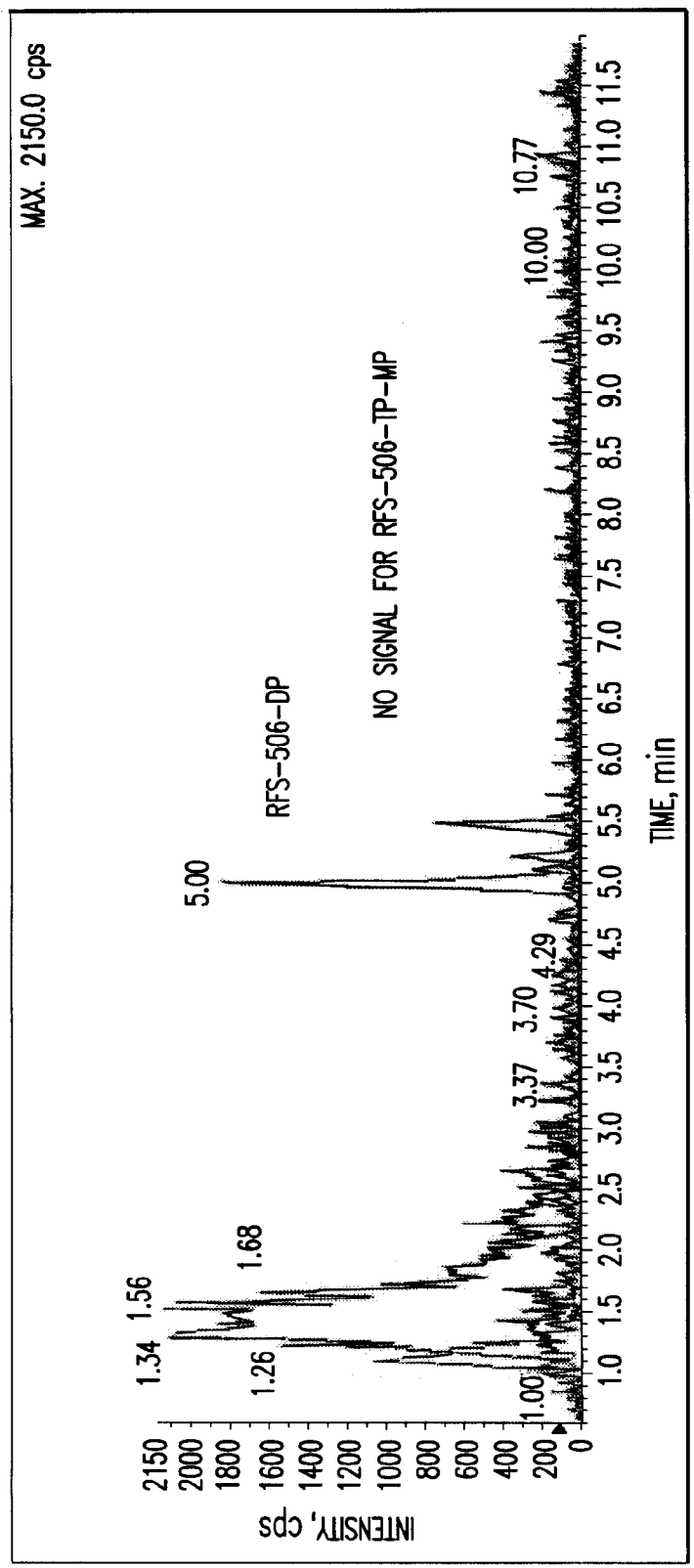

Incubation of RFS-506, which contains a 6-methoxy group, in PBM cells resulted the detection of RFS-506-DP, RFS-457-DP, and RFS-457-TP. No RFS-506, RFS-506-MP, or RFS-506-TP were detected (FIG. 5).

Figure 6:
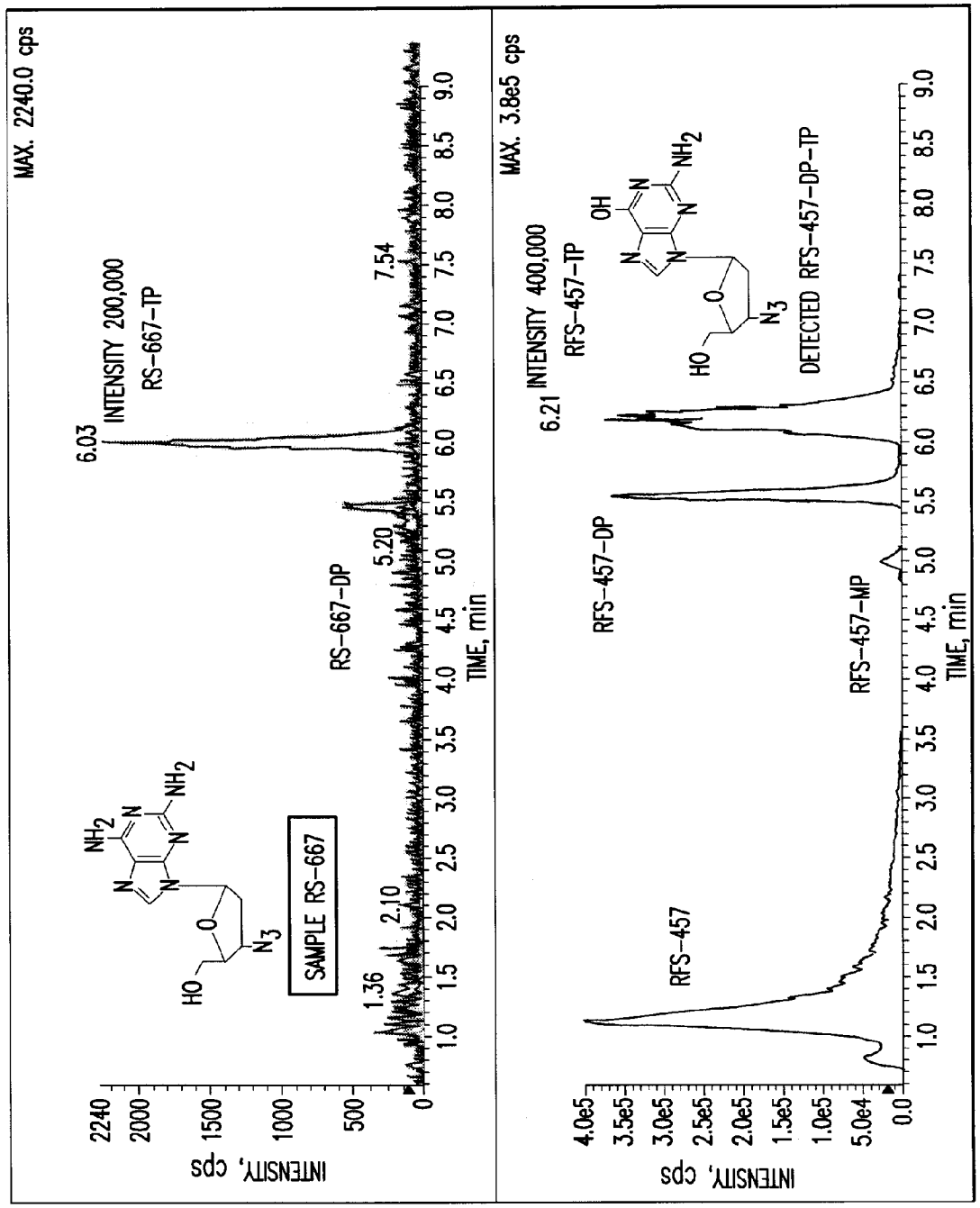
FIG. 6: LC/MS analysis of nucleotides formed after 4 hr incubation in PBM cells of 50 μM RS-667.

Incubation of RFS-667, which contains a 6-amino group, in PBM cells resulted the detection of RFS-457, RFS-457-MP, RFS-457-DP, RFS-457-TP RFS-667-DP, and RFS-667-TP. No RFS-667 or RFS-667-MP were detected (FIG. 6).

Figure 7:
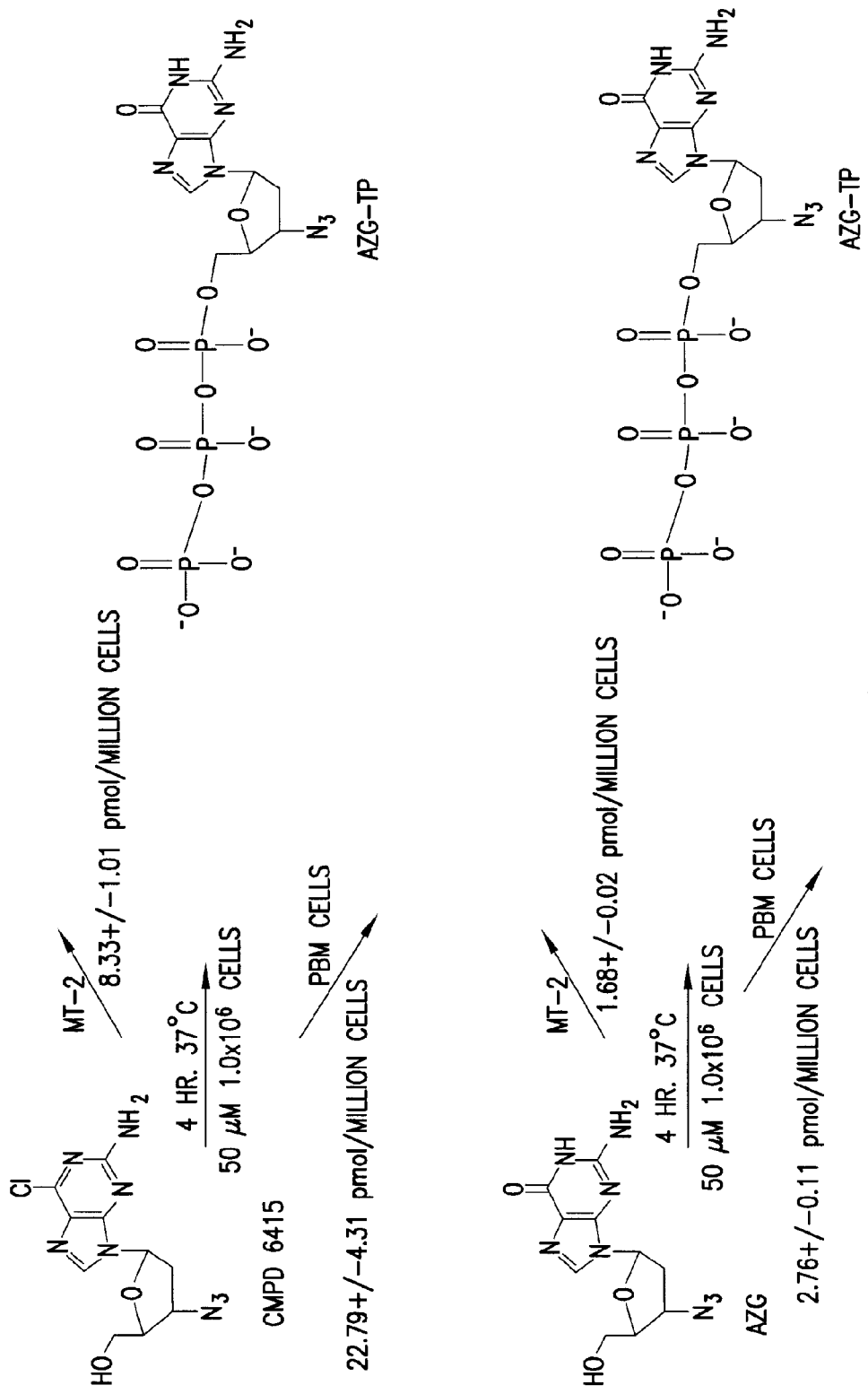
FIG. 7: AZG-TP levels in MT-2 and PBM cells after incubating with drug (either compound 6415 or RFS-457, also referred to herein as AZG) for 4 hr at 50 μM

Incubation of Compound 6415, which contains a 6-chloro group, in both PBM and MT-2 cells followed by an analysis of intracelluar triphosphates formed resulted the detection of RFS-457-TP. Compound 6415 was converted to AZG and AZG-TP in PBM and MT-2 cells. Negligible levels of 6415 were detected in MT-2 cells treated with drug for 30 min. Neither Compound 6415 nor its phosphates were detected in PBM cells (FIG. 7).

AZG-TP levels were higher in both MT-2 and PBM cells when they were treated with Compound 6415, which suggest that conversion to the triphosphate form occurred faster when Compound 6415 was used. Incubation of AZG at four different concentrations suggested that phosphorylation reaches steady state at 30 μM in MT-2. The ratio AZG-TP/dGTP was 5 times higher in MT-2 cells than in PBM cells. After 48 hr treatment with either AZG or 6415, all dNTP levels were increased (~doubled), but not dGTP levels, which suggests a competition for phosphorylation with AZG.

In order to determine if these 6-substituted compounds are converted to G analogs by the enzyme adenosine deaminase, a series of enzyme kinetics experiments were undertaken. As shown in Table 1, a representative number of 6-substituted nucleosides were found to be converted to the G analog by adenosine deaminase. Compound 69, a 6-N,N-dimethyl analog was found to be stable to adenosine deaminase under the conditions tested.

TABLE 1

Deamination of Nucleosides by Adenosine Deaminase.

| Structure | Compound Number | Extinction Coefficient at pH 7.4 | Deamination in 7 min (0.002 units Adenosine Deaminase) | Deamination in 120 min (0.2 units Adenosine Deaminase) |
| --- | --- | --- | --- | --- |
| [2'-deoxyadenosine structure] | 2'-deoxyadenosine | $\epsilon_{265} = 14.3$ mM$^{-1}$ cm$^{-1}$ | 59.30% | 105.50% |
| [2'-deoxyguanosine structure] | 2'-deoxyguanosine | $\epsilon_{265} = 9.6$ mM$^{-1}$ cm$^{-1}$ | below level of detection | below level of detection |

TABLE 1-continued

Deamination of Nucleosides by Adenosine Deaminase.

| Structure | Compound Number | Extinction Coefficient at pH 7.4 | Deamination in 7 min (0.002 units Adenosine Deaminase) | Deamination in 120 min (0.2 units Adenosine Deaminase) |
|---|---|---|---|---|
| (structure) | 69 | $\epsilon_{285} = 19.6$ mM$^{-1}$ cm$^{-1}$ | below level of detection | below level of detection |
| (structure) | 72 | $\epsilon_{285} = 9.6$ mM$^{-1}$ cm$^{-1}$ | 0.56% | 33.40% |
| (structure) | 62 | $\epsilon_{285} = 10.9$ mM$^{-1}$ cm$^{-1}$ | below level of detection | 7.60% |
| (structure) | 6415 | (RS457) $\epsilon_{265} = 5.6$ mM$^{-1}$ cm$^{-1}$ | 12.81 ± 1.57 | 240.53 ± 5.86 |

TABLE 1-continued

Deamination of Nucleosides by Adenosine Deaminase.

| Structure | Compound Number | Extinction Coefficient at pH 7.4 | Deamination in 7 min (0.002 units Adenosine Deaminase) | Deamination in 120 min (0.2 units Adenosine Deaminase) |
|---|---|---|---|---|
| (structure shown) | 70 | (RS457) $\epsilon_{265}$ = 5.6 mM$^{-1}$ cm$^{-1}$ | 0.55 ± 5.8 | 130.22 ± 4.72 |

2'-deoxyadenosine is also referred to herein as RFS-667. Compound 72 is also referred to herein as RFS-512. Compound 62 is also referred to herein as RFS-427. Compound 70 is also referred to herein as RFS-506.

Shown in Table 2 are the HIV and toxicity data for MP prodrug RS-788 and the parent nucleoside RS-667. In this case an increase in anti-HIV activity for RS-788 is noted at both the $EC_{50}$ and $EC_{90}$ however there is also an increase in toxicity relative to the parent nucleoside RS-667. This compound displays a 4300 and 3400-fold difference in $EC_{50}$ toward HIV and $IC_{50}$ toward PBM and CEM cells respectively.

TABLE 2

HIV and Toxicity data for MP prodrug RS-788 and the parent nucleoside RS-667

(structure shown)

RS-788 (n = 3; HIV assay)
HIV $EC_{50}$ = 0.009 µM
HIV $EC_{90}$ = 0.11 µM
PBM $IC_{50}$ = 38.3 µM
CEM $IC_{50}$ = 30.4 µM
Vero $IC_{50}$ > 100 µM
Parent nucleoside (RS-667)

Figure 8:
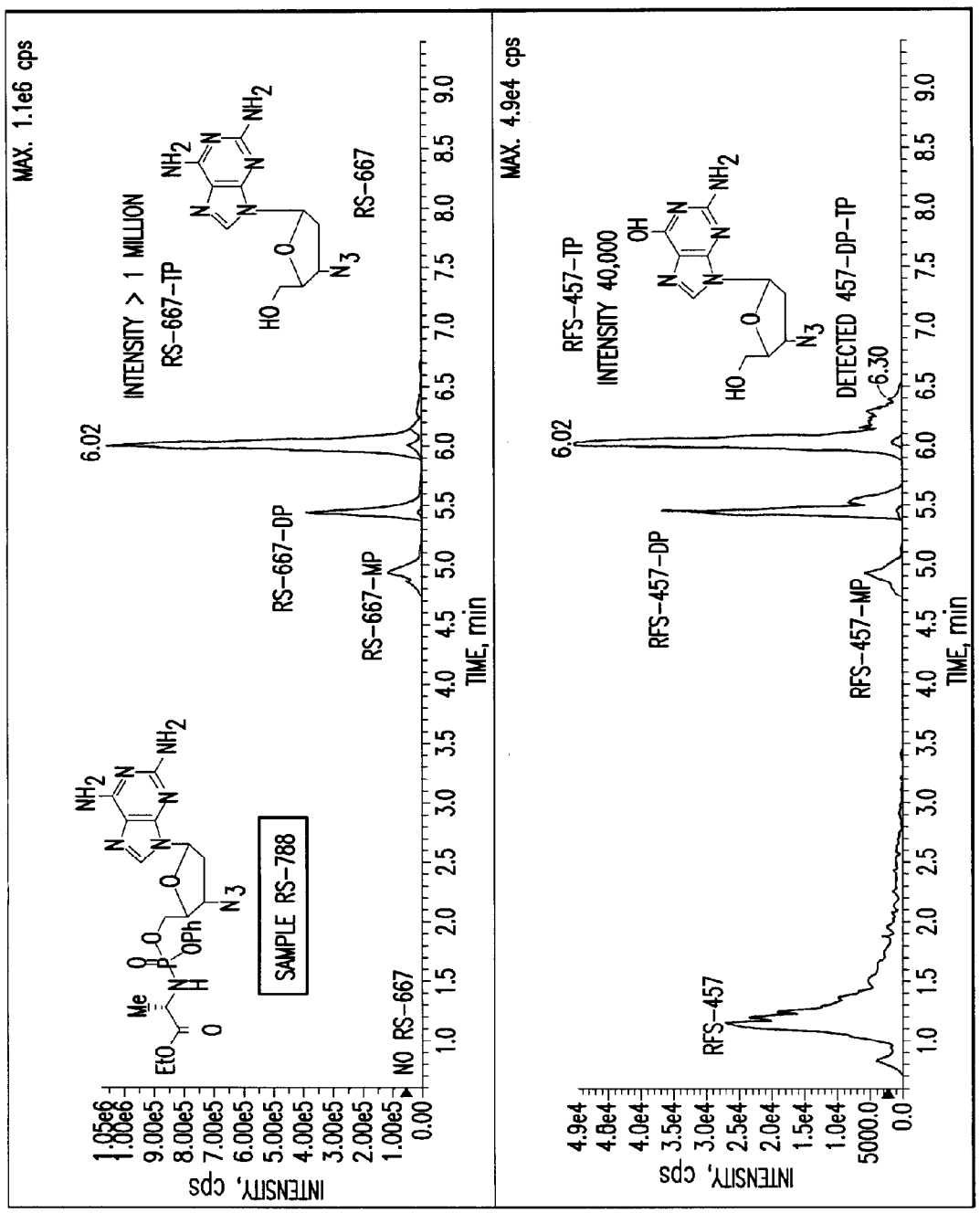
FIG. 8: LC/MS analysis of nucleotides formed after 4 hr incubation in PBM cells of 50 μM RS-788

$EC_{50}/EC_{90}$ = 0.074/0.36 µM
PBM $IC_{50}$ = 53.9 µM
CEM $IC_{50}$ > 100 µM
Vero $IC_{50}$ > 100 µM Incubation of RS-788, which contains a 6-amino group and a 5'-MP prodrug, in PBM cells resulted the detection of RFS-457-MP, RFS-457-DP, and RFS-457-TP. However, in contrast to the incubation of RS-667, very high levels of RS-667 MP, RS-667DP, and RS-667TP were detected (FIG. 8). The high levels of intercellular RS-667-TP produced upon incubation of the MP prodrug RS-788 indicate that the MP prodrug has efficiently limited or stopped the conversion of the 6-amino group to 6-OH.

Figure 9:
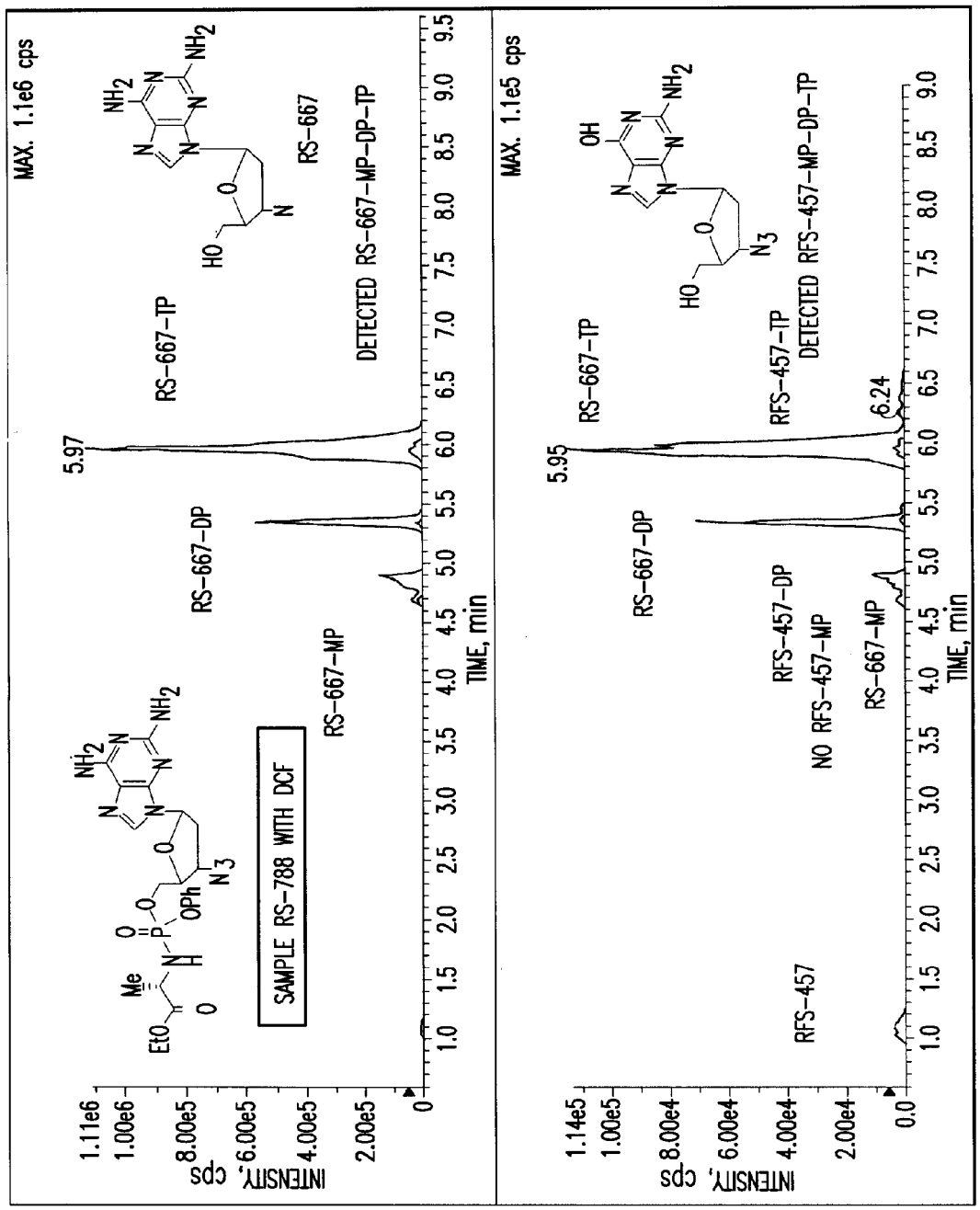
FIG. 9: LC/MS analysis of nucleotides formed after 4 hr incubation in PBM cells of 50 μM RS-788 pretreated with deoxycoformycin (DCF).

Incubation of RS-788, which contains a 6-amino group and a 5'-MP prodrug, in PBM cells which were pretreated with deoxycoformycin, a known adenosine deaminase inhibitor, resulted the detection of very low levels of RFS-457-MP, RFS-457-DP, and RFS-457-TP. However, again in contrast to the incubation of RS-667, very high levels of RS-667-MP, RS-667-DP, and RS-667-TP were detected (FIG. 9).

The metabolism of (-)-β-D-2,6-diaminopurine dioxolane (DAPD) in PHA-stimulated human PBMCs and CEM cells was previously assessed (Antimicrob. Agents Chemother. 2001, 45, 158-165). In this previous study DAPD was found to readily deaminate to (-)-β-D-dioxolane guanine (DXG). While both DXG and DAPD were detected, DAPD levels in PBMCs were 27-fold higher than the level of DAPD, determined in CEM cells; the level of DXG was roughly the same in both cell types. The intracellular levels of DAPD and DXG and their phosphorylated derivatives were quantitated in the same previous study. No phosphorylation of DAPD to the corresponding mono-, di-, or triphosphate forms was detected in either cell type. It was shown that DAPD was deaminated to DXG and was subsequently phosphorylated to DXG-TP.

Figure 10:
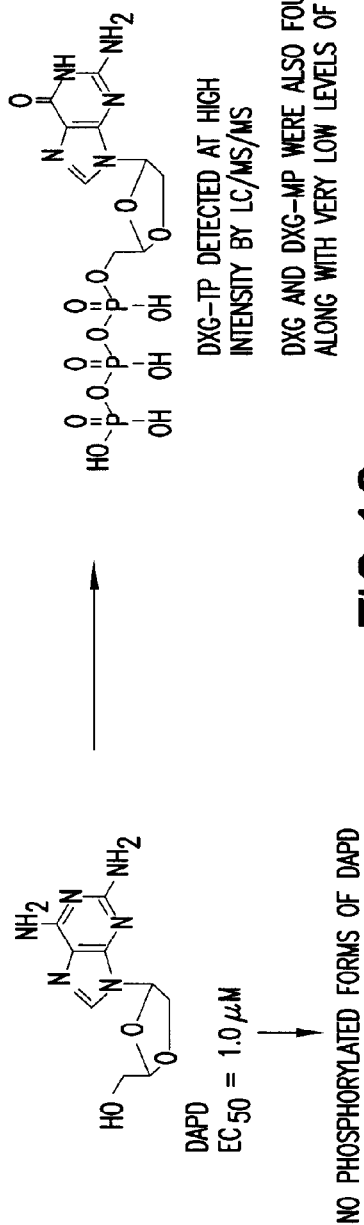
FIG. 10: LC/MS analysis of nucleotides formed after 4 hr incubation in PBM cells of 50 μM (-)-β-D-2,6-diaminopurine dioxolane (DAPD).

Reexamination of the intracellular metabolism of DAPD, which contains a 6-amino group, at 50 µM for 4 h in PBM cells at 37° C. resulted the detection of high levels of DXG-TP in addition to DXG and DXG-MP. Low levels of DAPD were observed however, no phosphorylated forms of DAPD were detected (FIG. 10).

Shown in Table 3 are the HIV and toxicity data for DAPD-MP prodrug RS-864 and the parent nucleoside DAPD. In this case an increase in anti-HIV activity for RS-864 is noted at both the $EC_{50}$ and $EC_{90}$ however there is also a slight increase in toxicity relative to the parent nucleoside DAPD.

TABLE 3

HIV and Toxicity data for MP prodrug RS-864 and the parent nucleoside DAPD

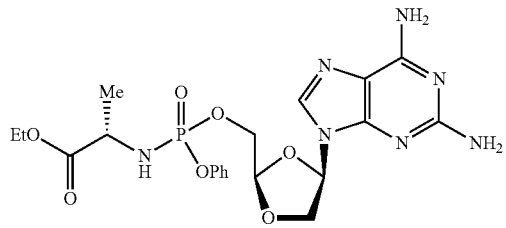

RS-864 (n = 2; HIV assay)
HIV $EC_{50}$ = 0.24 µM
HIV $EC_{90}$ = 1.3 µM
PBM $IC_{50}$ = 66.5% @ 100 µM
CEM $IC_{50}$ > 100 µM
Vero $IC_{50}$ > 100 µM
Parent nucleoside (DAPD)

Figure 11:
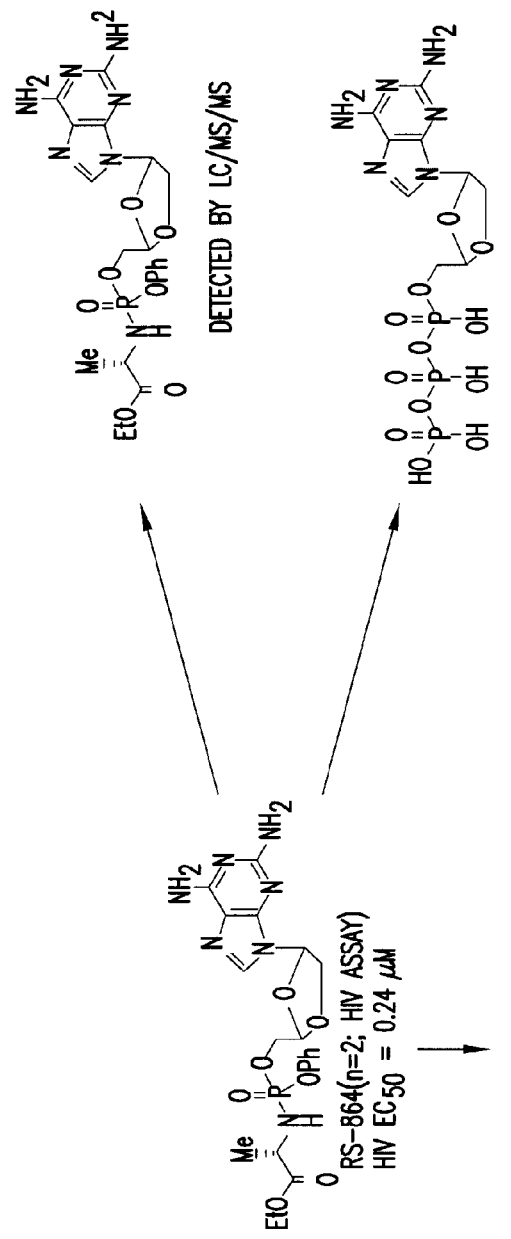
FIG. 11: LC/MS analysis of nucleotides formed after 4 hr incubation in PBM cells of 50 μM RS-864.

$EC_{50}/EC_{90}$ = 1.0/6.5 µM
PBM $IC_{50}$ = >100 µM
CEM $IC_{50}$ > 100 µM
Vero $IC_{50}$ > 100 µM Incubation of RS-864, which contains a 6-amino group and a 5'-MP prodrug, in PBM cells resulted the detection of low levels of DXG, DXG-MP, and DXG-TP (FIG. 11). However, in contrast to the incubation of DAPD, very high levels of DAPD-TP were detected. In addition, low levels of DAPD, DAPD-MP, DAPD-DP were also observed. The high levels of intercellular DAPD-TP produced upon incubation of the DAPD-MP prodrug indicate that the MP prodrug has efficiently limited or stopped the conversion of the 6-amino group to 6-OH.

Example 8

Anti-HIV (in PBM Cells) Assay

Having demonstrated above that the nucleoside analogs of the compounds are converted to 6-hydroxy analogs, and that the monophosphate analogs of the nucleosides resist this conversion, it is now relevant to discuss the biological activity of the compounds described herein.

Anti-HIV-1 activity of the compounds was determined in human peripheral blood mononuclear (PBM) cells as described previously (see Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D. C. Antimicrob. Agents Chemother. 1992, 36, 2423; Schinazi R. F., Sommadossi J.-P., Saalmann V., Cannon D., Xie M.-Y., Hart G., Smith G., Hahn E. Antimicrob. Agents Chemother. 1990, 34, 1061). Stock solutions (20-40 mM) of the compounds were prepared in sterile DMSO and then diluted to the desired concentration in growth medium. Cells were infected with the prototype HIV-$1_{LAI}$ at a multiplicity of infection of 0.01. Virus obtained from the cell supernatant was quantified on day 6 after infection by a reverse transcriptase assay using $(rA)_n \cdot (dT)_{12-18}$ as template-primer. The DMSO present in the diluted solution (<0.1%) had no effect on the virus yield. AZT was included as positive control. The antiviral $EC_{50}$ and $EC_{90}$ were obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11).

Example 9

Assess Incorporation of Nucleoside-TPs by HIV-1 RT i) Protein Expression and Purification: HIV-1 RT (xxLAI background) (see Shi C, Mellors J W. A recombinant retroviral system for rapid in vivo analysis of human immunodeficiency virus type 1 susceptibility to reverse transcriptase inhibitors. Antimicrob Agents Chemother. 1997; 41:2781-5) was over-expressed in bacteria using the p6HRT-PROT expression vector and purified to homogeneity as described previously (see Le Grice S F, Gruninger-Leitch F. Rapid purification of homodimer and heterodimer HIV-1 reverse transcriptase by metal chelate affinity chromatography. Eur J Biochem. 1990; 187: 307-14; Le Grice S F, Cameron C E, Benkovic S J. Purification and characterization of human immunodeficiency virus type 1 reverse transcriptase. Methods Enzymol. 1995; 262:130-44). The protein concentration of the purified enzymes was determined spectrophotometrically at 280 nm using an extinction co-efficient ($\epsilon$280) of 260450M-1cm-1. Active site concentrations of RT were calculated from pre-steady-state burst experiments, as described previously (see Kati W M, Johnson K A, Jerva L F, Anderson K S. Mechanism and fidelity of HIV reverse transcriptase. J Biol. Chem. 1992; 267: 25988-97). All reactions described below were carried out using active site concentrations.

ii) Pre-steady-state Kinetic Analyses: A $[\gamma^{32}P]$-ATP 5'-end labeled 20 nucleotide DNA primer (5'-TCGGGCGCCACT-GCTAGAGA-3') annealed to a 57 nucleotide DNA template (5'-CTCAGACCCTTTTAGTCAGAATGGAAANTCTCT-AGCAGTGGCGCCCGAACAGGGACA-3') was used in all experiments. The DNA templates contained either a T or C at position 30 (N), which allowed evaluation of the kinetics of single nucleotide incorporation using the same 20 nucleotide primer. Rapid quench experiments were carried out using a Kintek RQF-3 instrument (Kintek Corporation, Clarence, Pa.). In all experiments, 300 nM RT and 60 nM DNA template/primer (T/P) were pre-incubated in reaction buffer (50 mM Tris-HCl pH 7.5, 50 mM KCl) prior to mixing with an equivalent volume of nucleotide in the same reaction buffer containing 20 mM $MgCl_2$. Reactions were terminated at times ranging from 10 ms to 30 min by quenching with 0.5M EDTA, pH 8.0. The quenched samples were mixed with an equal volume of gel loading buffer (98% deionized formamide, 10 mM EDTA and 1 mg/mL each of bromophenol blue and xylene cyanol), denatured at 85° C. for 5 min, and the products were separated from the substrates on a 7M urea-16% polyacrylamide gel. Product formation was analyzed using a Bio-Rad GS525 Molecular Imager (Bio-Rad Laboratories, Inc., Hercules, Calif.).

iii) Data Analysis: Data obtained from kinetic assays was fitted by nonlinear regression using Sigma Plot software (Jandel Scientific) with the appropriate equations (see Johnson K A. Rapid quench kinetic analysis of polymerases, adenosinetriphosphatases, and enzyme intermediates. Methods Enzymol. 1995; 249:38-61). The apparent burst rate constant (kobs) for each particular concentration of dNTP was determined by fitting the time courses for the formation of product to the equation: [product]=A[1−exp(−kobst)], where A represents the burst amplitude. The turnover number (kpol) and apparent dissociation constant for dNTP ($K_d$) was obtained by plotting the apparent catalytic rates, kobs, against dNTP concentrations and fitting the data with the following hyperbolic equation: kobs=(kpol[dNTP])/([dNTP]+$K_d$).

Example 10

Assess Anti-HIV Activity and Cellular Toxicity of 6-Substituted-2-Amino Purine Nucleoside Monophosphate Prodrugs i) Viruses: Stock virus was prepared using the xxHIV-1LAI clone75 by electroporating (Gene Pulser; Bio-Rad) 5 to 10 µg of plasmid DNA into $1.3 \times 10^7$ MT-2 cells. At 7 days post-transfection, cell-free supernatant was harvested and stored at −80° C. The genotype of stock viruses was confirmed by extraction of RNA from virions, treatment of the extract with DNase I, amplification of the full-length coding region (amino acids 1 to 560) of RT by RT-PCR, purification of the PCR product, and sequence determination of the PCR product using a Big Dye terminator kit (v. 3.1) on an ABI 3100 automated DNA sequencer (Applied Biosystems, Foster City, Calif.). The 50% tissue culture infective dose ($TCID_{50}$) for the virus stock was determined for MT-2 cells, P4/R5 cells or PBM cells by three-fold endpoint dilution assays (six wells per dilution) and calculated using the Reed and Muench equation (see Reed L J, Muench H. A simple method of estimating fifty percent endpoints. Am. J. Hyg. 1938; 27:493-497).

ii) Single-Replication-Cycle Drug Susceptibility Assay: In a 96-well plate, two- or three-fold serial dilutions of an inhibitor were added to P4/R5 cells in triplicate. Cells were infected with the amount of virus that yielded a relative light unit value of 100 in the no-drug, virus-infected control wells. At 48 h post-infection, a cell lysis buffer and luminescent substrate (Gal-Screen; Tropix/Applied Biosystems) was added to each well, and relative light unit values were determined using a luminometer (ThermoLabSystems, Waltham, Mass.). Inhibition of virus replication was calculated as the concentration of compound required to inhibit virus replication by 50% ($EC_{50}$).

iii) Multiple-Replication-Cycle Drug Susceptibility Assay: In a 96-well plate, three-fold serial dilutions of an inhibitor were added to MT-2 cells in triplicate. The cells were infected at a multiplicity of infection of 0.01 as determined by endpoint dilution in MT-2 cells. At 7 days post-infection, culture supernatants were harvested and treated with 0.5% Triton X-100. The p24 antigen concentration in the supernatants was determined using a commercial enzyme-linked immunosorbent assay (DuPont, NEN Products, Wilmington, Del.). $EC_{50}$ values were calculated as described above.

iv) Drug Susceptibility Assays in PBM Cells: PBM cells were isolated by Ficoll-Hypaque discontinuous gradient centrifugation from healthy seronegative donors, as described previously (see Schinazi R F, Cannon D L, Arnold B H, Martino-Saltzman D. Combinations of isoprinosine and 3'-azido-3'-deoxythymidine in lymphocytes infected with human immunodeficiency virus type 1. Antimicrob. Agents Chemother. 1988; 32:1784-1787; Schinazi R F, Sommadossi J P, Saalmann V, Cannon D L, Xie M Y, Hart G C, Smith G A. Hahn E. F. Activities of 3'-azido-3'-deoxythymidine nucleotide dimers in primary lymphocytes infected with human immunodeficiency virus type 1. Antimicrob. Agents Chemother. 1990; 34:1061-1067). Cells were stimulated with phytohemagglutinin A (PHA, Difco, Sparks, Md.) for 2-3 days prior to use. Infections were done in bulk for 0.1 h, either with 100 $TCID_{50}/1 \times 10^7$ cells for a flask (T25) assay or with 200 $TCID_{50}/6 \times 10^7$ cells/well for the 24-well plate assay. Cells were added to a plate or a flask containing a 10-fold serial dilution of the test compound. At 5 days post-infection, culture supernatants were harvested and treated with 0.5% Triton X-100. The p24 antigen concentration in the supernatants was determined as described above. $EC_{50}$ and fold-resistance values were calculated as described above.

v) Cellular Toxicity Assays: 6-Substituted-2-amino purine nucleoside monophosphate prodrugs were evaluated for their potential toxic effects on P4/R5 cells, MT-2 cells and uninfected PHA-stimulated human PBM cell. Log-phase P4/R5, MT-2, and PHA-stimulated human PBM cells were seeded at $5 \times 10^3$ to $5 \times 10^4$ cells/well in 96-well cell culture plates containing 10-fold serial dilutions of the test drug. The cultures were incubated for 2-4 days, after which 3-(4,5-dimethylthi-azol-2-yl)-2,5-diphenyltetrazolium bromide (MTT) dye solution (Promega, Madison, Wis.) were added to each well and incubated overnight. The reaction was stopped with stop solubilization solution (Promega, Madison, Wis.) and plates were read at a wavelength of 570 nm. The median 50% cytotoxic concentration ($CC_{50}$) was determined from the concentration-response curve using the median effect method.

Example 11

Assess Activity of 6-Substituted-2-Amino Purine Nucleoside Monophosphate Prodrugs Against Drug-Resistant HIV Analogs identified above as having improved activity compared with the parent analog, and less cellular toxicity, were further evaluated for activity against a panel of drug resistant viruses. The drug resistant viruses used in this study included HIV-$1_{K65R}$, HIV-$1_{K70E}$, HIV-$1_{L74V}$, HIV-$1_{M184V}$, HIV-$1_{AZT2}$, HIV-$1_{AZT3}$, HIV-$1_{AZT7}$, HIV-$1_{AZT9}$, HIV-$1_{Q151M}$ and HIV-$1_{69Insertion}$. The genotypes of these viruses and mutations in HIV-RT are described in FIG. 12. All of these mutant viruses were generated in our HIV-1xxLAI clone.

Example 12

Assess Activity of 6-Substituted-2-Amino Purine Nucleoside Monophosphate Prodrugs Against Drug-Resistant HIV i) Viruses and Drug Susceptibility Assays: Virus stocks were prepared as described above. Drug susceptibility assays were performed using the single- and multiple-replication-cycle assays also described above. Inhibition of virus replication was calculated as the concentration of compound required to inhibit virus replication by 50% ($EC_{50}$). Fold resistance values were determined by dividing the $EC_{50}$ for mutant HIV-1 by the $EC_{50}$ for WT HIV-1.

ii) Statistical analysis: To determine if fold-resistance values are statistically significant, $EC_{50}$ values from at least three independent experiments were log 10 transformed and compared using a two-sample Student's t test with Sigma Stat software (Jandel Scientific). P values less than 0.05 were considered to be statistically significant.

Example 13

Assess Incorporation and Excision of Nucleotides by Mutant HIV-1 RTs i) Enzymes: The following mutant HIV-1 RT enzymes can be used in this study: K65R RT, K70E RT, L74V RT, M184V RT, AZT2 RT, AZT3 RT, Q151M RT and 69Insert RT. E. coli protein expression vectors for each of these mutant RTs can be developed, and protein expression and purification can be performed as described previously. Protein concentration and active site concentration is determined as described above.

ii) Kinetic Analyses of Nucleotide Incorporation: Pre-steady-state kinetic analyses can be used to determine the kinetic parameters Kd and kpol for each novel nucleoside-TPs for K65R, K70E RT, L74V RT, M184V RT and Q151M RT. Experimental design and data analysis can be carried out as described above.

iii) Excision Assays: The ATP-mediated phosphorolytic excision of the novel analogs from chain-terminated template/primer can be carried out using WT RT, AZT2 RT, AZT3 RT and 69Insert RT. The 20 nucleotide DNA primer described above can be 5'-end labeled with [$\gamma^{32}$P]-ATP and then annealed to the appropriate 57 nucleotide DNA template. The 3'-end of the primer can be chain-terminated by incubation with WT RT and 100 µM of the appropriate modified nucleotide analog for 30 min at 37° C. The $^{32}$P-labeled, chain-terminated 21 nucleotide primer can be further purified by extraction of the appropriate band after 7M urea-16% acrylamide denaturing gel electrophoresis. The purified chain-terminated primer can then be re-annealed to the appropriate DNA template for use in phosphorolysis experiments. The phosphorolytic removal of nucleoside-MP can be achieved by incubating 300 nM (active site) WT or mutant RT with 60 nM of the chain-terminated T/P complex of interest in 50 mM Tris-HCl pH 8.0, 50 mM KCl. The reaction can be initiated by the addition of 3.0 mM ATP and 10 mM $MgCl_2$. Inorganic pyrophosphatase (0.01 U) can be present throughout the reaction. After defined incubation periods, aliquots can be removed from the reaction tube and quenched with equal volumes of gel loading dye (98% deionized formamide, 10 mM EDTA and 1 mg/mL each of bromophenol blue and xylene cyanol). Products can be separated by denaturing gel electrophoresis, and the disappearance of substrate coincident with formation of product can be analyzed using a Bio-Rad GS525 Molecular Imager. Data were fit to the following single exponential equation to determine the apparent rate (kATP) of ATP-mediated excision: [product]=A[exp(-kATPt)], where A represents the amplitude for product formation. Dead-end complex formation can be determined as described previously (see Meyer P R, Matsuura S E, Mian A M, So A G, Scott W A. A mechanism of AZT resistance: an increase in nucleotide-dependent primer unblocking by mutant HIV-1 reverse transcriptase. Mol Cell. 1999; 4:35-43; Sluis-Cremer N, Arion D, Parikh U, Koontz D, Schinazi R F, Mellors J W, Parniak M A. The 3'-azido group is not the primary determinant of 3'-azido-3'-deoxythymidine (AZT) responsible for the excision phenotype of AZT-resistant HIV-1. J Biol Chem. 2005; 280: 29047-52).

Example 14

Mitochondrial Toxicity Assays in HepG2 Cells i) Effect of 6-Substituted-2-amino purine nucleoside monophosphate prodrugs on Cell Growth and Lactic Acid Production: The effect on the growth of HepG2 cells was determined by incubating cells in the presence of 0 µM, 0.1 µM, 1 µM, 10 µM and 100 µM drug. Cells ($5\times10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the nucleoside analogs on lactic acid production, HepG2 cells from a stock culture were diluted and plated in 12-well culture plates at $2.5\times10^4$ cells per well. Various concentrations (0 µM, 0.1 µM, 1 µM, 10 µM and 100 µM) of nucleoside analog were added, and the cultures were incubated at 37° C. in a humidified 5% $CO_2$ atmosphere for 4 days. At day 4 the number of cells in each well were determined and the culture medium collected. The culture medium was filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of 6-substituted-2-amino purine nucleoside monophosphate prodrug analogs would indicate a drug-induced cytotoxic effect.

ii) Effect on 6-Substituted-2-amino purine nucleoside monophosphate prodrugs on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay was used in all studies described in this application that determine the effect of nucleoside analogs on mitochondrial DNA content. In this assay, low-passage-number HepG2 cells were seeded at 5,000 cells/well in collagen-coated 96-well plates. Nucleoside monophosphate analogs were added to the medium to obtain final concentrations of 0 µM, 0.1 µM, 10 µM and 100 µM. On culture day 7, cellular nucleic acids were prepared by using commercially available columns (RNeasy 96 kit; Qiagen). These kits co-purify RNA and DNA, and hence, total nucleic acids were eluted from the columns. The mitochondrial cytochrome c oxidase subunit II (COXII) gene and the β-actin or rRNA gene were amplified from 5 µl of the eluted nucleic acids using a multiplex Q-PCR protocol with suitable primers and probes for both target and reference amplifications. For COXII the following sense, probe and antisense primers are used, respectively: 5'-TGCCCGCCAT-CATCCTA-3',5'-tetrachloro-6-carboxyfluorescein-TCCT-CATCGCCCTCCCATCCC-TAMRA-3' and 5'-CGTCTGT-TATGTAAAGGATGCGT-3'. For exon 3 of the β-actin gene (GenBank accession number E01094) the sense, probe, and antisense primers are 5'-GCGCGGCTACAGCTTGA-3',5'-6-FAMCACCACGGCCGAGCGGGATAMRA-3' and 5'-TCTCCTTAATGTCACGCACGAT-3', respectively. The primers and probes for the rRNA gene are commercially available from Applied Biosystems. Since equal amplification efficiencies were obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample–CT for target control)–(CT for average reference test–CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

iii) Electron Microscopic Morphologic Evaluation: NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells. Biochem. Pharmacol. 1996, 52, 1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, X J Zhou, J P Sommadossi, V M Darley-Usmar. Differential effects of antiretroviral nucleoside analogs on mitochondrial function in HepG2 cells. Antimicrob. Agents Chemother. 2000, 44, 496-503). For example, electron micrographs of HepG2 cells incubated with 10 µM fialuridine (FIAU; 1,2'-deoxy-2'-fluoro-1-D-arabinofuranosly-5-iodo-uracil) showed the presence of enlarged mitochondria with morphological changes consistent with mitochondrial dysfunction. To determine if 6-substituted-2-amino purine nucleoside monophosphate prodrugs promoted morphological changes in mitochondria, HepG2 cells ($2.5 \times 10^4$ cells/mL) were seeded into tissue cultures dishes (35 by 10 mm) in the presence of 0 µM, 0.1 µM, 1 µM, 10 µM and 100 µM nucleoside analog. At day 8, the cells were fixed, dehydrated, and embedded in Eponas described previously. Thin sections were prepared, stained with uranyl acetate and lead citrate, and then examined using transmission electron microscopy.

Example 15

Mitochondrial Toxicity Assays in Neuro2A Cells

To estimate the potential of nucleoside analogs to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. Antimicrob. Agents Chemother. 2005, 49, 1994-2001). The concentrations necessary to inhibit cell growth by 50% ($CC_{50}$) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. In all experiments, ddC and AZT can be used as control nucleoside analogs.

Example 16

Effect of Nucleotide Analogs on the DNA Polymerase and Exonuclease Activities of Mitochondrial DNA Polymerase γ i) Purification of Human Polymerase γ: The recombinant large and small subunits of polymerase γ can be purified as described previously (see Graves S W, Johnson A A, Johnson K A. Expression, purification, and initial kinetic characterization of the large subunit of the human mitochondrial DNA polymerase. Biochemistry. 1998, 37, 6050-8; Johnson A A, Tsai Y, Graves S W, Johnson K A. Human mitochondrial DNA polymerase holoenzyme: reconstitution and characterization. Biochemistry 2000; 39: 1702-8). The protein concentration can be determined spectrophotometrically at 280 nm, with extinction coefficients of 234,420, and 71,894 M-1 cm$^{-1}$ for the large and the small subunits of polymerase γ, respectively.

ii) Kinetic Analyses of Nucleotide Incorporation: Pre-steady-state kinetic analyses can be carried out to determine the catalytic efficiency of incorporation (k/K) for DNA polymerase γ for nucleoside-TP and natural dNTP substrates. This allows determination of the relative ability of this enzyme to incorporate modified analogs and predict toxicity. Pre-steady-state kinetic analyses of incorporation of nucleotide analogs by DNA polymerase γ can be carried out essentially as described previously (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004, 62, 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004, 48, 1300-6). Briefly, a pre-incubated mixture of large (250 nM) and small (1.25 mM) subunits of polymerase γ and 6 0 nM DNA template/primer in 50 mM Tris-HCl, 100 mM NaCl, pH 7.8, can be added to a solution containing $MgCl_2$ (2.5 mM) and various concentrations of nucleotide analogs. Reactions can be quenched and analyzed as described previously. Data can be fit to the same equations as described above.

iii) Assay for Human Polymerase γ 3' 5' Exonuclease Activity: The human polymerase γ exonuclease activity can be studied by measuring the rate of formation of the cleavage products in the absence of dNTP. The reaction can be initiated by adding $MgCl_2$ (2.5 mM) to a pre-incubated mixture of polymerase γ large subunit (40 nM), small subunit (270 nM), and 1,500 nM chain-terminated template/primer in 50 mM Tris-HCl, 100 mM NaCl, pH 7.8, and quenched with 0.3M EDTA at the designated time points. All reaction mixtures can be analyzed on 20% denaturing polyacrylamide sequencing gels (8M urea), imaged on a Bio-Rad GS-525 molecular image system, and quantified with Molecular Analyst (Bio-Rad). Products formed from the early time points can be plotted as a function of time. Data were fitted by linear regression with Sigma Plot (Jandel Scientific). The slope of the line can be divided by the active enzyme concentration in the reaction to calculate the kexo for exonuclease activity (see Murakami. E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004; 62: 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004; 48: 1300-6).

Example 17

Assay for Bone Marrow Cytotoxicity

Primary human bone marrow mononuclear cells were obtained commercially from Cambrex Bioscience (Walkersville, Md.). CFU-GM assays were carried out using a bilayer soft agar in the presence of 50 units/mL human recombinant granulocyte/macrophage colony-stimulating factor, while BFU-E assays used a methylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment was performed in duplicate in cells from three different donors. AZT was used as a positive control. Cells were incubated in the presence of the compound for 14-18 days at 37° C. with 5% $CO_2$, and colonies of greater than 50 cells are counted using an inverted microscope to determine $IC_{50}$. The 50% inhibitory concentration ($IC_{50}$) was obtained by least-squares linear regression analysis of the logarithm of drug concentration versus BFU-E survival fractions. Statistical analysis was performed with Student's t test for independent non-paired samples.

Example 18

Anti-HBV Assay

The anti-HBV activity of the compounds was determined by treating the AD-38 cell line carrying wild type HBV under the control of tetracycline (see Ladner S. K., Otto M. J., Barker C. S., Zaifert K., Wang G. H., Guo J. T., Seeger C. & King R. W. *Antimicrob. Agents Chemother.* 1997, 41, 1715-20). Removal of tetracycline from the medium [Tet (−)] results in the production of HBV. The levels of HBV in the culture supernatant fluids from cells treated with the compounds were compared with that of the untreated controls. Control cultures with tetracycline [Tet (+)] were also maintained to determine the basal levels of HBV expression. 3TC was included as positive control.

Example 19

Cytotoxicity Assay

The toxicity of the compounds can be assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide can be included as positive cytotoxic control, and untreated cells exposed to solvent can be included as negative controls. The cytotoxicity $IC_{50}$ can be obtained from the concentration-response curve using the median effective method described previously (see Chou T.-C. & Talalay P. *Adv. Enzyme Regul.* 1984, 22, 27-55; Belen' kii M. S. & Schinazi R. F. *Antiviral Res.* 1994, 25, 1-11).

Example 20

Adenosine Deaminase Assay

To determine the propensity for deamination of the 6-substituted-2-amino purine nucleoside monophosphate prodrugs by adenosine deaminase, nucleoside compounds were incubated with the commercially available purified enzyme, and the reaction was followed spectrophotometrically. Reaction conditions were 50 mM potassium phosphate, pH 7.4, with 50 µM nucleoside analog in 0.5 mL at 25° C. Reaction time was 7 minutes with 0.002 units of enzyme and 120 minutes with 0.2 units of enzyme. (The unit definition of adenosine deaminase is one unit will deaminate 1.0 µmol of adenosine to inosine per minute at pH 7.5 at 25° C.) Deoxyadenosine was the positive control which was 59% deaminated under the given conditions in 7 minutes with 0.002 units of enzyme. Deoxyguanosine was the negative control. Optical density was measured at 265 nm or 285 nm. The difference in optical density between the beginning and the end of the experiment was divided by the extinction coefficient then multiplied by the volume of the reaction to determine the number of mols of substrate transformed into product. Mols of product were divided by mols of substrate equivalent to a 100% complete reaction then multiplied by 100 to obtain percent deamination. The limit of detection was 0.001 optical density units.

Example 21

Selection of Resistant Viruses to Nucleotide Monophosphate Prodrugs

Peripheral blood mononuclear (PBM) cells[1] can be seeded at $1\times10^7$ cells in a total of 5 mL of RPMI-1640 (Mediatech Inc., Herndon, Va.) containing 100 mL heat inactivated fetal bovine serum (Hyclone, Logan, Utah), 83.3 IU/mL penicillin, 83.3 µg/mL streptomycin (Mediatech Inc., Herndon, Va.), 1.6 mM L-glutamine (Mediatech Inc., Herndon, Va.), 0.0008% DEAE-Dextran (Sigma-Aldrich, St. Louis, PBM cells can be separated by ficoll-hypaque (Histopaque 1077: Sigma) density gradient centrifugation from Buffy coats obtained from the American Red Cross (Atlanta, Ga.). Buffy coats can be derived from healthy, seronegative donors. Cells can be activated with 3 µg/mL phytohemagglutinin A (Sigma-Aldrich, St. Louis, Mo.) in 500 mL of RPMI-1640 (Mediatech Inc., Herndon, Va.) containing 100 mL heat inactivated fetal bovine serum (Hyclone, Logan, Utah), 83.3 IU/mL penicillin, 83.3 µg/mL streptomycin, 1.6 mM L-glutamine (Mediatech Inc., Herndon, Va.), for 2-3 days prior to use. Peripheral blood mononuclear (PBM) cells can be seeded at $1\times10^7$ cells in a total of 5 mL of RPMI-1640 (Mediatech Inc., Herndon, Va.) containing 100 mL heat inactivated fetal bovine serum (Hyclone, Logan, Utah), 83.3 IU/mL penicillin, 83.3 µg/mL streptomycin (Mediatech Inc., Herndon, Va.), 1.6 mM L-glutamine (Mediatech Inc., Herndon, Va.), 0.0008% DEAE-Dextran (Sigma-Aldrich, St. Louis, Mo.), 0.047% sodium bicarbonate, and 26 IU/mL recombinant interleukin-2 (Chiron Corporation, Emeryville, Calif.) in two T25 flask, one control (untreated) and one treated with drug.

HIV-1/LAI can be obtained from the Center for Disease Control and Prevention and used as the virus for the resistant pool and a multiplicity of infection (MOI) of 0.1, as determined by a limiting dilution method in PBM cells, can be selected to begin the infected pool. Naive PBM cells can be treated with nucleotide monophosphate prodrug at 0.1 µM for one hour prior to inoculation with HIV-$1_{LAI}$ at 100 ×$TCID_{50}$. The treated PBM cell group and a control nontreated PBM cell group can be allowed to infect, for example, for one hour. An additional 5 mL RTU medium can be added to each flask and cells can be incubated, for example, for 6 days at 37° C.

On day 6, 1 mL of supernatant from each flask can be removed and spun at 9,740 g at 4° C. for 2 hr. The resulting viral pellet can then be resuspended in virus solubilization buffer for RT analysis. Total RNA can be isolated from culture supernatants using the commercial QIAmp Viral RNA mini kit (Quiagen). Sequencing can be performed in parallel between the control virus and nucleotide monophosphate prodrug treated virus to determine if there are any mutations created by the applied drug pressure on weeks where the virus appears to be resistant.

The percent inhibition of the treated viral pool relative to the untreated viral pool can be calculated and closely monitored weekly prior to treatment. The selective pressure for the viral pool can be increased from 0.1 µM to 3.5 µM (40 times the $EC_{50}$ value) over a period of as many as 47 weeks or more.

Example 22

Synthesis of Nucleoside Analog Triphosphates

Nucleoside analog triphosphates were synthesized from the corresponding nucleosides, using the Ludwig and Eckstein's method. (Ludwig J, Eckstein F. "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one" *J. Org. Chem.* 1989, 54 631-5) The crude nucleoside analog triphosphate can be purified, for example, by FPLC using a HiLoad 26/10 Q Sepharose Fast Flow Pharmacia column and gradient of TEAB buffer (pH 7.0). The product will be characterized by UV spectroscopy, proton and phosphorus NMR, mass spectroscopy and HPLC.

The resulting triphosphates can be used as controls for the celluar pharmacology assays described above and for kinetic work with HIV-RT (for example, 6-substituted-2-amino purine nucleoside triphosphate with HIV-RT).

Example 23

Screening Assays for Activity Against HSV-1 and HSV-2

In the CPE-inhibition assay, drug can be added 1 h prior to infection so the assay system will have maximum sensitivity and detect inhibitors of early replicative steps such as adsorption or penetration as well as later events. To rule out non-specific inhibition of virus binding to cells, all compounds that show reasonable activity in the CPE assay can be confirmed using a classical plaque reduction assay in which the drug is added 1 h after infection. In the case where a compound blocks attachment, it will show up positive in the CPE assay, but may be negative by plaque assay. Efficacy: a minimum of six drug concentrations would be used covering a range of 100 mg/ml to 0.03 mg/ml, in 5-fold increments. From these data can be calculated the dose that inhibits viral replication by 50% (effective concentration 50; $EC_{50}$). Toxicity: The same drug concentrations used to determine efficacy can also used on uninfected cells in each assay to determine toxicity of each experimental compound. The drug concentration that is cytotoxic to cells as determined by their failure to take up a vital strain, neutral red.

HSV-1 drug susceptibility assay can also be done as previously described in: Schinazi, R. F., Peters, J., Williams, C. C., Chance, D., Nahmias, A. J. "Effect of combinations of acyclovir with vidarabine or its 5'-monophosphate on herpes simplex virus in cell culture and in mice." *Antimicrob. Agents Chemother.* 1982, 22, 499-507.

Example 24

HCV Replicon Assay[1]

Huh 7 Clone B cells containing HCV Replicon RNA would be seeded in a 96-well plate at 5000 cells/well, and the compounds tested at 10 μM in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds was also calculated by using the ΔCt rRNA values. (2'-Me-C) was used as the control. To determine $EC_{90}$ and $IC_{50}$ values[2], ΔCt: values were first converted into fraction of starting material[3] and then were used to calculate the % inhibition.

References

1. Stuyver L et al., Ribonucleoside analogue that blocks replication or bovine viral diarrhea and hepatitis C viruses in culture. *Antimicrob. Agents Chemother.* 2003, 47, 244-254.
2. Reed I J & Muench H, A simple method or estimating fifty percent endpoints. *Am. J. Hyg.* 27: 497, 1938.
3. Applied Biosystems Handbook

Example 25

West Nile virus drug susceptibility assays can also be done as previously described in: Song, G. Y., Paul, V., Choo, H., Money, J., Sidwell, R. W., Schinazi, R. F., Chu, C. K. Enantiomeric synthesis of D- and L-cyclopentenyl nucleosides and their antiviral activity against HIV and West Nile virus. *J. Med. Chem.* 2001, 44, 3985-3993.

Example 26

Yellow fever drug susceptibility assays can also be done as previously described in: Julander, J. G., Furuta, Y., Shafer, K.; Sidwell, R. W. Activity of T-1106 in a Hamster Model of Yellow Fever Virus Infection. *Antimicrob. Agents Chemother.* 2007, 51, 1962-1966.

Example 27

One representative high throughput assay for identifying compounds useful for treating Dengue is described in Lim et al., A scintillation proximity assay for dengue virus NS5 2'-O-methyltransferase-kinetic and inhibition analyses, Antiviral Research, Volume 80, Issue 3, December 2008, Pages 360-369.

Dengue virus (DENV) NS5 possesses methyltransferase (MTase) activity at its N-terminal amino acid sequence and is responsible for formation of a type 1 cap structure, m7 GpppAm2'-O in the viral genomic RNA. Optimal in vitro conditions for DENV2 2'-O-MTase activity can be characterized using purified recombinant protein and a short biotinylated GTP-capped RNA template. Steady-state kinetics parameters derived from initial velocities can be used to establish a robust scintillation proximity assay for compound testing. Pre-incubation studies by Lim et al., Antiviral Research, Volume 80, Issue 3, December 2008, Pages 360-369, showed that MTase-AdoMet and MTase-RNA complexes were equally catalytically competent and the enzyme supports a random bi bi kinetic mechanism. Lim validated the assay with competitive inhibitory agents, S-adenosyl-homocysteine and two homologues, sinefungin and dehydrosinefungin. A GTP-binding pocket present at the N-terminal of DENV2 MTase was previously postulated to be the cap-binding site. This assay allows rapid and highly sensitive detection of 2'-O-MTase activity and can be readily adapted for high-throughput screening for inhibitory compounds. It is suitable for determination of enzymatic activities of a wide variety of RNA capping MTases.

Example 28

Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473)

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay may be useful for screening entry inhibitors.

Example 29

Phosphorylation Assay of Nucleoside to Active Triphosphate in HepG2 Cells

To determine the cellular metabolism of the compounds, HepG2 cells can be obtained from the American Type Culture Collection (Rockville, Md.), and can be grown in 225 cm$^2$ tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells can be seeded at a density of 2.5×10$^6$ cells per well in a 6-well plate and exposed to 10 μM of [$^3$H] labeled active compound (500 dpm/pmol) for the specified time periods.

The cells are maintained at 37° C. under a 5% CO$_2$ atmosphere. At the selected time points, the cells are washed three times with ice-cold phosphate-buffered saline (PBS).

Intracellular active compound and its respective metabolites are extracted by incubating the cell pellet overnight at −20° C. with 60% methanol followed by extraction with an additional 20 pal of cold methanol for one hour in an ice bath. The extracts are then combined, dried under gentle filtered air flow and stored at −20° C. until HPLC analysis.

Example 30

Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives approximately 250 μCi of $^3$H activity with each dose of active compound at a dose level of 10 mg/kg at a dose concentration of 5 mg/mL$^1$, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (TmaX), area under the curve (AUC), half life of the dosage concentration (TV), clearance (CL), steady state volume and distribution (Vss) and bioavailability (F).

Example 31

Cell Protection Assay (CPA)

The assay is performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound"PNAS USA 2000, 97 (14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate.

Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm.

The 50% effective concentration (EC$_{50}$) values are defined as the compound concentration that achieved 50% reduction of cytopathic effect of the virus.

Example 32

Plaque Reduction Assay

For a compound, the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Example 33

Yield Reduction Assay

For a compound, the concentration to obtain a 6-log reduction in viral load is determined in duplicate 24-well plates by yield reduction assays. The assay is performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986, with minor modifications.

Briefly, MDBK cells are seeded onto 24-well plates ($2 \times 10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates ($5 \times 10^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 34

Diagnosis of Norovirus Infection

One can diagnose a norovirus infection by detecting viral RNA in the stools of affected persons, using reverse transcription-polymerase chain reaction (RT-PCR) assays. The virus can be identified from stool specimens taken within 48 to 72 hours after onset of symptoms, although one can obtain satisfactory results using RT-PCR on samples taken as long as 7 days after the onset of symptoms. Other diagnostic methods include electron microscopy and serologic assays for a rise in titer in paired sera collected at least three weeks apart. There are also commercial enzyme-linked immunoassays available, but these tend to have relatively low sensitivity, limiting their use to diagnosis of the etiology of outbreaks. Clinical diagnosis of norovirus infection is often used, particularly when other causative agents of gastroenteritis have been ruled out.

Example 35

In Vitro Anti-Viral Activity

In vitro anti-viral activity can be evaluated in the following cell lines:

The Norwalk G-I strain (Chang, K. O., et al. (2006) Virology 353:463-473), the GII-4 strain replicon, as well other Norovirus replicons can be used in assays to determine the in vitro antiviral activity of the compounds described herein, or other compounds or compound libraries.

In some embodiments, the replicon systems are subgenomic and therefore allow evaluation of small molecule inhibitors of non-structural proteins. This can provide the same benefits to Norovirus drug discovery that Hepatitis C replicons contributed to the discovery of therapeutics useful for treatment of that virus (Stuyver, L. J., et al. (2006) Antimicrob. Agents Chemother. 47:244-254). Both Norovirus replicons and Hepatitis C replicons require viral helicase, protease, and polymerase to be functional in order for replication of the replicon to occur. It is believed that the compounds described herein inhibit viral polymerase and/or viral helicase.

The in vitro cell culture infectivity assay reported using Norovirus genogroup I and II inoculums (Straub, T. M. et al. (2007) Emerg. Infect. Dis. 13(3):396-403) can also be used. This assay can be performed in a rotating-wall bioreactor utilizing small intestinal epithelial cells on microcarrier beads. The infectivity assay can be used for screening compounds for their ability to inhibit the desired virus.

Example 36

Screening Method for Identifying Anti-Cancer Compounds

A representative screening method for identifying anti-cancer compounds is described in Skehan et al., Journal of the National Cancer Institute, Vol. 82, No. 13, 1107-1112, Jul. 4, 1990.

The method in Skehan measures the cellular protein content of adherent and suspension cultures in 96-well microtiter plates, and is suitable for ordinary laboratory purposes and for very large-scale applications.

Cultures are fixed with trichloroacetic acid and stained for 30 minutes with 0.4% (wt/vol) sul-forhodamine B (SRB) dissolved in 1% acetic acid. Unbound dye is removed by four washes with 1% acetic acid, and protein-bound dye is extracted with 10 mM unbuffered Tris base [tris (hydroxymethyl)aminomethane] for determination of optical density in a computer-interfaced, 96-well microtiter plate reader.

The SRB assay results are linear with the number of cells and with values for cellular protein measured by both the Lowry and Bradford assays at densities ranging from sparse subconfluence to multilayered supraconfluence.

The signal-to-noise ratio at 564 nm is approximately 1.5 with 1,000 cells per well. The sensitivity of the SRB assay compares favorably with sensitivities of several fluorescence assays and is purportedly superior to those of both the Lowry and Bradford assays and to those of 20 other visible dyes. The SRB assay provides a colorimetric end point that is nondestructive, indefinitely stable, and visible to the naked eye. It provides a sensitive measure of drug-induced cytotoxicity, is useful in quantitating clonogenicity, and is well suited to high-volume, automated drug screening. SRB fluoresces strongly with laser excitation at 488 nm and can be measured quantitatively at the single-cell level by static fluorescence cytometry.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I):

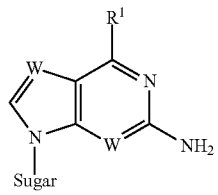

or a pharmaceutically acceptable salt or prodrug thereof, wherein:

$R^1$ is an atom or group removed in vivo to form OH when administered as the parent nucleoside, ii) W is, independently, N, CH, CF, CCN, CC≡CH, or $CC(O)N(R')_2$;

iii) Sugar is ribose or modified ribose of the general formula (II):

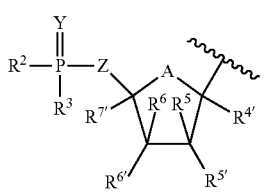

wherein:

Y is O or S;

Z is selected from the group consisting of $CL_2$, $CL_2CL_2$, $CL_2OCL_2$, $CL_2SCL_2$, $CL_2O$, $OCL_2$ and $CL_2NHCL_2$, wherein L independently is selected from the group consisting of H, F, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl may each optionally contain one or more heteroatoms;

A is O, S, $CH_2$, CHF, $CF_2$, C=$CH_2$, C=CHF, or C=$CF_2$;

$R^{4'}$, $R^5$, $R^{5'}$, $R^6$, $R^{6'}$, and $R^{7'}$ are independently selected from the group consisting of H, F, Cl, Br, I, OH, SH, $NH_2$, NHOH, $NHNH_2$, $N_3$, C(O)OH, CN, $C(O)NH_2$, $C(S)NH_2$, C(O)OR, R, OR, SR, SSR, NHR, and $NR_2$;

wherein for formula (I) where sugar is formula (II), when A is O, and $R^{4'}$, $R^5$, $R^{5'}$, $R^6$, $R^{7'}$ are H, $R^{6'}$ cannot be $N_3$;

wherein for formula (I) where sugar is formula (II), when A is O or S $R^{7'}$ cannot be OH, SH, $NH_2$, NHOH, $NHNH_2$, OR, SR, SSR, NHR, and $NR_2$;

R is independently $C_1$-$C_6$ alkyl, $C_2$-$C_6$ alkenyl, $C_2$-$C_6$ alkynyl, $C_3$-$C_6$ cycloalkyl, aryl, alkylaryl, or arylalkyl, wherein the groups can be substituted with one or more substituents selected from the group consisting of hydroxyalkyl, aminoalkyl, and alkoxyalkyl, $R^2$ is O-phenyl, where phenyl is substituted with $(CH_2)_{1-6}CO_2R^{9a}$, and, optionally, one or two substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{9a}$, halogen, $C_{1-6}$ haloalkyl, —$N(R^{9a})_2$, $C_{1-6}$ acylamino, —$NHSO_2C_{1-6}$ alkyl, —$SO_2N(R^{9a})_2$, —$SO_2C_{1-6}$ alkyl, $COR^{9b}$, nitro and cyano;

and $R^3$ is selected from:

(a) $OR^8$ where $R^8$ is H, $C_{1-20}$ alkyl, $C_{3-6}$ cycloalkyl, $C_{1-6}$ haloalkyl, aryl, or heteroaryl optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{9a}$, halogen, $C_{1-6}$ haloalkyl, —$N(R^{9a})_2$, $C_{1-6}$ acylamino, —$NHSO_2C_{1-6}$ alkyl, —$SO_2N(R^{9a})_2$, —$SO_2C_{1-6}$ alkyl, $COR^{9b}$, nitro and cyano;

$R^{9a}$ is independently H or $C_{1-6}$ alkyl;

$R^{9b}$ is —$OR^{9a}$ or —$N(R^{9a})_2$;

(b) 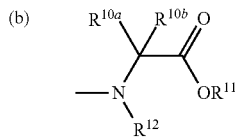

where $R^{10a}$ and $R^{10b}$ are:

(i) independently selected from the group consisting of H, $C_{1-10}$ alkyl, —$(CH_2)_rNR^{9a}_2$, $C_{1-6}$ hydroxyalkyl, —$CH_2SH$, —$(CH_2)_2S(O)_p$Me, —$(CH_2)_3NHC(=NH)NH_2$, (1H-indol-3-yl) methyl, (1H-imidazol-4-yl)methyl, —$(CH_2)_mCOR^{9b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;

(ii) $R^{10a}$ is H and $R^{10b}$ and $R^{12}$ together are $(CH_2)_{2-4}$ to form a ring that includes the adjoining N and C atoms;

(iii) $R^{10a}$ and $R^{10b}$ together are $(CH_2)_n$ to form a ring;
(iv) $R^{10a}$ and $R^{10b}$ both are $C_{1-6}$ alkyl; or
(v) $R^{10a}$ is H and $R^{10b}$ is H, $CH_3$, $CH_2CH_3$, CH$(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$—$CH_2CH_2CH_2NHC(NH)NH_2$, $CH_2$-imidazol-4-yl, $CH_2OH$, $CH(OH)CH_3$, $CH_2((4'\text{-}OH)\text{-}Ph)$, $CH_2SH$, or $C_{3-6}$ cycloalkyl;

p is 0 to 2;
r is 1 to 6;
n is 4 or 5;
m is 0 to 3;

$R^{11}$ is H, $C_{1-10}$ alkyl, or $C_{1-10}$ alkyl substituted with a $C_{1-6}$ alkyl, alkoxy, di($C_{1-6}$ alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower $C_{1-6}$ alkyl, alkoxy, di($C_{1-6}$ alkyl)-amino, fluoro, $C_{3-10}$ cycloalkyl, or cycloalkyl;

$R^{12}$ is H, $C_{1-3}$ alkyl, or $R^{10a}$, or $R^{10b}$ and $R^{12}$ together are $(CH_2)_{2-4}$ so as to form a ring that includes the adjoining N and C atoms;

(c) an O attached lipid, an N or O attached peptide, an O attached cholesterol, or an O attached phytosterol;

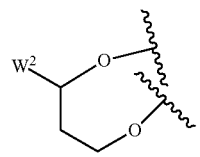

(d) $R^2$ and $R^3$ may come together to form a ring
where $W^2$ is selected from the group consisting of phenyl or monocyclic heteroaryl, optionally substituted with one to three substituents independently selected from the group consisting of $C_{1-6}$ alkyl, $CF_3$, $C_{2-6}$ alkenyl, $C_{1-6}$ alkoxy, $OR^{9c}$, $CO_2R^{9a}$, $COR^{9a}$, halogen, $C_{1-6}$ haloalkyl, —$N(R^{9a})_2$, $C_{1-6}$ acylamino, $CO_2N(R^{9a})_2$, $SR^{9a}$, —$NHSO_2C_{1-6}$ alkyl, —$SO_2N(R^{9a})_2$, —$SO_2C_{1-6}$ alkyl, $COR^{9b}$, and cyano, and wherein said monocyclic heteroaryl and substituted monocyclic heteroaryl has 1-2 heteroatoms that are independently selected from the group consisting of N, O, and S with the provisos that:
a) when there are two heteroatoms and one is O, then the other can not be O or S, and
b) when there are two heteroatoms and one is S, then the other can not be O or S;
$R^{9a}$ is independently H or $C_{1-6}$ alkyl;
$R^{9b}$ is —$OR^{9a}$ or —$N(R^{9a})_2$;
$R^{9c}$ is H or $C_{1-6}$ acyl;

(e) 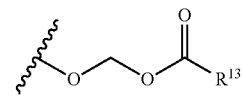

where $R^{13}$ is selected from the group consisting of H, $C_{1-10}$ alkyl, $C_{1-10}$ alkyl optionally substituted with a $C_{1-6}$ alkyl, alkoxy, di($C_{1-6}$ alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$ alkyl, alkoxy, di($C_{1-6}$ alkyl)-amino, fluoro, $C_{3-10}$ cycloalkyl, or $C_{3-6}$ cycloalkyl;

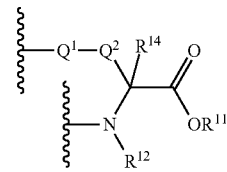

f) $R^2$ and $R^3$ may come together to form a ring
where $R^{14}$ is: (i) independently selected from the group consisting of H, $C_{1-10}$ alkyl, —$(CH_2)_rNR_2^{9a}$, $C_{1-6}$ hydroxyalkyl, —$CH_2SH$, —$(CH_2)_2S(O)_pMe$, —$(CH_2)_3NHC(\!\!=\!\!NH)NH_2$, (1H-indol-3-yl)methyl, (1H-imidazol-4-yl)methyl, —$(CH_2)_mCOR^{9b}$, aryl and aryl-$C_{1-3}$ alkyl or heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen, nitro, and cyano; (ii) $R^{14}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'\text{-}OH)\text{-}Ph)$, $CH_2SH$, or lower cycloalkyl;

p is 0 to 2;
r is 1 to 6;
m is 0 to 3
$Q^1$ is $NR^{9a}$, O, or S
$Q^2$ is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, fluoro, and chloro;

$R^{11}$ is H, $C_{1-10}$ alkyl, $C_{1-10}$ alkyl optionally substituted with a $C_{1-6}$ alkyl, alkoxy, di($C_{1-6}$ alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a $C_{1-6}$alkyl, alkoxy, di($C_{1-6}$ alkyl)-amino, fluoro, $C_{3-10}$ cycloalkyl, or cycloalkyl;

$R^{12}$ is H or $C_{1-3}$ alkyl, or $R^{14b}$ and $R^{12}$ together are $(CH_2)_{2-4}$ so as to form a ring that includes the adjoining N and C atoms;

iv) alternatively Sugar is a modified ribose of the general formula (III):

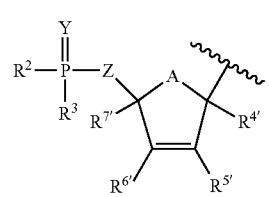

(III)

wherein:
wherein for formula (I) where sugar is formula (III), when A is O or S $R^{7'}$ cannot be OH, SH, $NH_2$, NHOH, $NHNH_2$, OR, SR, SSR, NHR, and $NR_2$, R is independently $C_1$-$C_6$ alkyl, $C_2$-$C_6$ alkenyl, $C_2$-$C_6$ alkynyl, $C_3$-$C_6$ cycloalkyl, aryl, alkylaryl, or arylalkyl, wherein the groups can be substituted with one or more substituents selected from the group consisting of hydroxyalkyl, aminoalkyl, and alkoxyalkyl;

v) alternatively Sugar is a dioxolane or a oxathiolane of the general formulas (IV), (V), (VI), and (VII):

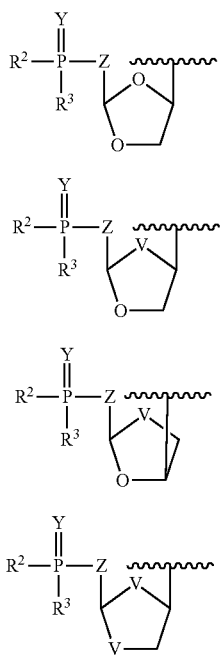

wherein:
V is S or Se vi) alternatively Sugar is a modified ribose of the general formulas (XI):

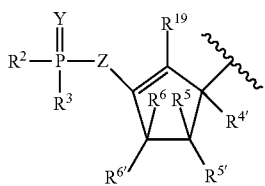

wherein:
$R^{19}$ is H, F, Cl, Br, I, $N_3$, C(O)OH, CN, C(O)$NH_2$, C(S)$NH_2$, C(O)OR, R R is independently a $C_{1-6}$ alkyl ($C_1$-$C_6$ alkyl), $C_{2-6}$ alkenyl, $C_{2-6}$ alkynyl, $C_{3-6}$ cycloalkyl aryl, alkylaryl, or arylalkyl, wherein the groups can be substituted with one or more substituents selected from the group consisting of hydroxyalkyl, aminoalkyl, and alkoxyalkyl, wherein the compounds can be in the form of the β-L- or β-D-configuration, or a mixture thereof, including a racemic mixture thereof.

2. The compound of claim 1, wherein $R^{6'}$ selected from the group consisting of H, F, Cl, Br, I, OH, SH, $NH_2$, NHOH, $NHNH_2$, C(O)OH, CN, C(O)$NH_2$, C(S)$NH_2$, C(O)OR, R, OR, SR, SSR, NHR, and $NR_2$.

3. The compounds of claim 1, wherein $R^5$ is selected from the group consisting of $NH_2$, dimethylamine, methyl-allyl-amine, methoxy, chloro, cyclopropylamine, 5-hydroxy-pentylamine, 1,1-dimethyl-ethanolamine, and 2-methoxy-ethylamine.

4. The compounds of claim 1, wherein the compounds are in the β-L- or β-D configuration, or a racemic mixture thereof.

5. A method for treating a host infected with HIV-1 or HIV-2, or reducing the biological activity of an HIV-1 or HIV-2 infection in a host, comprising administering an effective amount of a compound of claim 1 to a patient in need of treatment thereof.

6. The method of claim 5, wherein the HIV-1 or HIV-2 infection is caused by a virus comprising a mutation selected from the group consisting of TAM mutations and the M184V mutation.

7. The method of claim 5, wherein the compound is administered in combination with another anti-HIV agent.

8. The method of claim 7, wherein the HIV-1 or HIV-2 infection is caused by a virus comprising a mutation selected from the group consisting of TAM mutations and the M184V mutation.

9. A method for treating a host infected with HBV, or for reducing the biological activity of an HBV infection in a host, comprising administering an effective amount of a compound of claim 1 to a patient in need of treatment thereof.

10. The method of claim 7, wherein the compound is administered in combination with another anti-HBV agent.

11. A method for treating a host infected with Norovirus or Saporovirus, or reducing the biological activity of an Norovirus or Saporovirus infection in a host, comprising administering an effective amount of a compound of claim 1 to a patient in need of treatment thereof.

12. The method of claim 11, wherein the compound is administered in combination with another anti-Norovirus or anti-Saporovirus agent.

13. A method for treating a host infected with a Flaviviridae virus or reducing the biological activity of an infection with a Flaviviridae virus in a host, comprising administering an effective amount of a compound of claim 1 to a patient in need of treatment thereof.

14. A method for treating a host infected with HSV-1 or HSV-2, or reducing the biological activity of an HSV-1 or HSV-2 infection in a host, comprising administering an effective amount of a compound of claim 1 to a patient in need of treatment thereof.

15. The method of claim 10, wherein the compound is administered in combination with another anti-HSV-1 AND HSV-2 agent.

16. The compound of claim 1, wherein $R^1$ is selected from the group consisting of halogen, OR', N(R')$_2$, SR', OCOR', NHCOR', N(COR')COR', SCOR', OCOOR', and NHCOOR', and wherein each R' is independently H, a $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_6$ cycloalkyl, aryl, heteroaryl, alkylaryl, or arylalkyl, wherein the groups can be substituted with one or more hydroxyalkyl, aminoalkyl, or alkyoxyalkyl substituents.

17. The method of claim 13, wherein the virus is selected from the group consisting of HCV, Yellow fever, Dengue, and West Nile virus.

18. A compound of claim 1 or a pharmaceutically acceptable salt or prodrug thereof, wherein the lipid is a phospholipid.

* * * * *